US010286060B2

(12) United States Patent
Gilbert et al.

(10) Patent No.: US 10,286,060 B2
(45) Date of Patent: May 14, 2019

(54) COMPOSITIONS AND METHODS

(71) Applicant: Isis Innovation Limited, Oxford (GB)

(72) Inventors: Sarah Gilbert, Oxford (GB); Adrian V. S. Hill, Oxford (GB); Anne Moore, Oxford (GB)

(73) Assignee: OXFORD UNIVERSITY INNOVATION LIMITED, Oxford (GB)

( * ) Notice: Subject to any disclaimer, the term of this patent is extended or adjusted under 35 U.S.C. 154(b) by 0 days.

(21) Appl. No.: 14/523,345

(22) Filed: Oct. 24, 2014

(65) Prior Publication Data

US 2015/0110831 A1 Apr. 23, 2015

Related U.S. Application Data

(62) Division of application No. 12/239,969, filed on Sep. 29, 2008, now abandoned.

(30) Foreign Application Priority Data

| Oct. 5, 2007 | (GB) | .................................... | 0719526.6 |
| Dec. 28, 2007 | (GB) | ................................ | 07255070.0 |
| Sep. 10, 2008 | (GB) | .................................... | 0816534.2 |

(51) Int. Cl.
*A61K 39/145* (2006.01)
*A61K 39/12* (2006.01)
*A61K 39/00* (2006.01)

(52) U.S. Cl.
CPC ............ *A61K 39/145* (2013.01); *A61K 39/12* (2013.01); *A61K 2039/5256* (2013.01); *A61K 2039/53* (2013.01); *A61K 2039/54* (2013.01); *A61K 2039/545* (2013.01); *A61K 2039/6025* (2013.01); *A61K 2039/627* (2013.01); *A61K 2039/70* (2013.01); *C12N 2710/10343* (2013.01); *C12N 2710/24143* (2013.01); *C12N 2760/16134* (2013.01)

(58) Field of Classification Search
None
See application file for complete search history.

(56) References Cited

FOREIGN PATENT DOCUMENTS

| WO | 05/71093 | 8/2005 |
| WO | 06/48215 | 5/2006 |
| WO | 07/16598 | 2/2007 |
| WO | 07/92792 | 8/2007 |

OTHER PUBLICATIONS

Bardenheier et al., "Influenza vaccine supply, 2005-2006: did we come up short?," BMC Health Services Research, 7:66 (2007).

Bejon et al., "Safety Profile of the Viral Vectors of Attenuated Fowlpox Strain FP9 and Modified Vaccinia Virus Ankara Recombinant for Either of 2 Preerythrocytic Malaria Antigens, ME-TRAP or the Circumsporozoite Protein, in Children and Adults in Kenya," Clinical Infectious Diseases, 42:1102-1110 (2006).

Blanchard et al., "Modified vaccinia virus Ankara undergoes limited replication in human cells and lacks several immunomodulatory proteins: implications for use as human vaccine," Journal of General Virology, 79:1159-1167 (1998).

Cohen et al., "Chimpanzee adenovirus CV-68 adapted as a gene delivery vector interacts with the coxsackievirus and adenovirus receptor," Journal of General Virology, 83:151-155 (2002).

Goonetilleke et al., "Induction of Multifunctional Human Immunodeficiency Virus Type 1 (HIV-1)-Specific T Cells Capable of Proliferation in Healthy Subjects by Using a Prime-Boost Regimen of DNA- and Modified Vaccinia Virus Ankara-Vectored Vaccines Expressing HIV-1 Gag Coupled to CD8+ T-Cell Epitopes," Journal of Virology, 80 (10):4717-4728 (2006).

Kreijtz et al., "Recombinant Modified Vaccinia Virus Ankara-Based Vaccine Induces Protective Immunity in Mice Against Infection with Influenza Virus H5N1," The Journal of Infectious Diseases, 195:1598-1606 (2007).

McConkey et al., "Enhanced T-cell immunogenicity of plasmid DNA vaccines boosted by recombinant modified vaccinia virus Ankara in humans," Nature Medicine, 9(6):729-735 (2003).

Moorthy et al., "Safety and Immunogenicity of DNA/Modified Vaccinia Virus Ankara Malaria Vaccination in Africa Adults," The Journal of Infectious Diseases, 188:1239-1244 (2003).

Stephenson et al., "Cross-Reactivity to Highly Pathogenic Avian Influenza H5N1 Viruses after Vaccination with Nonadjuvanted and MF59-Adjuvanted Influenza A/Duck/Sigapore/97 (H5N3) Vaccine: A Potential Priming Strategy," The Journal of Infectious Diseases, 191:1210-1215 (2005).

Sutter et al., "Nonreplicating vaccinia vector efficiently expresses recombinant genes," Proc. Natl. Acad. Sci., 89:10847-10851 (1992).

Treanor et al., "Safety and Immunogenicity of an Inactivated Subvirion Influenza A (H5N1) Vaccine," The New England Journal of Medicine, 354(13):1343-1351 (2006).

Webster et al., "Enhanced T cell-mediated protection against malaria in human challenges by using the recombinant poxviruses FP9 and modified vaccinia virus Ankara," PNAS, 102(13):4836-4841 (2005).

European Search Report corresponding to European Application No. 07255070.0 dated Jan. 13, 2009.

Schneider et al., "Enhanced immunogenicity for CD8+ T cell induction and complete protective efficacy of malaria DNA vaccination by boosting with modified vaccinia virus Ankara," Nature Medicine, 4(4):397-402 (1998).

(Continued)

*Primary Examiner* — Benjamin P Blumel
(74) *Attorney, Agent, or Firm* — McAndrews, Held & Malloy, Ltd.

(57) ABSTRACT

The invention relates to a composition suitable for inducing a T cell mediated immune response against an influenza virus in a vertebrate, said composition comprising nucleic acid encoding one or more epitopes of one or more internal proteins of influenza virus, wherein said composition comprises nucleic acid encoding at least two said epitopes, at least one epitope being from each of two or more internal proteins of influenza virus. The invention also relates to uses of same and to methods involving same.

7 Claims, 31 Drawing Sheets

Specification includes a Sequence Listing.

(56) References Cited

OTHER PUBLICATIONS

Dorrell et al., "Recombinant modified vaccinia virus Ankara efficiently restimulates human cytotoxic T lymphocytes in vitro," Vaccine, 19:327-336 (2001).
Donnelly et al., "Further protection against antigenic drift of influenza virus in a ferret model by DNA vaccination," Vaccine, 15(8):865-868 (1997).
Jimenez et al., "Vaxfection—Formulated Influenza DNA Vaccines Encoding NP and M2 Viral Proteins Protect Mice against Lethal Viral Challenge," Human Vaccines, 3(5):157-164 (2007).
Babakir-Mina et al., "Influenza virus A (H5N1): a pandemic risk?," New Microbiologica, 30:65-77 (2007).
Breathnach et al., "Use of recombinant modified vaccinia Ankara viral vectors for equine influenza vaccination," Veterinary Immunology and Immunopathology, 98:127-136 (2004).
Bresson et al., "Safety and immunogenicity of an inactivated split-virion influenza A/Vietnam/1194/2004 (H5N1) vaccine: phase I randomised trail," Lancet, 367:1657-1664 (2006).
Cosma et al., "Therapuetic vaccination with MVA-HIV-1 nef elicits Nef-specific T-helper cell responses in chronically HIV-1 infected individuals, Vaccine, 22:21-29 (2003).
Dorrell et al., "Safety and tolerability of recombinant modified vaccinia virus Ankara expressing an HIV-1 gag/multipitope immunogen (MVA.HIVA) in HIV-1-infected persons receiving combination antiretroviral therapy," Vaccine, 25:3277-3283 (2007).
Epstein et al., "Protection against multiple influenza A subtypes by vaccination with highly conserved nucleoprotein," Vaccine, 23:5404-5410 (2005).
Le et al., "Avian Flu: Isolation of drug-resistant H5N1 virus," Nature, 437:1108 (2005).
Mayr et al., "The Smallpox Vaccination Strain MVA: Genetic Structure, Experience Gained with the Parenteral Vaccination and Behavior in Organisms with a Debilitated Defence Mechanism," Zbl. Bakt. Hyg., [B], 167:375-390 (1978).

McMichael et al., "Cytotoxic T-Cell Immunity to Influenza," The New England Journal of Medicine, 309(1):13-17 (1983).
Meyer et al., "A phase I vaccination study with tyrosinase in patients with stage II melanoma using recombinant modified vaccina virus Ankara (MVA-hTyr)," Cancer Immunol Immunother, 54:453-467 (2005).
Molinari et al., "The annual impact of seasonal influenza in the US: Measuring disease burden and costs," Vaccine, 25:5086-5096 (2007).
Peters et al., "Studies of a prophylactic HIV-1 vaccine candidate based on modified vaccinia virus Ankara (MVA) with and without DNA priming: Effects of dosage and route on safety and immunogenicity," Vaccine, 25:2120-2127 (2007).
Smith et al., "Recombinant Modified Vaccinia Ankara Primes Functionally Activated CTL Specific for a Melanoma Tumor Antigen Epitope in Melanoma Patients with a High Risk of Disease Recurrence," Int. J. Cancer, 113:259-266 (2005).
Tobery et al., "A simple and efficient method for the monitoring of antigen—specific T cell responses using peptide pool arrays in a modified ELISpot assay," Journal of Immunological Methods, 254:59-66 (2001).
Ulmer et al., "Heterologous Protection Against Influenza by Injection of DNA Encoding a Viral Protein," Science, 259:1745-1749 (1993).
Webster et al., "Safety of recombinant fowlpox strain FP9 and modified vaccinia virus Ankara vaccines against liver-stage *P. falciparum* malaria in non-immune volunteers," Vaccine, 24:3026-3034 (2006).
Hill, "Vaccines Theme," Slides, Apr. 25, 2007, 45 pages, The Jenner Institute, University of Oxford.
Gerhard et al., "Prospects for Universal Influenza Virus Vaccine", Emerging Infectious Diseases, www.cdc.gov/eid, vol. 12, No. 4, Apr. 2006, 6 pages.
Heinen et al., "Vaccination of pigs with a DNA construct expressing an influenza virus M2—nucleoprotein fusion protein exacerbates disease after challenge with influenza A virus", Journal of General Virology, (2002), 83, 1851-1859.
Szretter et al., "Role of Host Cytokine Responses in the Pathogenesis of Avian H5N1 Influenza Viruses in Mice", Journal of Virology, Mar. 2007, p. 2736-2744, vol. 81, No. 6.

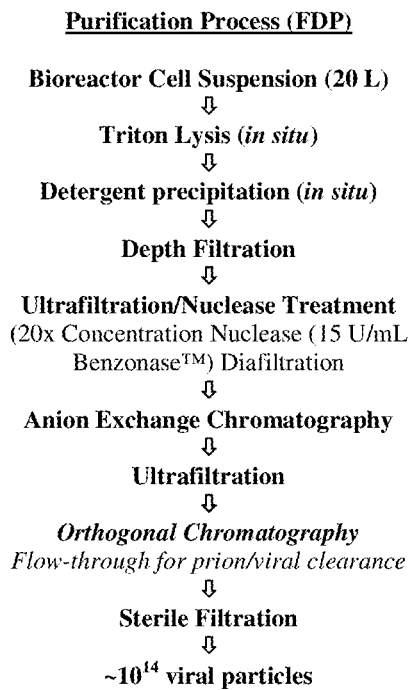

Purification Process (FDP)

Bioreactor Cell Suspension (20 L)
⇩
Triton Lysis (*in situ*)
⇩
Detergent precipitation (*in situ*)
⇩
Depth Filtration
⇩
Ultrafiltration/Nuclease Treatment
(20x Concentration Nuclease (15 U/mL
Benzonase™) Diafiltration
⇩
Anion Exchange Chromatography
⇩
Ultrafiltration
⇩
*Orthogonal Chromatography*
*Flow-through for prion/viral clearance*
⇩
Sterile Filtration
⇩
~$10^{14}$ viral particles

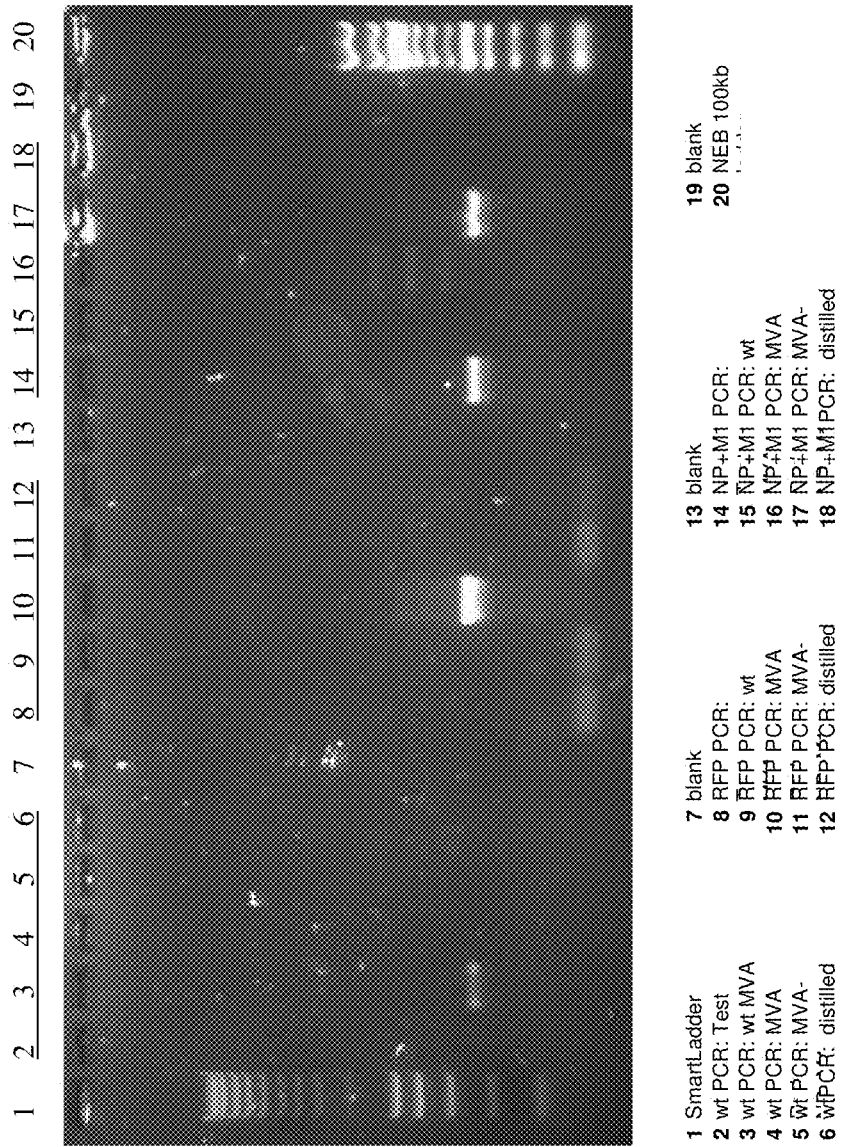

SEQUENCE LISTING

```
<160> NUMBER OF SEQ ID NOS: 86

<210> SEQ ID NO 1
<211> LENGTH: 757
<212> TYPE: PRT
<213> ORGANISM: Influenza virus
<220> FEATURE:
<221> NAME/KEY: MISC_FEATURE
<223> OTHER INFORMATION: A/Panama/2007/99 amino acid sequence, optimised
      for human codon usage, NP followed by linker (lower case -
      gggpggg) followed by M1

<400> SEQUENCE: 1

Met Ala Ser Gln Gly Thr Lys Arg Ser Tyr Glu Gln Met Glu Thr Asp
1               5                   10                  15

Gly Asp Arg Gln Asn Ala Thr Glu Ile Arg Ala Ser Val Gly Lys Met
                20                  25                  30

Ile Asp Gly Ile Gly Arg Phe Tyr Ile Gln Met Cys Thr Glu Leu Lys
            35                  40                  45

Leu Ser Asp Tyr Glu Gly Arg Leu Ile Gln Asn Ser Leu Thr Ile Glu
        50                  55                  60

Lys Met Val Leu Ser Ala Phe Asp Glu Arg Arg Asn Arg Tyr Leu Glu
65                  70                  75                  80

Glu His Pro Ser Ala Gly Lys Asp Pro Lys Lys Thr Gly Gly Pro Ile
                85                  90                  95

Tyr Arg Arg Val Asp Gly Lys Trp Met Arg Glu Leu Val Leu Tyr Asp
                100                 105                 110

Lys Glu Glu Ile Arg Arg Ile Trp Arg Gln Ala Asn Asn Gly Glu Asp
            115                 120                 125

Ala Thr Ala Gly Leu Thr His Met Met Ile Trp His Ser Asn Leu Asn
        130                 135                 140

Asp Thr Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Ile Gly Thr Met Val Met Glu
                180                 185                 190

Leu Ile Arg Met Val Lys Arg Gly Ile Asn Asp Arg Asn Phe Trp Arg
            195                 200                 205

Gly Glu Asn Gly Arg Lys Thr Arg Ser Ala Tyr Glu Arg Met Cys Asn
        210                 215                 220

Ile Leu Lys Gly Lys Phe Gln Thr Ala Ala Gln Arg Ala Met Val Asp
225                 230                 235                 240

Gln Val Arg Glu Ser Arg Asn Pro Gly Asn Ala Glu Ile Glu Asp Leu
```

```
                245                 250                 255
Ile Phe Leu Ala Arg Ser Ala Leu Ile Leu Arg Gly Ser Val Ala His
            260                 265                 270
Lys Ser Cys Leu Pro Ala Cys Val Tyr Gly Pro Ala Val Ser Ser Gly
            275                 280                 285
Tyr Asp Phe Glu Lys Glu Gly Tyr Ser Leu Val Gly Ile Asp Pro Phe
            290                 295                 300
Lys Leu Leu Gln Asn Ser Gln Val Tyr Ser Leu Ile Arg Pro Asn Glu
305                 310                 315                 320
Asn Pro Ala His Lys Ser Gln Leu Val Trp Met Ala Cys His Ser Ala
            325                 330                 335
Ala Phe Glu Asp Leu Arg Leu Leu Ser Phe Ile Arg Gly Thr Lys Val
            340                 345                 350
Ser Pro Arg Gly Lys Leu Ser Thr Arg Gly Val Gln Ile Ala Ser Asn
            355                 360                 365
Glu Asn Met Asp Asn Met Gly Ser Ser Thr Leu Glu Leu Arg Ser Gly
            370                 375                 380
Tyr Trp Ala Ile Arg Thr Arg Ser Gly Gly Asn Thr Asn Gln Gln Arg
385                 390                 395                 400
Ala Ser Ala Gly Gln Ile Ser Val Gln Pro Thr Phe Ser Val Gln Arg
            405                 410                 415
Asn Leu Pro Phe Glu Lys Ser Thr Val Met Ala Ala Phe Thr Gly Asn
            420                 425                 430
Thr Glu Gly Arg Thr Ser Asp Met Arg Ala Glu Ile Ile Arg Met Met
            435                 440                 445
Glu Gly Ala Lys Pro Glu Val Ser Phe Arg Gly Arg Gly Val Phe
            450                 455                 460
Glu Leu Ser Asp Glu Lys Ala Thr Asn Pro Ile Val Pro Ser Phe Glu
465                 470                 475                 480
Met Ser Asn Glu Gly Ser Tyr Phe Phe Gly Asp Asn Ala Glu Glu Tyr
            485                 490                 495
Asp Asn Gly Gly Gly Pro Gly Gly Gly Met Ser Leu Leu Thr Glu Val
            500                 505                 510
Glu Thr Tyr Val Leu Ser Ile Val Pro Ser Gly Pro Leu Lys Ala Glu
            515                 520                 525
Ile Ala Gln Arg Leu Glu Asp Val Phe Ala Gly Lys Asn Thr Asp Leu
            530                 535                 540
Glu Ala Leu Met Glu Trp Leu Lys Thr Arg Pro Ile Leu Ser Pro Leu
545                 550                 555                 560
Thr Lys Gly Ile Leu Gly Phe Val Phe Thr Leu Thr Val Pro Ser Glu
            565                 570                 575
Arg Gly Leu Gln Arg Arg Arg Phe Val Gln Asn Ala Leu Asn Gly Asn
            580                 585                 590
Gly Asp Pro Asn Asn Met Asp Lys Ala Val Lys Leu Tyr Arg Lys Leu
            595                 600                 605
Lys Arg Glu Ile Thr Phe His Gly Ala Lys Glu Ile Ala Leu Ser Tyr
            610                 615                 620
Ser Ala Gly Ala Leu Ala Ser Cys Met Gly Leu Ile Tyr Asn Arg Met
625                 630                 635                 640
Gly Ala Val Thr Thr Glu Val Ala Phe Gly Leu Val Cys Ala Thr Cys
            645                 650                 655
Glu Gln Ile Ala Asp Ser Gln His Arg Ser His Arg Gln Met Val Ala
            660                 665                 670
```

```
Thr Thr Asn Pro Leu Ile Lys His Glu Asn Arg Met Val Leu Ala Ser
        675                 680                 685

Thr Thr Ala Lys Ala Met Glu Gln Met Ala Gly Ser Ser Glu Gln Ala
    690                 695                 700

Ala Glu Ala Met Glu Ile Ala Ser Gln Ala Arg Gln Met Val Gln Ala
705                 710                 715                 720

Met Arg Thr Val Gly Thr His Pro Ser Ser Ser Thr Gly Leu Arg Asp
                725                 730                 735

Asp Leu Leu Glu Asn Leu Gln Thr Tyr Gln Lys Arg Met Gly Val Gln
            740                 745                 750

Met Gln Arg Phe Lys
        755
```

<210> SEQ ID NO 2
<211> LENGTH: 2274
<212> TYPE: DNA
<213> ORGANISM: Influenza virus
<220> FEATURE:
<221> NAME/KEY: misc_feature
<223> OTHER INFORMATION: nucleotide sequence encoding the A/Panama/2007/99 amino acid sequence of SEQ ID NO:1, optimised for human codon usage, NP followed by linker followed by M1.

<400> SEQUENCE: 2

```
atggccagcc agggcaccaa gcggagctac gagcagatgg aaaccgacgg cgaccggcag     60
aacgccaccg agatccgggc cagcgtgggc aagatgatcg acggcatcgg ccggttctac    120
atccagatgt gcaccgagct gaagctgtcc gactacgagg gccggctgat ccagaacagc    180
ctgaccatcg agaagatggt gctgtccgcc ttcgacgagc ggcggaacag atacctggaa    240
gagcacccca gcgccggcaa ggaccccaag aaaaccggcg gacccatcta ccggcgggtg    300
gacggcaagt ggatgcggga gctggtgctg tacgacaaag aggaaatccg gcggatctgg    360
cggcaggcca acaacggcga ggacgccaca gccggcctga cccacatgat gatctggcac    420
agcaacctga acgacaccac ctaccagcgg accagggccc tcgtgcggac cggcatggac    480
ccccggatgt gcagcctgat gcagggcagc acactgccca gaagaagcgg agctgccgga    540
gccgccgtga agggcatcgg caccatggtg atggaactga tccggatggt gaagcggggc    600
atcaacgacc ggaatttttg gaggggcgag aacggcagaa agactagaag cgcctacgag    660
cggatgtgca acatcctgaa gggcaagttc cagacagccg cccagcgggc catggtggac    720
caggtccggg agagccggaa ccccggcaac gccgagatcg aggacctgat cttcctggcc    780
cggtccgccc tgatcctgcg gggcagcgtg gcccacaaga gctgcctgcc cgcctgcgtg    840
tacggccctg ccgtgagcag cggctacgac ttcgagaaag agggctacag cctggtcggc    900
atcgacccct tcaagctgct gcagaacagc caggtgtaca gcctgatccg gcccaacgag    960
aaccccgccc acaagtccca gctggtctgg atggcctgcc acagcgccgc cttcgaggat   1020
ctgcggctgc tgtccttcat ccggggcacc aaggtgtccc ccaggggcaa gctgtccacc   1080
agaggcgtgc agatcgccag caacgagaac atggacaaca tgggcagcag caccctggaa   1140
ctgcggagcg gctactgggc catccggacc cggtccggcg gcaacaccaa ccagcagcgg   1200
gccagcgccg gacagatcag cgtgcagccc accttctccg tgcagcggaa cctgcccttc   1260
gagaagagca ccgtgatggc cgccttcacc ggcaacaccg agggccggac cagcgacatg   1320
cgggccgaga ttatccggat gatggaaggc gccaagcccg aggaagtgag cttccggggc   1380
aggggcgtgt tcgagctgtc cgatgagaag gccaccaacc ccatcgtgcc cagcttcgag   1440
```

```
atgagcaacg agggcagcta cttcttcggc gacaacgccg aggaatacga caatggcggc    1500
ggaccaggcg gcggaatgag cctgctgacc gaggtggaga cctacgtgct gtccatcgtg    1560
cctagcggcc ctctgaaggc cgagatcgcc cagcggctgg aagatgtgtt cgccggcaag    1620
aacaccgacc tggaagccct gatggaatgg ctgaaaaccc ggcccatcct gagcccctg     1680 accaagggca tcctgggctt cgtgttcacc ctgaccgtgc ccagcgagcg gggcctgcag    1740
cggcggagat tcgtgcagaa cgccctgaac ggcaacggcg accccaacaa catggataag    1800
gccgtgaagc tgtaccggaa gctgaagcgg gagatcacct tccacggcgc caagagatc    1860 gccctgagct acagcgccgg agccctggcc agctgcatgg gcctgatcta accggatg     1920 ggcgccgtga ccaccgaggt ggccttcggc ctggtctgcg ccacctgcga gcagatcgcc    1980
gacagccagc acagatccca ccggcagatg gtggccacaa ccaaccctct gatcaagcac    2040
gagaaccgga tggtgctggc tagcaccacc gccaaggcca tggaacagat ggccggcagc    2100
agcgagcagg ccgccgaagc catggaaatc gccagccagg ccagacagat ggtgcaggcc    2160
atgcggaccg tgggcaccca ccccagcagc tccaccggcc tgcgggacga cctgctggaa    2220
aacctgcaga cctaccagaa acggatgggg gtgcagatgc agcggttcaa gtga          2274

<210> SEQ ID NO 3
<211> LENGTH: 7
<212> TYPE: PRT
<213> ORGANISM: Artificial Sequence
<220> FEATURE:
<223> OTHER INFORMATION: Amino Acid Linker Sequence

<400> SEQUENCE: 3

Gly Gly Gly Pro Gly Gly Gly
1               5

<210> SEQ ID NO 4
<211> LENGTH: 9
<212> TYPE: PRT
<213> ORGANISM: Artificial Sequence
<220> FEATURE:
<223> OTHER INFORMATION: Synthetic

<400> SEQUENCE: 4

Val Phe Ala Gly Lys Asn Thr Asp Leu
1               5

<210> SEQ ID NO 5
<211> LENGTH: 9
<212> TYPE: PRT
<213> ORGANISM: Artificial Sequence
<220> FEATURE:
<223> OTHER INFORMATION: Synthetic

<400> SEQUENCE: 5

Leu Tyr Arg Lys Leu Lys Arg Glu Ile
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic

<400> SEQUENCE: 6

Thr Tyr Gln Arg Thr Arg Ala Leu Val
```

```
<210> SEQ ID NO 7
<211> LENGTH: 19
<212> TYPE: PRT
<213> ORGANISM: Artificial Sequence
<220> FEATURE:
<223> OTHER INFORMATION: Synthetic

<400> SEQUENCE: 7

Met Ala Ser Gln Gly Thr Lys Arg Ser Tyr Glu Gln Met Glu Thr Asp
1               5                   10                  15

Gly Asp Arg

<210> SEQ ID NO 8
<211> LENGTH: 20
<212> TYPE: PRT
<213> ORGANISM: Artificial Sequence
<220> FEATURE:
<223> OTHER INFORMATION: Synthetic

<400> SEQUENCE: 8

Tyr Glu Gln Met Glu Thr Asp Gly Asp Arg Gln Asn Ala Thr Glu Ile
1               5                   10                  15

Arg Ala Ser Val
            20

<210> SEQ ID NO 9
<211> LENGTH: 20
<212> TYPE: PRT
<213> ORGANISM: Artificial Sequence
<220> FEATURE:
<223> OTHER INFORMATION: Synthetic

<400> SEQUENCE: 9

Arg Gln Asn Ala Thr Glu Ile Arg Ala Ser Val Gly Lys Met Ile Asp
1               5                   10                  15

Gly Ile Gly Arg
            20

<210> SEQ ID NO 10
<211> LENGTH: 20
<212> TYPE: PRT
<213> ORGANISM: Artificial Sequence
<220> FEATURE:
<223> OTHER INFORMATION: Synthetic

<400> SEQUENCE: 10

Val Gly Lys Met Ile Asp Gly Ile Gly Arg Phe Tyr Ile Gln Met Cys
1               5                   10                  15

Thr Glu Leu Lys
            20

<210> SEQ ID NO 11
<211> LENGTH: 19
<212> TYPE: PRT
<213> ORGANISM: Artificial Sequence
<220> FEATURE:
<223> OTHER INFORMATION: Synthetic

<400> SEQUENCE: 11

Phe Tyr Ile Gln Met Cys Thr Glu Leu Lys Leu Ser Asp Tyr Glu Gly
1               5                   10                  15

Arg Leu Ile
```

<210> SEQ ID NO 12
<211> LENGTH: 20
<212> TYPE: PRT
<213> ORGANISM: Artificial Sequence
<220> FEATURE:
<223> OTHER INFORMATION: Synthetic

<400> SEQUENCE: 12

Lys Leu Ser Asp Tyr Glu Gly Arg Leu Ile Gln Asn Ser Leu Thr Ile
1               5                   10                  15

Glu Lys Met Val
            20

<210> SEQ ID NO 13
<211> LENGTH: 19
<212> TYPE: PRT
<213> ORGANISM: Artificial Sequence
<220> FEATURE:
<223> OTHER INFORMATION: Synthetic

<400> SEQUENCE: 13

Ile Gln Asn Ser Leu Thr Ile Glu Lys Met Val Leu Ser Ala Phe Asp
1               5                   10                  15

Glu Arg Arg

<210> SEQ ID NO 14
<211> LENGTH: 20
<212> TYPE: PRT
<213> ORGANISM: Artificial Sequence
<220> FEATURE:
<223> OTHER INFORMATION: Synthetic

<400> SEQUENCE: 14

Met Val Leu Ser Ala Phe Asp Glu Arg Arg Asn Arg Tyr Leu Glu Glu
1               5                   10                  15

His Pro Ser Ala
            20

<210> SEQ ID NO 15
<211> LENGTH: 19
<212> TYPE: PRT
<213> ORGANISM: Artificial Sequence
<220> FEATURE:
<223> OTHER INFORMATION: Synthetic

<400> SEQUENCE: 15

Asn Arg Tyr Leu Glu Glu His Pro Ser Ala Gly Lys Asp Pro Lys Lys
1               5                   10                  15

Thr Gly Gly

<210> SEQ ID NO 16
<211> LENGTH: 20
<212> TYPE: PRT
<213> ORGANISM: Artificial Sequence
<220> FEATURE:
<223> OTHER INFORMATION: Synthetic

<400> SEQUENCE: 16

Ala Gly Lys Asp Pro Lys Lys Thr Gly Gly Pro Ile Tyr Arg Arg Val
1               5                   10                  15

Asp Gly Lys Trp
            20

```
<210> SEQ ID NO 17
<211> LENGTH: 19
<212> TYPE: PRT
<213> ORGANISM: Artificial Sequence
<220> FEATURE:
<223> OTHER INFORMATION: Synthetic

<400> SEQUENCE: 17

Pro Ile Tyr Arg Arg Val Asp Gly Lys Trp Met Arg Glu Leu Val Leu
1               5                   10                  15

Tyr Asp Lys

<210> SEQ ID NO 18
<211> LENGTH: 20
<212> TYPE: PRT
<213> ORGANISM: Artificial Sequence
<220> FEATURE:
<223> OTHER INFORMATION: Synthetic

<400> SEQUENCE: 18

Trp Met Arg Glu Leu Val Leu Tyr Asp Lys Glu Glu Ile Arg Arg Ile
1               5                   10                  15

Trp Arg Gln Ala
            20

<210> SEQ ID NO 19
<211> LENGTH: 20
<212> TYPE: PRT
<213> ORGANISM: Artificial Sequence
<220> FEATURE:
<223> OTHER INFORMATION: Synthetic

<400> SEQUENCE: 19

Glu Glu Ile Arg Arg Ile Trp Arg Gln Ala Asn Asn Gly Glu Asp Ala
1               5                   10                  15

Thr Ala Gly Leu
            20

<210> SEQ ID NO 20
<211> LENGTH: 20
<212> TYPE: PRT
<213> ORGANISM: Artificial Sequence
<220> FEATURE:
<223> OTHER INFORMATION: Synthetic

<400> SEQUENCE: 20

Asn Asn Gly Glu Asp Ala Thr Ala Gly Leu Thr His Met Met Ile Trp
1               5                   10                  15

His Ser Asn Leu
            20

<210> SEQ ID NO 21
<211> LENGTH: 20
<212> TYPE: PRT
<213> ORGANISM: Artificial Sequence
<220> FEATURE:
<223> OTHER INFORMATION: Synthetic

<400> SEQUENCE: 21

Thr His Met Met Ile Trp His Ser Asn Leu Asn Asp Thr Thr Tyr Gln
1               5                   10                  15

Arg Thr Arg Ala
            20
```

<210> SEQ ID NO 22
<211> LENGTH: 20
<212> TYPE: PRT
<213> ORGANISM: Artificial Sequence
<220> FEATURE:
<223> OTHER INFORMATION: Synthetic

<400> SEQUENCE: 22

Asn Asp Thr Thr Tyr Gln Arg Thr Arg Ala Leu Val Arg Thr Gly Met
1               5                   10                  15

Asp Pro Arg Met
            20

<210> SEQ ID NO 23
<211> LENGTH: 19
<212> TYPE: PRT
<213> ORGANISM: Artificial Sequence
<220> FEATURE:
<223> OTHER INFORMATION: Synthetic

<400> SEQUENCE: 23

Leu Val Arg Thr Gly Met Asp Pro Arg Met Cys Ser Leu Met Gln Gly
1               5                   10                  15

Ser Thr Leu

<210> SEQ ID NO 24
<211> LENGTH: 20
<212> TYPE: PRT
<213> ORGANISM: Artificial Sequence
<220> FEATURE:
<223> OTHER INFORMATION: Synthetic

<400> SEQUENCE: 24

Met Cys Ser Leu Met Gln Gly Ser Thr Leu Pro Arg Arg Ser Gly Ala
1               5                   10                  15

Ala Gly Ala Ala
            20

<210> SEQ ID NO 25
<211> LENGTH: 19
<212> TYPE: PRT
<213> ORGANISM: Artificial Sequence
<220> FEATURE:
<223> OTHER INFORMATION: Synthetic

<400> SEQUENCE: 25

Pro Arg Arg Ser Gly Ala Ala Gly Ala Ala Val Lys Gly Ile Gly Thr
1               5                   10                  15

Met Val Met

<210> SEQ ID NO 26
<211> LENGTH: 20
<212> TYPE: PRT
<213> ORGANISM: Artificial Sequence
<220> FEATURE:
<223> OTHER INFORMATION: Synthetic

<400> SEQUENCE: 26

Ala Val Lys Gly Ile Gly Thr Met Val Met Glu Leu Ile Arg Met Val
1               5                   10                  15

Lys Arg Gly Ile
            20

```
<210> SEQ ID NO 27
<211> LENGTH: 18
<212> TYPE: PRT
<213> ORGANISM: Artificial Sequence
<220> FEATURE:
<223> OTHER INFORMATION: Synthetic

<400> SEQUENCE: 27

Glu Leu Ile Arg Met Val Lys Arg Gly Ile Asn Asp Arg Asn Phe Trp
1               5                   10                  15

Arg Gly

<210> SEQ ID NO 28
<211> LENGTH: 20
<212> TYPE: PRT
<213> ORGANISM: Artificial Sequence
<220> FEATURE:
<223> OTHER INFORMATION: Synthetic

<400> SEQUENCE: 28

Gly Ile Asn Asp Arg Asn Phe Trp Arg Gly Glu Asn Gly Arg Lys Thr
1               5                   10                  15

Arg Ser Ala Tyr
            20

<210> SEQ ID NO 29
<211> LENGTH: 20
<212> TYPE: PRT
<213> ORGANISM: Artificial Sequence
<220> FEATURE:
<223> OTHER INFORMATION: Synthetic

<400> SEQUENCE: 29

Glu Asn Gly Arg Lys Thr Arg Ser Ala Tyr Glu Arg Met Cys Asn Ile
1               5                   10                  15

Leu Lys Gly Lys
            20

<210> SEQ ID NO 30
<211> LENGTH: 20
<212> TYPE: PRT
<213> ORGANISM: Artificial Sequence
<220> FEATURE:
<223> OTHER INFORMATION: Synthetic

<400> SEQUENCE: 30

Glu Arg Met Cys Asn Ile Leu Lys Gly Lys Phe Gln Thr Ala Ala Gln
1               5                   10                  15

Arg Ala Met Val
            20

<210> SEQ ID NO 31
<211> LENGTH: 20
<212> TYPE: PRT
<213> ORGANISM: Artificial Sequence
<220> FEATURE:
<223> OTHER INFORMATION: Synthetic

<400> SEQUENCE: 31

Phe Gln Thr Ala Ala Gln Arg Ala Met Val Asp Gln Val Arg Glu Ser
1               5                   10                  15

Arg Asn Pro Gly
            20
```

```
<210> SEQ ID NO 32
<211> LENGTH: 20
<212> TYPE: PRT
<213> ORGANISM: Artificial Sequence
<220> FEATURE:
<223> OTHER INFORMATION: Synthetic

<400> SEQUENCE: 32

Asp Gln Val Arg Glu Ser Arg Asn Pro Gly Asn Ala Glu Ile Glu Asp
1               5                   10                  15

Leu Ile Phe Leu
            20

<210> SEQ ID NO 33
<211> LENGTH: 19
<212> TYPE: PRT
<213> ORGANISM: Artificial Sequence
<220> FEATURE:
<223> OTHER INFORMATION: Synthetic

<400> SEQUENCE: 33

Asn Ala Glu Ile Glu Asp Leu Ile Phe Leu Ala Arg Ser Ala Leu Ile
1               5                   10                  15

Leu Arg Gly

<210> SEQ ID NO 34
<211> LENGTH: 20
<212> TYPE: PRT
<213> ORGANISM: Artificial Sequence
<220> FEATURE:
<223> OTHER INFORMATION: Synthetic

<400> SEQUENCE: 34

Leu Ala Arg Ser Ala Leu Ile Leu Arg Gly Ser Val Ala His Lys Ser
1               5                   10                  15

Cys Leu Pro Ala
            20

<210> SEQ ID NO 35
<211> LENGTH: 20
<212> TYPE: PRT
<213> ORGANISM: Artificial Sequence
<220> FEATURE:
<223> OTHER INFORMATION: Synthetic

<400> SEQUENCE: 35

Ser Val Ala His Lys Ser Cys Leu Pro Ala Cys Val Tyr Gly Pro Ala
1               5                   10                  15

Val Ser Ser Gly
            20

<210> SEQ ID NO 36
<211> LENGTH: 20
<212> TYPE: PRT
<213> ORGANISM: Artificial Sequence
<220> FEATURE:
<223> OTHER INFORMATION: Synthetic

<400> SEQUENCE: 36

Cys Val Tyr Gly Pro Ala Val Ser Ser Gly Tyr Asp Phe Glu Lys Glu
1               5                   10                  15

Gly Tyr Ser Leu
            20
```

<210> SEQ ID NO 37
<211> LENGTH: 19
<212> TYPE: PRT
<213> ORGANISM: Artificial Sequence
<220> FEATURE:
<223> OTHER INFORMATION: Synthetic

<400> SEQUENCE: 37

Tyr Asp Phe Glu Lys Glu Gly Tyr Ser Leu Val Gly Ile Asp Pro Phe
1               5                   10                  15
Lys Leu Leu

<210> SEQ ID NO 38
<211> LENGTH: 20
<212> TYPE: PRT
<213> ORGANISM: Artificial Sequence
<220> FEATURE:
<223> OTHER INFORMATION: Synthetic

<400> SEQUENCE: 38

Leu Val Gly Ile Asp Pro Phe Lys Leu Leu Gln Asn Ser Gln Val Tyr
1               5                   10                  15
Ser Leu Ile Arg
            20

<210> SEQ ID NO 39
<211> LENGTH: 19
<212> TYPE: PRT
<213> ORGANISM: Artificial Sequence
<220> FEATURE:
<223> OTHER INFORMATION: Synthetic

<400> SEQUENCE: 39

Leu Gln Asn Ser Gln Val Tyr Ser Leu Ile Arg Pro Asn Glu Asn Pro
1               5                   10                  15
Ala His Lys

<210> SEQ ID NO 40
<211> LENGTH: 19
<212> TYPE: PRT
<213> ORGANISM: Artificial Sequence
<220> FEATURE:
<223> OTHER INFORMATION: Synthetic

<400> SEQUENCE: 40

Ile Arg Pro Asn Glu Asn Pro Ala His Lys Ser Gln Leu Val Trp Met
1               5                   10                  15
Ala Cys His

<210> SEQ ID NO 41
<211> LENGTH: 20
<212> TYPE: PRT
<213> ORGANISM: Artificial Sequence
<220> FEATURE:
<223> OTHER INFORMATION: Synthetic

<400> SEQUENCE: 41

Lys Ser Gln Leu Val Trp Met Ala Cys His Ser Ala Ala Phe Glu Asp
1               5                   10                  15
Leu Arg Leu Leu
            20

<210> SEQ ID NO 42
<211> LENGTH: 18

```
<212> TYPE: PRT
<213> ORGANISM: Artificial Sequence
<220> FEATURE:
<223> OTHER INFORMATION: Synthetic

<400> SEQUENCE: 42

Ser Ala Ala Phe Glu Asp Leu Arg Leu Leu Ser Phe Ile Arg Gly Thr
1               5                   10                  15

Lys Val

<210> SEQ ID NO 43
<211> LENGTH: 20
<212> TYPE: PRT
<213> ORGANISM: Artificial Sequence
<220> FEATURE:
<223> OTHER INFORMATION: Synthetic

<400> SEQUENCE: 43

Leu Leu Ser Phe Ile Arg Gly Thr Lys Val Ser Pro Arg Gly Lys Leu
1               5                   10                  15

Ser Thr Arg Gly
            20

<210> SEQ ID NO 44
<211> LENGTH: 19
<212> TYPE: PRT
<213> ORGANISM: Artificial Sequence
<220> FEATURE:
<223> OTHER INFORMATION: Synthetic

<400> SEQUENCE: 44

Ser Pro Arg Gly Lys Leu Ser Thr Arg Gly Val Gln Ile Ala Ser Asn
1               5                   10                  15

Glu Asn Met

<210> SEQ ID NO 45
<211> LENGTH: 20
<212> TYPE: PRT
<213> ORGANISM: Artificial Sequence
<220> FEATURE:
<223> OTHER INFORMATION: Synthetic

<400> SEQUENCE: 45

Gly Val Gln Ile Ala Ser Asn Glu Asn Met Asp Asn Met Gly Ser Ser
1               5                   10                  15

Thr Leu Glu Leu
            20

<210> SEQ ID NO 46
<211> LENGTH: 20
<212> TYPE: PRT
<213> ORGANISM: Artificial Sequence
<220> FEATURE:
<223> OTHER INFORMATION: Synthetic

<400> SEQUENCE: 46

Asp Asn Met Gly Ser Ser Thr Leu Glu Leu Arg Ser Gly Tyr Trp Ala
1               5                   10                  15

Ile Arg Thr Arg
            20

<210> SEQ ID NO 47
<211> LENGTH: 20
<212> TYPE: PRT
```

```
<213> ORGANISM: Artificial Sequence
<220> FEATURE:
<223> OTHER INFORMATION: Synthetic

<400> SEQUENCE: 47

Arg Ser Gly Tyr Trp Ala Ile Arg Thr Arg Ser Gly Gly Asn Thr Asn
1               5                   10                  15

Gln Gln Arg Ala
            20

<210> SEQ ID NO 48
<211> LENGTH: 17
<212> TYPE: PRT
<213> ORGANISM: Artificial Sequence
<220> FEATURE:
<223> OTHER INFORMATION: Synthetic

<400> SEQUENCE: 48

Ser Gly Gly Asn Thr Asn Gln Gln Arg Ala Ser Ala Gly Gln Ile Ser
1               5                   10                  15

Val

<210> SEQ ID NO 49
<211> LENGTH: 20
<212> TYPE: PRT
<213> ORGANISM: Artificial Sequence
<220> FEATURE:
<223> OTHER INFORMATION: Synthetic

<400> SEQUENCE: 49

Asn Gln Gln Arg Ala Ser Ala Gly Gln Ile Ser Val Gln Pro Thr Phe
1               5                   10                  15

Ser Val Gln Arg
            20

<210> SEQ ID NO 50
<211> LENGTH: 20
<212> TYPE: PRT
<213> ORGANISM: Artificial Sequence
<220> FEATURE:
<223> OTHER INFORMATION: Synthetic

<400> SEQUENCE: 50

Ser Val Gln Pro Thr Phe Ser Val Gln Arg Asn Leu Pro Phe Glu Lys
1               5                   10                  15

Ser Thr Val Met
            20

<210> SEQ ID NO 51
<211> LENGTH: 20
<212> TYPE: PRT
<213> ORGANISM: Artificial Sequence
<220> FEATURE:
<223> OTHER INFORMATION: Synthetic

<400> SEQUENCE: 51

Asn Leu Pro Phe Glu Lys Ser Thr Val Met Ala Ala Phe Thr Gly Asn
1               5                   10                  15

Thr Glu Gly Arg
            20

<210> SEQ ID NO 52
<211> LENGTH: 20
<212> TYPE: PRT
```

```
<213> ORGANISM: Artificial Sequence
<220> FEATURE:
<223> OTHER INFORMATION: Synthetic

<400> SEQUENCE: 52

Ala Ala Phe Thr Gly Asn Thr Glu Gly Arg Thr Ser Asp Met Arg Ala
1               5                   10                  15

Glu Ile Ile Arg
            20

<210> SEQ ID NO 53
<211> LENGTH: 20
<212> TYPE: PRT
<213> ORGANISM: Artificial Sequence
<220> FEATURE:
<223> OTHER INFORMATION: Synthetic

<400> SEQUENCE: 53

Thr Ser Asp Met Arg Ala Glu Ile Ile Arg Met Met Glu Gly Ala Lys
1               5                   10                  15

Pro Glu Glu Val
            20

<210> SEQ ID NO 54
<211> LENGTH: 20
<212> TYPE: PRT
<213> ORGANISM: Artificial Sequence
<220> FEATURE:
<223> OTHER INFORMATION: Synthetic

<400> SEQUENCE: 54

Met Met Glu Gly Ala Lys Pro Glu Glu Val Ser Phe Arg Gly Arg Gly
1               5                   10                  15

Val Phe Glu Leu
            20

<210> SEQ ID NO 55
<211> LENGTH: 20
<212> TYPE: PRT
<213> ORGANISM: Artificial Sequence
<220> FEATURE:
<223> OTHER INFORMATION: Synthetic

<400> SEQUENCE: 55

Ser Phe Arg Gly Arg Gly Val Phe Glu Leu Ser Asp Glu Lys Ala Thr
1               5                   10                  15

Asn Pro Ile Val
            20

<210> SEQ ID NO 56
<211> LENGTH: 19
<212> TYPE: PRT
<213> ORGANISM: Artificial Sequence
<220> FEATURE:
<223> OTHER INFORMATION: Synthetic

<400> SEQUENCE: 56

Ser Asp Glu Lys Ala Thr Asn Pro Ile Val Pro Ser Phe Glu Met Ser
1               5                   10                  15

Asn Glu Gly

<210> SEQ ID NO 57
<211> LENGTH: 18
<212> TYPE: PRT
```

<213> ORGANISM: Artificial Sequence
<220> FEATURE:
<223> OTHER INFORMATION: Synthetic

<400> SEQUENCE: 57

Val Pro Ser Phe Glu Met Ser Asn Glu Gly Ser Tyr Phe Phe Gly Asp
1               5                   10                  15

Asn Ala

<210> SEQ ID NO 58
<211> LENGTH: 20
<212> TYPE: PRT
<213> ORGANISM: Artificial Sequence
<220> FEATURE:
<223> OTHER INFORMATION: Synthetic

<400> SEQUENCE: 58

Glu Gly Ser Tyr Phe Phe Gly Asp Asn Ala Glu Glu Tyr Asp Asn Gly
1               5                   10                  15

Gly Gly Pro Gly
            20

<210> SEQ ID NO 59
<211> LENGTH: 19
<212> TYPE: PRT
<213> ORGANISM: Artificial Sequence
<220> FEATURE:
<223> OTHER INFORMATION: Synthetic

<400> SEQUENCE: 59

Glu Glu Tyr Asp Asn Gly Gly Pro Gly Gly Gly Met Ser Leu Leu
1               5                   10                  15

Thr Glu Val

<210> SEQ ID NO 60
<211> LENGTH: 18
<212> TYPE: PRT
<213> ORGANISM: Artificial Sequence
<220> FEATURE:
<223> OTHER INFORMATION: Synthetic

<400> SEQUENCE: 60

Gly Gly Gly Met Ser Leu Leu Thr Glu Val Glu Thr Tyr Val Leu Ser
1               5                   10                  15

Ile Val

<210> SEQ ID NO 61
<211> LENGTH: 20
<212> TYPE: PRT
<213> ORGANISM: Artificial Sequence
<220> FEATURE:
<223> OTHER INFORMATION: Synthetic

<400> SEQUENCE: 61

Glu Val Glu Thr Tyr Val Leu Ser Ile Val Pro Ser Gly Pro Leu Lys
1               5                   10                  15

Ala Glu Ile Ala
            20

<210> SEQ ID NO 62
<211> LENGTH: 20
<212> TYPE: PRT
<213> ORGANISM: Artificial Sequence
<220> FEATURE:

-continued

<223> OTHER INFORMATION: Synthetic

<400> SEQUENCE: 62

Pro Ser Gly Pro Leu Lys Ala Glu Ile Ala Gln Arg Leu Glu Asp Val
1               5                   10                  15

Phe Ala Gly Lys
            20

<210> SEQ ID NO 63
<211> LENGTH: 19
<212> TYPE: PRT
<213> ORGANISM: Artificial Sequence
<220> FEATURE:
<223> OTHER INFORMATION: Synthetic

<400> SEQUENCE: 63

Ala Gln Arg Leu Glu Asp Val Phe Ala Gly Lys Asn Thr Asp Leu Glu
1               5                   10                  15

Ala Leu Met

<210> SEQ ID NO 64
<211> LENGTH: 19
<212> TYPE: PRT
<213> ORGANISM: Artificial Sequence
<220> FEATURE:
<223> OTHER INFORMATION: Synthetic

<400> SEQUENCE: 64

Gly Lys Asn Thr Asp Leu Glu Ala Leu Met Glu Trp Leu Lys Thr Arg
1               5                   10                  15

Pro Ile Leu

<210> SEQ ID NO 65
<211> LENGTH: 20
<212> TYPE: PRT
<213> ORGANISM: Artificial Sequence
<220> FEATURE:
<223> OTHER INFORMATION: Synthetic

<400> SEQUENCE: 65

Met Glu Trp Leu Lys Thr Arg Pro Ile Leu Ser Pro Leu Thr Lys Gly
1               5                   10                  15

Ile Leu Gly Phe
            20

<210> SEQ ID NO 66
<211> LENGTH: 20
<212> TYPE: PRT
<213> ORGANISM: Artificial Sequence
<220> FEATURE:
<223> OTHER INFORMATION: Synthetic

<400> SEQUENCE: 66

Ser Pro Leu Thr Lys Gly Ile Leu Gly Phe Val Phe Thr Leu Thr Val
1               5                   10                  15

Pro Ser Glu Arg
            20

<210> SEQ ID NO 67
<211> LENGTH: 18
<212> TYPE: PRT
<213> ORGANISM: Artificial Sequence
<220> FEATURE:
<223> OTHER INFORMATION: Synthetic

<400> SEQUENCE: 67

Val Phe Thr Leu Thr Val Pro Ser Glu Arg Gly Leu Gln Arg Arg
1               5                   10                  15

Phe Val

<210> SEQ ID NO 68
<211> LENGTH: 18
<212> TYPE: PRT
<213> ORGANISM: Artificial Sequence
<220> FEATURE:
<223> OTHER INFORMATION: Synthetic

<400> SEQUENCE: 68

Glu Arg Gly Leu Gln Arg Arg Phe Val Gln Asn Ala Leu Asn Gly
1               5                   10                  15

Asn Gly

<210> SEQ ID NO 69
<211> LENGTH: 20
<212> TYPE: PRT
<213> ORGANISM: Artificial Sequence
<220> FEATURE:
<223> OTHER INFORMATION: Synthetic

<400> SEQUENCE: 69

Phe Val Gln Asn Ala Leu Asn Gly Asn Gly Asp Pro Asn Asn Met Asp
1               5                   10                  15

Lys Ala Val Lys
            20

<210> SEQ ID NO 70
<211> LENGTH: 19
<212> TYPE: PRT
<213> ORGANISM: Artificial Sequence
<220> FEATURE:
<223> OTHER INFORMATION: Synthetic

<400> SEQUENCE: 70

Asp Pro Asn Asn Met Asp Lys Ala Val Lys Leu Tyr Arg Lys Leu Lys
1               5                   10                  15

Arg Glu Ile

<210> SEQ ID NO 71
<211> LENGTH: 20
<212> TYPE: PRT
<213> ORGANISM: Artificial Sequence
<220> FEATURE:
<223> OTHER INFORMATION: Synthetic

<400> SEQUENCE: 71

Lys Leu Tyr Arg Lys Leu Lys Arg Glu Ile Thr Phe His Gly Ala Lys
1               5                   10                  15

Glu Ile Ala Leu
            20

<210> SEQ ID NO 72
<211> LENGTH: 18
<212> TYPE: PRT
<213> ORGANISM: Artificial Sequence
<220> FEATURE:
<223> OTHER INFORMATION: Synthetic

<400> SEQUENCE: 72

Thr Phe His Gly Ala Lys Glu Ile Ala Leu Ser Tyr Ser Ala Gly Ala
1               5                   10                  15

Leu Ala

<210> SEQ ID NO 73
<211> LENGTH: 20
<212> TYPE: PRT
<213> ORGANISM: Artificial Sequence
<220> FEATURE:
<223> OTHER INFORMATION: Synthetic

<400> SEQUENCE: 73

Ala Leu Ser Tyr Ser Ala Gly Ala Leu Ala Ser Cys Met Gly Leu Ile
1               5                   10                  15

Tyr Asn Arg Met
            20

<210> SEQ ID NO 74
<211> LENGTH: 20
<212> TYPE: PRT
<213> ORGANISM: Artificial Sequence
<220> FEATURE:
<223> OTHER INFORMATION: Synthetic

<400> SEQUENCE: 74

Ser Cys Met Gly Leu Ile Tyr Asn Arg Met Gly Ala Val Thr Thr Glu
1               5                   10                  15

Val Ala Phe Gly
            20

<210> SEQ ID NO 75
<211> LENGTH: 20
<212> TYPE: PRT
<213> ORGANISM: Artificial Sequence
<220> FEATURE:
<223> OTHER INFORMATION: Synthetic

<400> SEQUENCE: 75

Gly Ala Val Thr Thr Glu Val Ala Phe Gly Leu Val Cys Ala Thr Cys
1               5                   10                  15

Glu Gln Ile Ala
            20

<210> SEQ ID NO 76
<211> LENGTH: 20
<212> TYPE: PRT
<213> ORGANISM: Artificial Sequence
<220> FEATURE:
<223> OTHER INFORMATION: Synthetic

<400> SEQUENCE: 76

Leu Val Cys Ala Thr Cys Glu Gln Ile Ala Asp Ser Gln His Arg Ser
1               5                   10                  15

His Arg Gln Met
            20

<210> SEQ ID NO 77
<211> LENGTH: 20
<212> TYPE: PRT
<213> ORGANISM: Artificial Sequence
<220> FEATURE:
<223> OTHER INFORMATION: Synthetic

<400> SEQUENCE: 77

```
Asp Ser Gln His Arg Ser His Arg Gln Met Val Ala Thr Thr Asn Pro
1               5                   10                  15

Leu Ile Lys His
            20

<210> SEQ ID NO 78
<211> LENGTH: 17
<212> TYPE: PRT
<213> ORGANISM: Artificial Sequence
<220> FEATURE:
<223> OTHER INFORMATION: Synthetic

<400> SEQUENCE: 78

Val Ala Thr Thr Asn Pro Leu Ile Lys His Glu Asn Arg Met Val Leu
1               5                   10                  15

Ala

<210> SEQ ID NO 79
<211> LENGTH: 20
<212> TYPE: PRT
<213> ORGANISM: Artificial Sequence
<220> FEATURE:
<223> OTHER INFORMATION: Synthetic

<400> SEQUENCE: 79

Ile Lys His Glu Asn Arg Met Val Leu Ala Ser Thr Thr Ala Lys Ala
1               5                   10                  15

Met Glu Gln Met
            20

<210> SEQ ID NO 80
<211> LENGTH: 20
<212> TYPE: PRT
<213> ORGANISM: Artificial Sequence
<220> FEATURE:
<223> OTHER INFORMATION: Synthetic

<400> SEQUENCE: 80

Ser Thr Thr Ala Lys Ala Met Glu Gln Met Ala Gly Ser Ser Glu Gln
1               5                   10                  15

Ala Ala Glu Ala
            20

<210> SEQ ID NO 81
<211> LENGTH: 20
<212> TYPE: PRT
<213> ORGANISM: Artificial Sequence
<220> FEATURE:
<223> OTHER INFORMATION: Synthetic

<400> SEQUENCE: 81

Ala Gly Ser Ser Glu Gln Ala Ala Glu Ala Met Glu Ile Ala Ser Gln
1               5                   10                  15

Ala Arg Gln Met
            20

<210> SEQ ID NO 82
<211> LENGTH: 20
<212> TYPE: PRT
<213> ORGANISM: Artificial Sequence
<220> FEATURE:
<223> OTHER INFORMATION: Synthetic

<400> SEQUENCE: 82
```

```
Met Glu Ile Ala Ser Gln Ala Arg Gln Met Val Gln Ala Met Arg Thr
1               5                  10                 15

Val Gly Thr His
            20

<210> SEQ ID NO 83
<211> LENGTH: 18
<212> TYPE: PRT
<213> ORGANISM: Artificial Sequence
<220> FEATURE:
<223> OTHER INFORMATION: Synthetic

<400> SEQUENCE: 83

Val Gln Ala Met Arg Thr Val Gly Thr His Pro Ser Ser Thr Gly
1               5                  10                 15

Leu Arg

<210> SEQ ID NO 84
<211> LENGTH: 20
<212> TYPE: PRT
<213> ORGANISM: Artificial Sequence
<220> FEATURE:
<223> OTHER INFORMATION: Synthetic

<400> SEQUENCE: 84

Thr His Pro Ser Ser Ser Thr Gly Leu Arg Asp Asp Leu Leu Glu Asn
1               5                  10                 15

Leu Gln Thr Tyr
            20

<210> SEQ ID NO 85
<211> LENGTH: 20
<212> TYPE: PRT
<213> ORGANISM: Artificial Sequence
<220> FEATURE:
<223> OTHER INFORMATION: Synthetic

<400> SEQUENCE: 85

Asp Asp Leu Leu Glu Asn Leu Gln Thr Tyr Gln Lys Arg Met Gly Val
1               5                  10                 15

Gln Met Gln Arg
            20

<210> SEQ ID NO 86
<211> LENGTH: 12
<212> TYPE: PRT
<213> ORGANISM: Artificial Sequence
<220> FEATURE:
<223> OTHER INFORMATION: Synthetic

<400> SEQUENCE: 86

Gln Lys Arg Met Gly Val Gln Met Gln Arg Phe Lys
1               5                  10
```

COMPOSITIONS AND METHODS

RELATED APPLICATIONS

The present application is filed as a divisional application of U.S. patent application Ser. No. 12/239,969, which was filed Sep. 29, 2008, claiming the benefit of priority to British Patent Application No. 0719526.6, which was filed on Oct. 5, 2007, European Patent Application No. 07255070.0, which was filed Dec. 28, 2007, and British Patent Application No. 0816534.2, which was filed Sep. 10, 2008. The entire text of the aforementioned applications is incorporated herein by reference in its entirety.

This application incorporates by reference a Sequence Listing submitted in computer readable form (CRF) as a text file entitled "19996US02_SUBSTSeqListing" created on Jun. 17, 2016 and having a size of 32,934 bytes.

FIELD OF THE INVENTION

The invention relates to compositions and methods for inducing an immune response against influenza, in particular a T cell mediated immune response.

BACKGROUND TO THE INVENTION

Influenza vaccination strategies have been relatively constant for at least about 20 years. Typically, each vaccine comprises inactivated flu virus particles from approximately three different strains. These vaccines are given in order to induce antibody based responses. Each year, the World Health Organisation (WHO) selects the strains which it considers to pose the greatest threat to human health at that time. Two decisions per year are typically issued, one for Northern hemisphere strains and one for Southern hemisphere strains. Following the announcement, manufacturers then have a short period of time in order to make that year's vaccine formulations. This strategy leads to a number of problems. Firstly, due to the short manufacturing window, complications in production can arise. Delays can occur in the system, for example when particular strains are unavailable or when substitutions need to be made. Moreover, higher level problems are presented by this strategy. For example, this strategy effectively represents a statistical gamble on the particular serotypes of influenza which might pose the greatest threat to human health. However, the various populations of flu viruses change dynamically with time. Therefore, the lag between choice of strains and vaccination following manufacture can mean that the vaccine formulations may no longer represent the optimal formulations even at the time of administration. In addition, shortages of the vaccine are very common. The reason is that manufacturers are unable to sell excess aliquots of vaccine since the vaccine formulation is updated each year and there is no market for the previous year's composition. This reason alone means that the whole population cannot be vaccinated. Vaccinations tend to be focussed on perceived risk groups. One such risk group is the elderly. However, this strategy itself may be flawed since studies comparing the effects of vaccinating the elderly subjects at risk with the effects of vaccinating the same subjects together with each individual with whom they have contact demonstrate that in order to be effective, those individuals with whom the at risk patients come into contact need to be vaccinated in order for the strategy to be effective.

In addition to the above, the biology of influenza viruses means that the external proteins of the virus change over time. This is part of the natural host defence evasion behaviour of the virus. Furthermore, new serotypes come into humans from other species, such as from avian species, for example by re-assortment or other genetic mechanisms. This again leads to serotypes with different external proteins. Clearly, with the external proteins of the virus continually changing, the hopes of a conventional vaccine design remaining effective from year to year are remote. Current vaccines for influenza A act by stimulating production of antibodies to haemagglutinin (HA) and neuraminidase (NA). As these proteins are highly polymorphic, there is very little or no cross-subtype (or heterosubtypic) protection and limited cross-strain protection even within subtypes. As noted above, there is a need for constant redesign and remanufacture which increases the cost of the vaccines, places limitations on supply, and most importantly means that vaccines for newly arising strains can only be produced once the HA and NA sequences of viruses posing the greatest threat to human health have been identified. Avian influenza in humans is currently treated with the anti-viral drug oseltamivir, and this drug is now being stockpiled for use in future pandemics. However, oseltamivir resistant H5N1 virus has now been isolated following human infection, so the use of this drug alone may not be sufficient to treat infected individuals or limit the spread of the virus should it become transmissible from human to human. From the 59 known human cases of H5N1 influenza it is striking that the majority of infections have been found in young people, and that the case fatality rate among those less than 15 years of age was 89%.

Natural infection with influenza virus results in T cell responses to NP and M1, but subunit vaccines consisting of HA and NA cannot induce these responses. A cold-adapted (ca), live-attenuated virus vaccine for intranasal immunisation has now been licensed in Russia and the USA. Vaccines produced in this way have been shown to induce some cross-protective immunity. Trials were carried out in sero-negative children vaccinated with a ca virus. The level of seroconversion to the vaccine strain ranged from 41 to 89%, with the level of seroconversion to different strains ranging from 5 to 55%. The cross-reactivity is therefore low, and as with subunit vaccines, a new mix of virus strains is used to produce a vaccine for each year. Further, safety concerns related to vaccine strain shedding have resulted in this vaccine being approved only for the age-group 5-49 in the USA. This excludes two major risk groups who are older or younger than the defined age range, as well as immunodeficient patients and pregnant women. The risk of a major global pandemic of avian influenza has created widespread and justified concern. Vaccination presents a potential control measure but there is no vaccine licensed against H5N1 influenza and recent trials of new investigational H5N1 vaccines suggested that a 12 fold greater amount of antigen would be need per vaccine course than with other flu vaccines. This has discouraged further development of vaccines due to the manufacturing parties being concerned that if a pandemic does not occur they will be left with unsold supplies. Other attempts to solve these problems have focussed on the use of adjuvants to reduce the amount of antigen needed. Moreover, the current high rate of diversification of H5N1 strains suggests that vaccines made now may differ so much in their H5 sequence from any pandemic strain that emerges that these vaccines would have little or no efficacy.

Mice immunised with DNA vaccines expressing nucleoprotein (NP) and matrix (M1) from H1N1 virus have been shown to be protected against lethal challenge with an H5N1 strain (Kreijtz et al 2007 Journal of Infectious Diseases vole 195 p. 1598). Using a DNA prime/adenovirus boost regime with vaccines expressing NP, T cell dependent protection against numerous influenza A subtypes including H5N1 has been demonstrated in mice. However, in humans DNA vaccines are not good immunogens and do not boost pre-existing responses. Recombinant MVA expressing HA or NP from equine influenza administered with or without a DNA vaccine prime has recently been shown to induce antibodies, lymphoproliferation and interferon gamma production in ponies (Breathnach et al 2004 Veterinary Immunology and Immunopathology vol 98 pp 127-136) However, two booster doses of MVA were used, no challenge studies are disclosed and no efficacy was demonstrated.

The invention seeks to overcome problem(s) associated with the prior art.

SUMMARY OF THE INVENTION

The prior art has been concerned with generation of antibody responses against influenza virus. These prior art approaches have been logically based on targeting the external antigens of the virus particles. However, those external antigens constantly change over time through phenomena such as antigenic shift, antigenic drift, and introduction of new serotypes for example by re-assortment based mechanisms. Therefore, prior art based approaches typically fail to generate protective cross reactivity from strain to strain. Furthermore, due to the limited number of strains which can be included in any particular given vaccine, at best the protection conferred omits large numbers of potentially threatening viruses. In addition, lags between the selection of the potentially most threatening strains in any given year and the manufacture of the corresponding vaccine mean that vaccine designers are constantly struggling to keep up as changes in the viral populations will have taken place even before the chosen vaccines are manufactured and administered.

By contrast to the prior art approaches, the present inventors have focussed on the generation of cell based immunity. In addition to choosing a cell based immunity approach, the present inventors teach that internal proteins from influenza virus should be used as vaccine components. A priori, such approaches would not be expected to work. One reason is that by choosing internal antigens, it is more difficult to target the virus since those antigens would often be "buried" or masked by the rest of the virus structure. More importantly, it is not expected that cell based immunity would effectively address influenza pathogenicity. The reason is that, in contrast to antibody based approaches, T cells do not attack free virus such as virus in the bloodstream or upper respiratory tract. T cell mediated immunity relies on the immune cells attacking cells in the subject which are actually infected with virus. Therefore, at best it might be hoped that a cell based approach might lead to a reduction in severity of a particular infection, but would not be expected to prevent or ameliorate the disease or infection itself. However, it is surprisingly shown by the present inventors that both these and other expected drawbacks with an approach involving internal antigens and cell based immunity are successfully overcome and an extremely effective vaccine is produced.

The present invention is based upon these surprising findings.

Thus, in one aspect the invention provides a composition suitable for inducing a T cell mediated immune response against an influenza virus in a vertebrate, said composition comprising nucleic acid encoding one or more epitopes of one or more internal proteins of influenza virus.

Suitably said composition comprises nucleic acid encoding at least two said epitopes, at least one epitope being from each of two or more internal proteins of influenza virus.

Thus, the invention suitably provides a composition suitable for inducing a T cell mediated immune response against an influenza virus in a vertebrate, said composition comprising nucleic acid encoding one or more epitopes of one or more internal proteins of influenza virus, wherein said composition comprises nucleic acid encoding at least two said epitopes, at least one epitope being from each of two or more internal proteins of influenza virus.

Suitably said internal proteins comprise nucleoprotein and matrix 1 protein.

Suitably said epitopes are provided in the form of a nucleoprotein-matrix 1 protein fusion.

Suitably said proteins are arranged in the order N terminus-nucleoprotein-matrix1 protein-C terminus.

Suitably said nucleoprotein and matrix 1 proteins are separated by a linker sequence.

Suitably said linker sequence has the amino acid sequence GGGPGGG (SEQ ID NO. 3).

Suitably said internal proteins are from the H3N2 influenza strain.

Suitably said internal proteins are from the H3N2 influenza strain subtype A/Panama/2007/99.

Suitably the coding sequence of the nucleic acid sequence encoding said internal proteins and/or linker polypeptides has been codon optimised for human codon usage.

Suitably said epitopes are provided in the form of a polypeptide comprising the amino acid sequence of SEQ ID NO:1.

Suitably said epitopes are encoded by a nucleic acid comprising the nucleotide sequence of SEQ ID NO:2.

Suitably said coding sequence is present in an adenovirus based vector.

Suitably said coding sequence is present in a MVA based vector.

Suitably said coding sequence is present in an avipox or orthopox based vector.

Suitably said composition may further comprise adjuvant.

Suitably said composition induces (or is capable of inducing once administered) T cell responses to both the NP and M1 antigens. Suitably this means inducing a T cell response to at least one NP epitope and to at least one M1 epitope. Suitably said responses are in a vertebrate. Most suitably said responses are in a primate.

In another aspect, the invention relates to use of a composition as described above in medicine.

In another aspect, the invention relates to use of a composition as described above in the preparation of a medicament for influenza.

In another aspect, the invention relates to a composition as described above for treatment of influenza.

In another aspect, the invention relates to a method for inducing an immune response in a subject, said method comprising administering to said subject a composition as described above.

In another aspect, the invention relates to a method as described above comprising administering a first composition comprising an adenovirus based vector and a second composition comprising a MVA based vector.

Suitably said subject is a primate or avian species. Suitably said subject is a primate such as a human.

BRIEF DESCRIPTION OF THE FIGURES

Figure 1A:
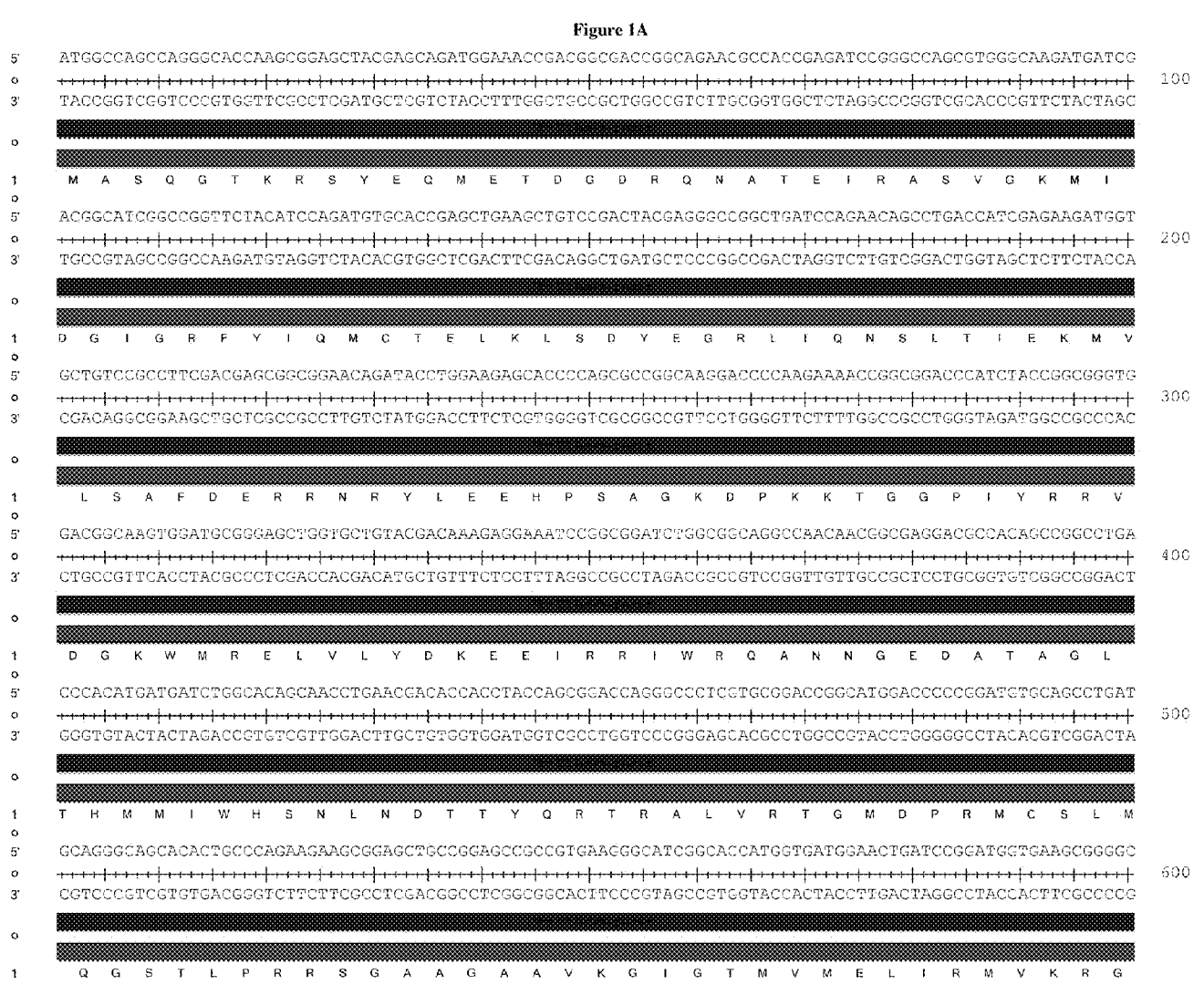
Figure 1B:
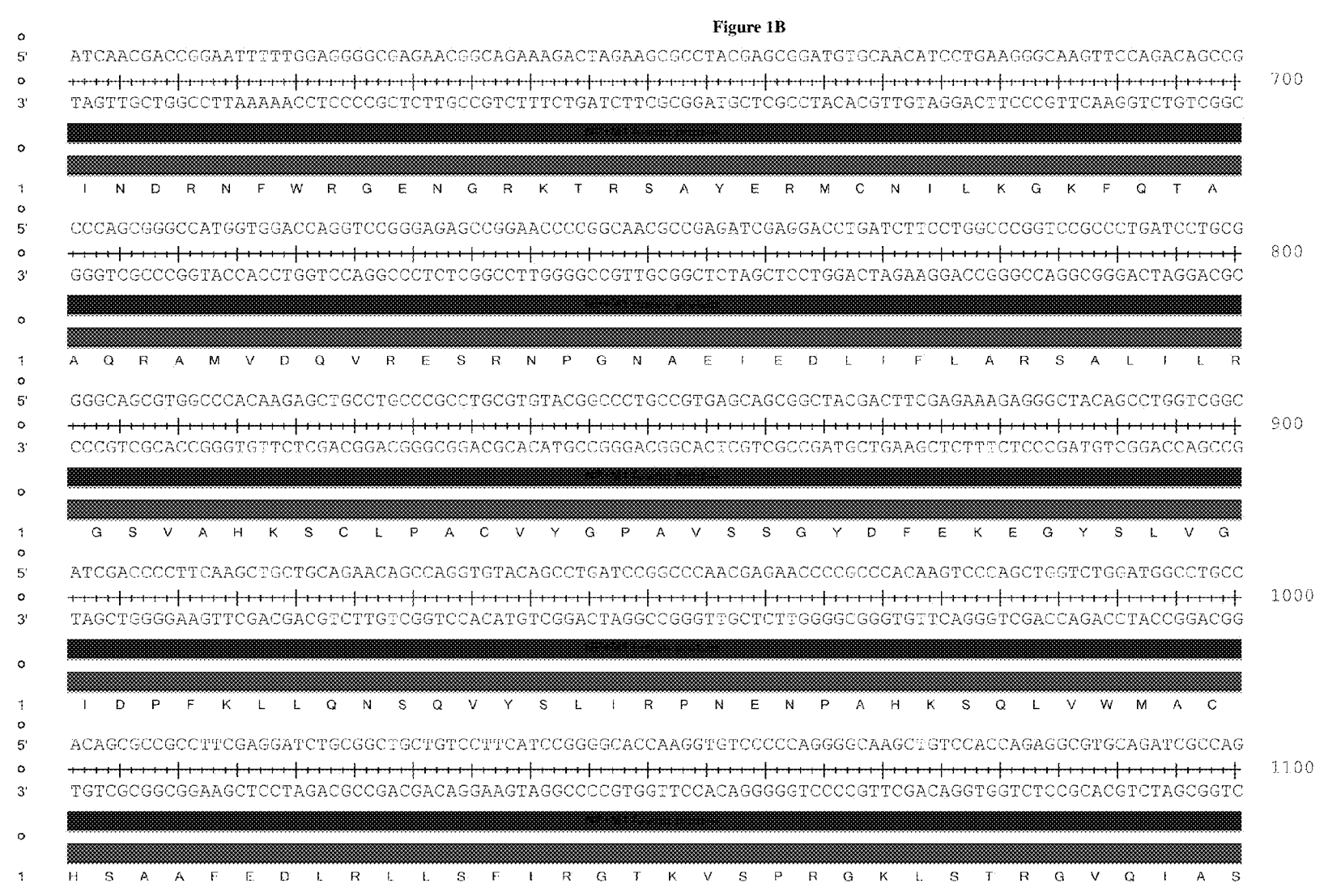
Figure 1C:
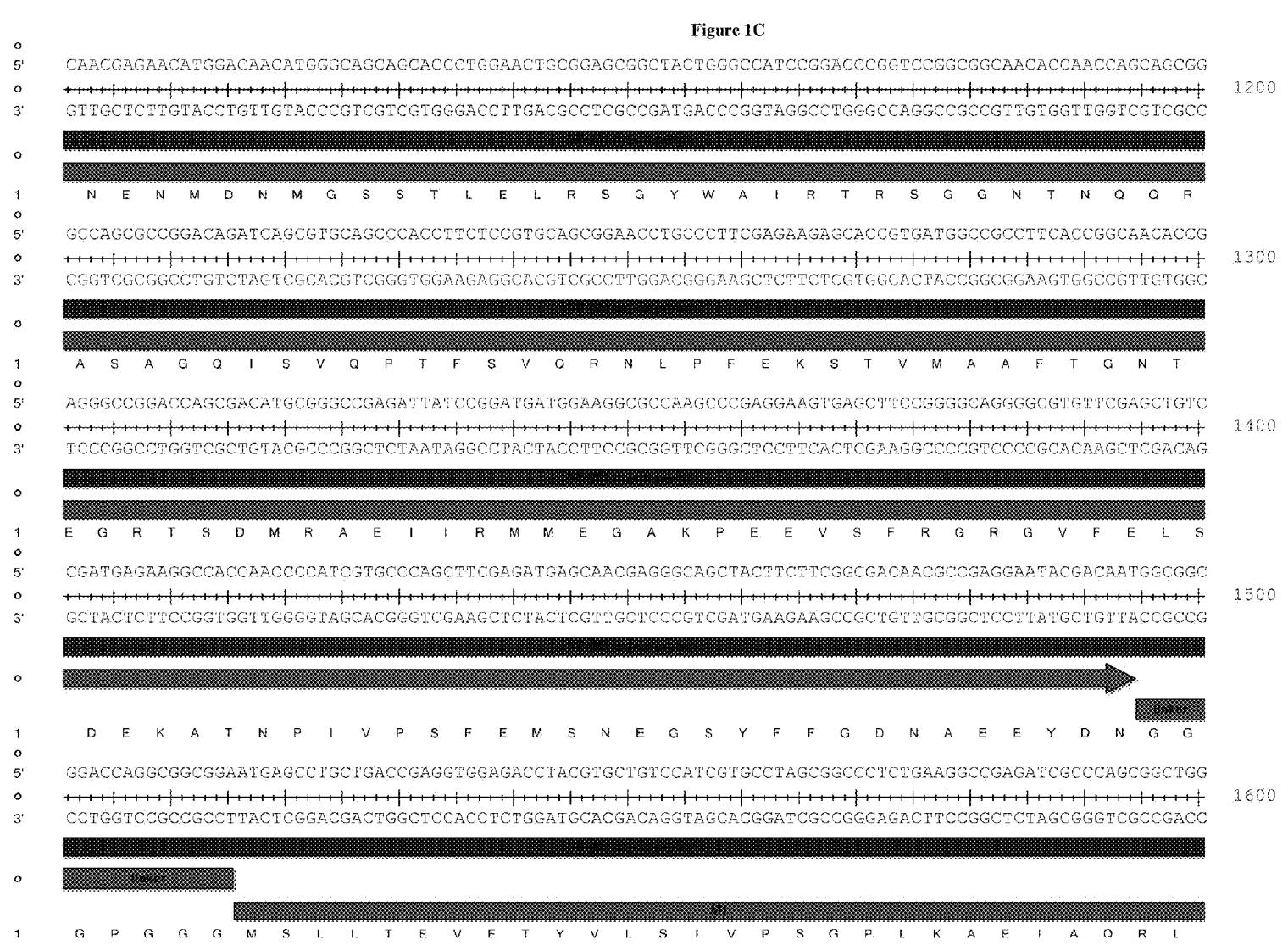
Figure 1D:
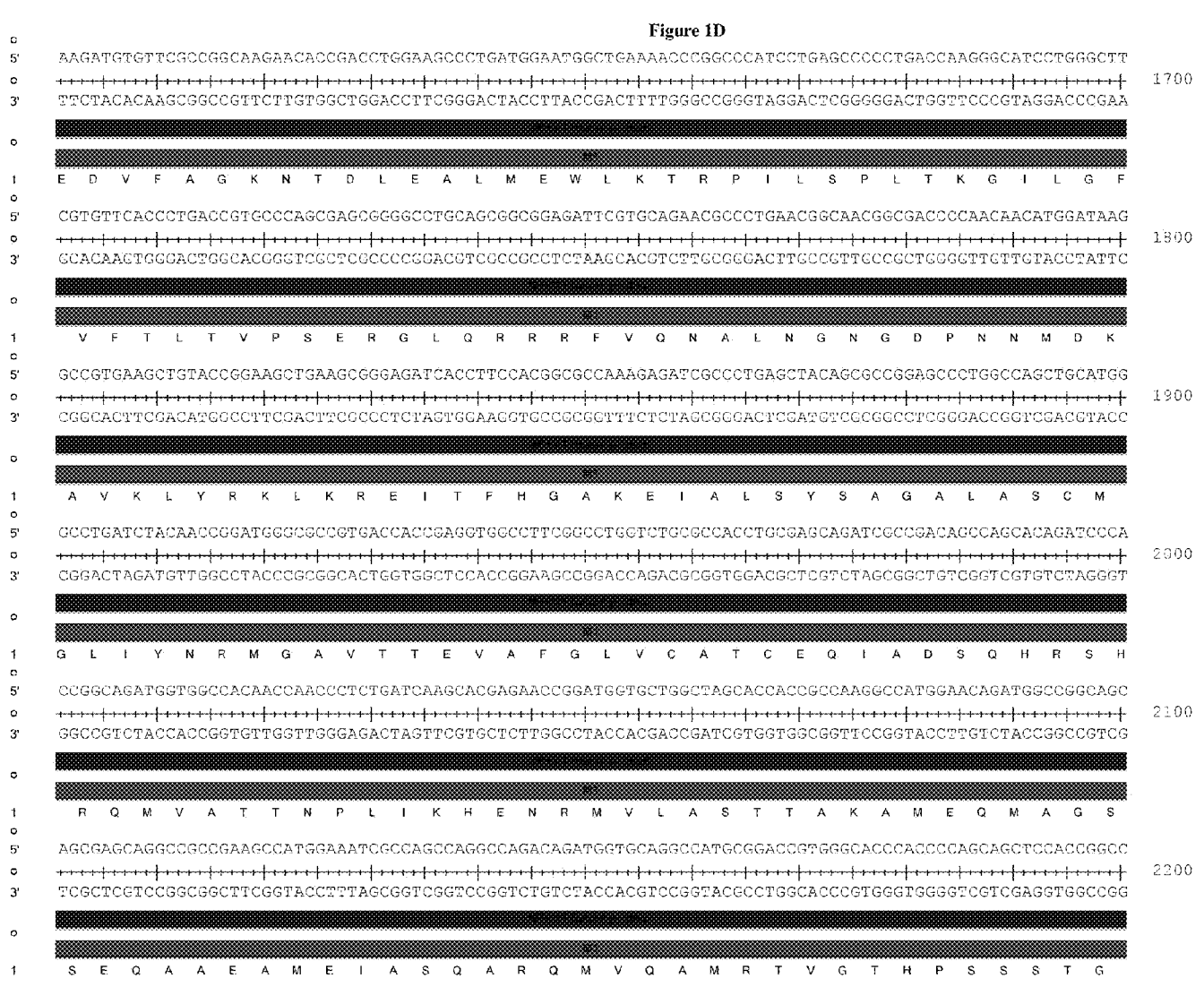

FIGS. 1A-1D show nucleotide sequence of SEQ ID NO:2, which nucleotide sequence encodes the A/Panama/2007/99 amino acid sequence of SEQ ID NO:1. The nucleic acid sequence has been optimised for human codon usage. The structure is nucleoprotein (NP) followed by linker (amino acid sequence gggpggg) followed by matrix 1 (M1).

Figure 2:
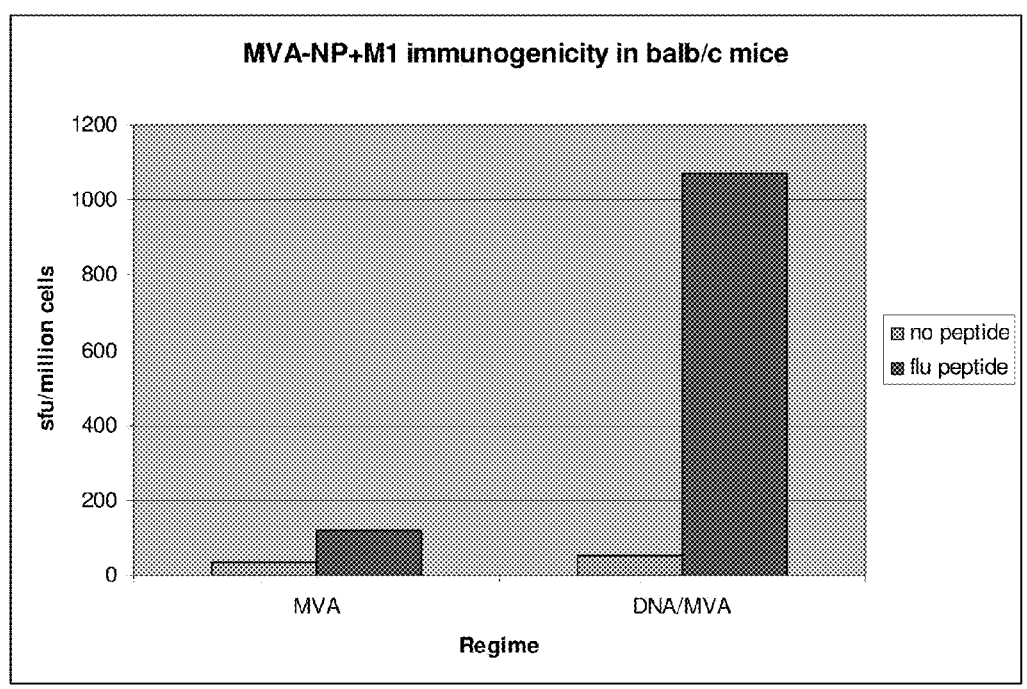
Figure 3:
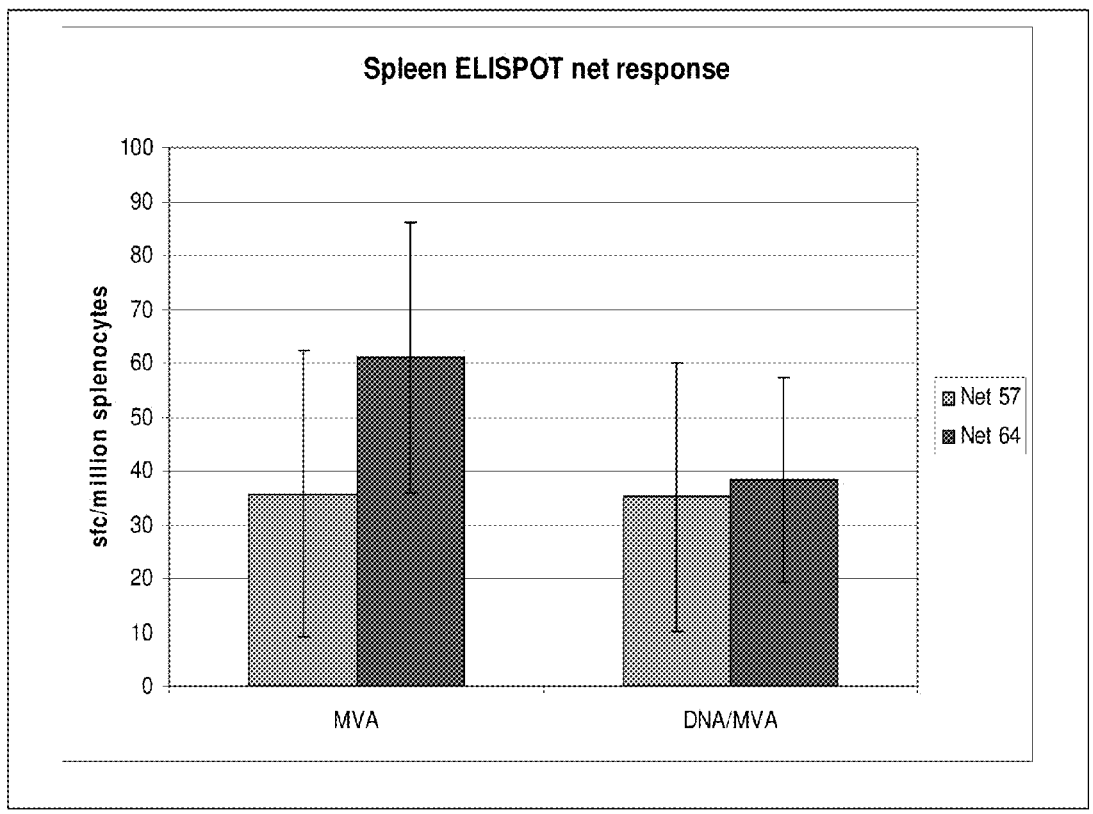

FIGS. 2 and 3 show bar charts of immunogenicity of MVA-NP+M1 in mice.

FIG. 2 shows immunogenicity of the NP region of the NP+M1 fusion.

FIG. 3 shows the immunogenicity of two epitopes, peptides 57 and 64, in the M1 coding sequence, which surprisingly also induces a T cell response despite being fused to the C terminus of the NP coding sequence by a non-natural linker sequence.

FIG. 4 shows a flowchart of FDP process for producing Adenovirus vectors.

FIG. 5 shows a photograph of visualised PCR products.

Figure 6:
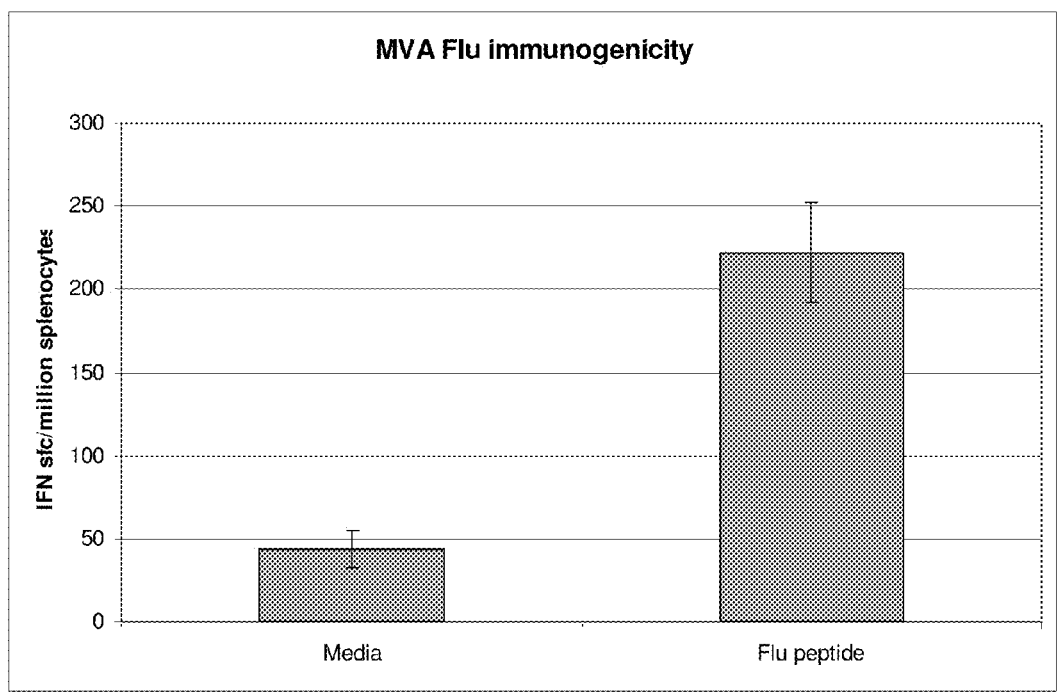

FIG. 6 shows a bar chart of immune response.

Figure 7:
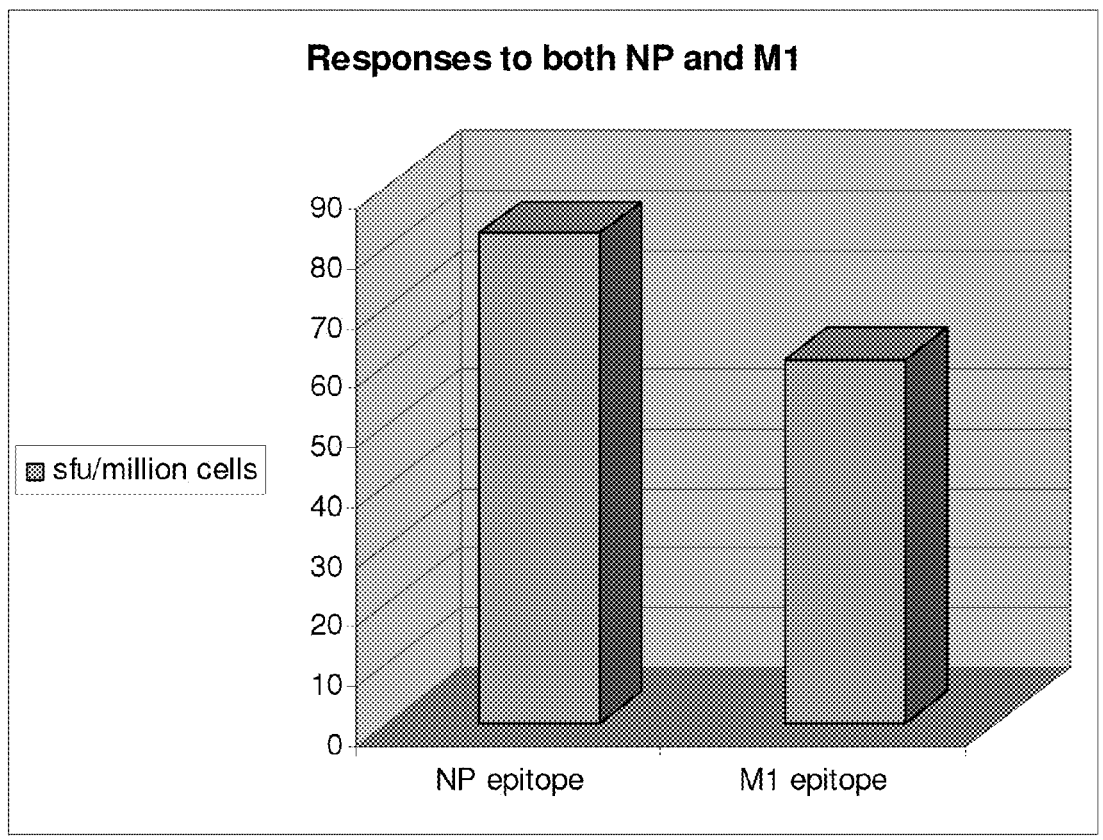

FIG. 7 shows a bar chart of immune response.

Figure 8A:
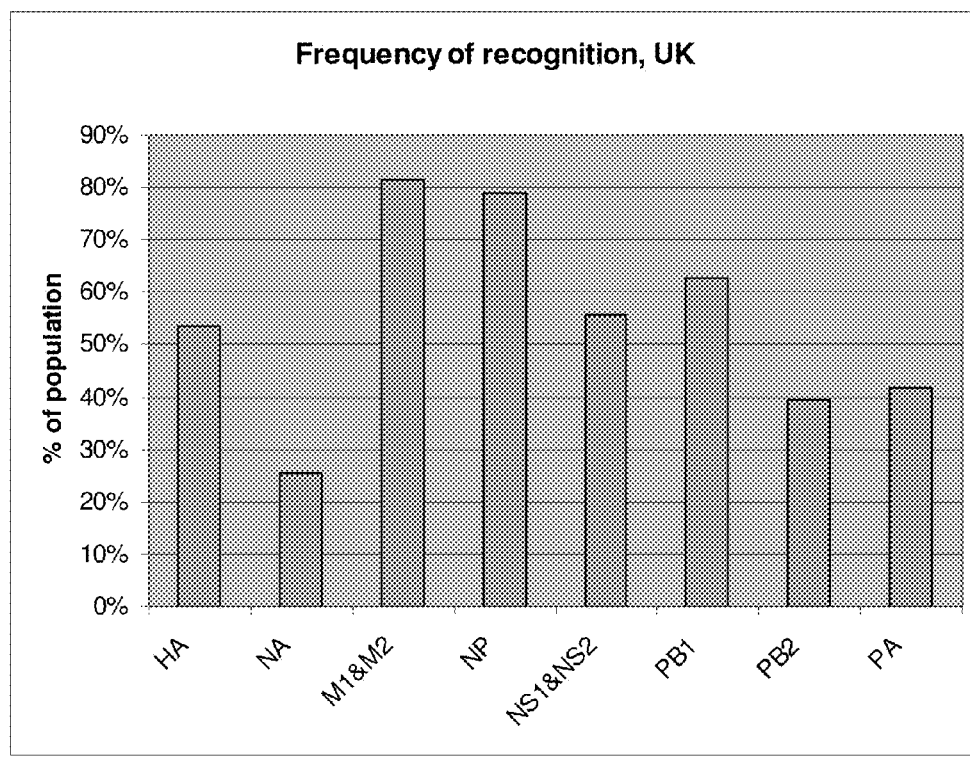
Figure 8B:
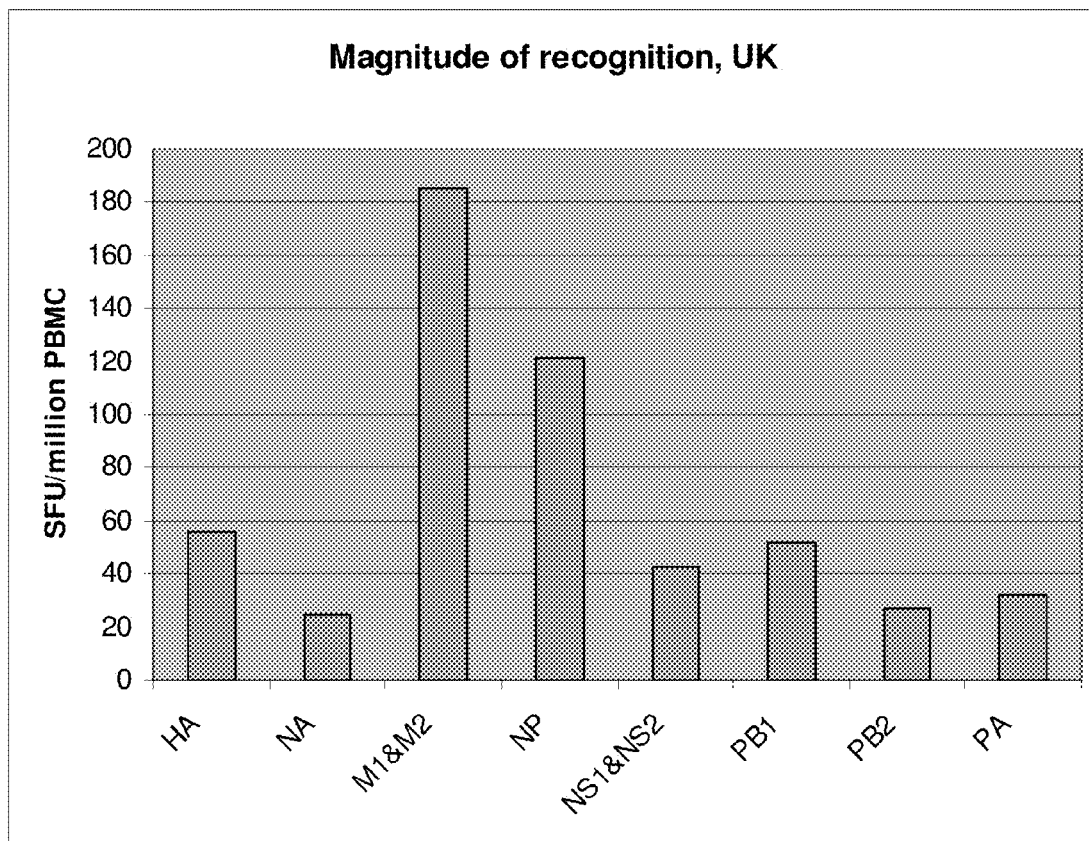

FIGS. 8A-8B show two bar charts.

FIGS. 9-13 and 14A-14B show bar charts.

FIGS. 15A-15D show bar charts of safety data.

FIGS. 16 to 22 show graphs of immunogenicity data for human subjects.

FIGS. 23 to 29 show graphs of immunogenicity data for human subjects.

Figure 30:
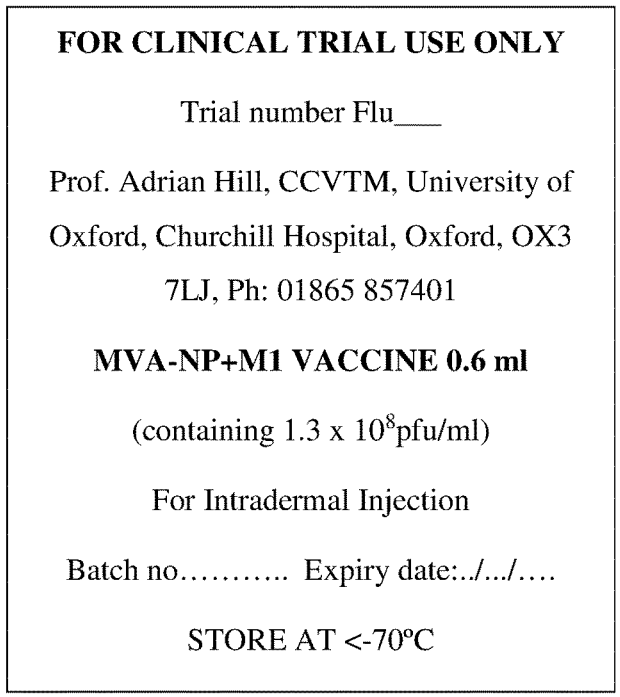

FIG. 30 shows a box label for a vaccine.

Figure 31:
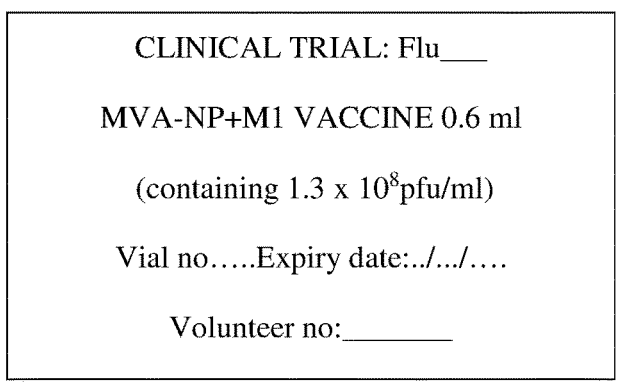

FIG. 31 shows a vial label for a vaccine.

DETAILED DESCRIPTION OF THE INVENTION

Definitions

A particular strain of influenza virus may be subject to antigenic drift and/or to antigenic shift. The effect of either of these phenomena is to alter the various antigens displayed by that virus. In particular, antigenic drift refers to the situation where single point mutations or other minor genetic alterations take place in the coding sequence for those antigens. By contrast, antigenic shift refers to the re-assortment of one or more of the eight RNA molecules which collectively make up the influenza virus genome. This tends to lead to a more dramatic or wholesale swapping or shifting of antigens than the more minor effects mediated by antigenic drift. It is important to note that within a particular strain, many individual variants may be observed.

It is an advantage of the invention that by providing excellent cross reactivity, each variant within a particular strain is embraced by the resulting immune response. This advantage flows from the use of conserved antigens, such as NP and/or M1.

The immune response induced may be easily characterised according to techniques known in the art. For example, the exact peptide(s) used in the immunisation can be employed in assessing the immune response. Alternatively, other strains such as closely related strains or variants of the strain upon which the antigens were based can be used in order to assess cross reactivity or the breadth of coverage provided by the immunisation.

In one embodiment, the antigens used comprise (eg. consist of) or are derived from the sequence of those antigens in the H3N2 strain. This embodiment has several advantages, such as the availability of the H3N2 virus as a GMP stock for challenge experiments. Furthermore, this strain is the commonest human influenza strain. This strain was first isolated in 1999, and is therefore an advantageously recent isolate.

The term 'derived from' has its natural meaning in the art. In other words, it means that the epitope or antigen is based on or taken from the source material which it is 'derived from'. This may be via cloning and direct nucleic acid manipulation from the source material, or is more likely to involve derivation from the nucleotide or amino acid sequence of the source material. In such an embodiment, the epitope or antigen is 'derived from' the source material if it shares sufficient sequence identity with the source material eg. if it shares at least 60% sequence identity at the amino acid level over at least 10 contiguous amino acids, suitably at least 70% sequence identity at the amino acid level, suitably at least 80% sequence identity at the amino acid level, suitably at least 90% sequence identity at the amino acid level, suitably at least 95% sequence identity at the amino acid level, suitably at least 98% sequence identity at the amino acid level, suitably at least 99% sequence identity at the amino acid level, suitably at least 100% sequence identity at the amino acid level. Suitably this is judged over at least 10 contiguous amino acids, suitably at least 20 amino acids, suitably at least 40 amino acids, suitably at least 60 amino acids, suitably at least 80 amino acids, suitably at least 100 amino acids, suitably at least 150 amino acids, suitably at least 200 amino acids, suitably at least 300 amino acids, suitably over the full length of the sequence of interest. For nucleic acids, the same criteria apply to nucleotide identity and contiguous nucleotide stretches. Suitably degeneracy of the genetic code may be taken into account accordingly.

It is an advantage of the invention that the antigens used, such as internal antigens, are much more conserved than external protein antigens. This has the beneficial effect that the year to year effectiveness of such a vaccine is significantly higher than a vaccine based on external antigens.

The terms 'internal' and 'external' antigens have their normal meaning in the art. Briefly, these refer to the locations of the antigens in/on the structure of the wild type virus. An internal antigen is typically in the viral core or matrix. An external antigen is one which is at least partially exposed at the surface of the viral particle, such as a surface available or surface accessible antigen. External antigens are typically used to try to generate antibody based responses. Preferably the invention excludes the use of external antigens. Suitably the antigens or epitopes of the invention are internal antigens or epitopes.

Suitably external antigens or epitopes are specifically excluded from the compositions of the invention. Suitably the nucleic acid(s) of the invention do not encode external antigen(s) or epitope(s). Suitably the nucleic acid(s) of the invention do not encode external protein(s) of influenza virus.

It is an advantage of the invention that the vaccine components need not be changed or altered year to year. Prior art external antigen based vaccines require a constant updating of the vaccine components, typically being completely changed on a yearly basis.

It is an advantage of the present invention that the naturally occurring exposure to influenza virus is advantageously exploited by the boosting embodiments of the invention. In other words, the present inventors teach that individuals with significant T cell responses against influenza do not become infected. Indeed, it is shown that this effect is independent of whether or not detectable antibody responses are also present. Thus, the effects generated in the present invention are entirely separate to those which have been the focus of the prior art to date.

It is an advantage of the invention that cross strain protection is provided. Indeed, by generating responses to influenza nucleoprotein, a protective effect is obtained.

Approximately 85% of the human population at large have T cell responses against flu antigens. After approximately 2 to 4 years, the responses drop below a protective level. These individuals therefore become susceptible again and are vulnerable to infection/re-infection once their response has declined below protective levels. One aspect of the invention involves the boosting of pre-existing T cell responses against influenza virus to protective levels or above.

Another aspect of the invention relates to the boosting of T cell responses against influenza antigens to a higher than normal level. By 'normal level' is meant the typical or average level of responses in an individual post-infection. The advantage of this embodiment is that the response takes longer to decay or to decline and so therefore the window during which the individual remains protected (i.e. maintains a T cell response at or above the protective level), is advantageously extended. This has the benefit of increasing the interval between boosts which are required to maintain effective protection.

Prime-Boost

Some aspects of the invention involve prime-boost vaccination regimes. Such techniques are well known in the art. In outline, prime-boost refers to the process of initiating an immune response ('prime') and then subsequently stimulating/enhancing/extending that response ('boost').

Suitably best results are obtained when the antigens for the prime and the boost overlap (ie. have one or more antigens or epitopes in common) or are the same.

Suitably homologous prime-boost may be carried out. This means that the vectors and/or formulations for the prime and the boost(s) are suitably the same. Modified Vaccinia Ankara (MVA) based vectors are well suited to homologous prime-boost since they do not replicate in mammalian cells and thus typically do not induce problematic anti-vector immune responses in the subject. This has the advantage of subsequent doses (boosts) remaining effective rather than being ameliorated by anti-vector responses in the subject.

Suitably heterologous prime-boost may provide enhanced responses. Heterologous prime-boost describes the administration of different vectors and/or formulations for the prime and the boost(s). Most suitably heterologous prime boost refer to the administration of different vectors for the prime and the boost(s). A key benefit of heterologous prime-boost is the avoidance or reduction of anti-vector responses, which often leads to a better response to (heterologous) boosts than in homologous prime-boost approaches, particularly when the prime and boost immunisations are given within a few weeks of one another. In heterologous prime-boost approaches, suitably one vector is an adenovirus based vector, and the other vector is an MVA based vector. Suitably in heterologous prime-boost approaches, suitably the first composition comprises an adenovirus based vector, and the second composition comprises an MVA based vector.

Multiple boosts may be applied. For example, a single prime may be followed by one boost, or by two boosts, or by three boosts, or even more. Some regimes may comprise a prime followed by a greater number of boosts, for example regular boosts administered at specific times (eg. every 3 years, every 5 years, every 10 years) throughout the subject's life. Alternatively some regimes may comprise a prime followed by a greater number of boosts, for example regular boosts administered under specific conditions (eg. when a response has declined to a predetermined level such as below the threshold for protection) throughout the subject's life.

In some aspects the invention relates to 'boost-only' vaccination regimes. In these aspects the subject has a pre-existing response at some level, whether or not that is protective. This pre-existing response may have been acquired by previous or current infection, or may have been acquired by prior vaccination. The important point is that the subject displays some kind of immune response against influenza so that the vaccination given according to the present invention is considered to be a 'boost'. MVA is particularly good at boosting pre-existing T cell responses, so suitably the vector is MVA. A 'prime' is considered to be a vaccination given to a patient who has either never been exposed to influenza virus or who exhibits no detectable response against influenza (a 'naïve' subject—discussed in more detail below).

Multiple boosts may be homologous or may be heterologous as explained above.

It is an advantage that the invention directs immune responses against conserved antigens and provides cross protection. Together, these effects advantageously provide a broad protection and a stable protection against influenza virus infection.

Naïve Subjects

Some individuals in the population do not possess a pre-existing immunity to influenza virus. These individuals may be infants, or may be adults who have never encountered the virus. Alternatively, there may be adults who have previously encountered the virus, but for whom so much time has elapsed since the virus was last encountered that the response has decayed to the point of being undetectable. Any such individuals are considered to be naïve individuals. Clearly, a boost only approach may not be appropriate for producing protective immunity in such subjects. Suitably a prime-boost approach is adopted when vaccinating naïve individuals. This may suitably take the form of a plurality of MVA based immunisations, or may take the form of an adenovirus based prime followed by an MVA based boost. Any other suitable prime-boost combination may be employed.

It is an advantage of the invention that a single vaccination (eg. a prime or boost) against influenza conserved antigen(s) may give rise to a protective T cell response. This unexpected finding is not predicted from prior art studies, for example in the case of malaria it can take years of exposure even to produce a semi-protective effect.

In order to determine whether or not an individual is "naïve" with respect to exposure to influenza virus, the T cell response to flu antigens is determined. If the individual does not have positive T cell responses to any influenza antigens that person is deemed to be naïve. A positive response is described as a response in an ELISPOT assay that is greater than the mean of the non-specific (background) response plus three times the standard error of the non-specific response.

Advantages

To the knowledge of the inventors, the approaches and materials described herein have not been generated previously and they represent a step change from prior art based approaches. Prior art antibody based approaches are believed to neutralise the virus before infection occurs (that is, the virus has entered the upper respiratory tract but has not infected a cell). This is believed to be a key aim in protecting individuals from the effects of an influenza infection, or indeed protecting them from the infection itself. In order to be the subject of a T cell based response, the subject's cells themselves must be infected. Thus, the view in the art is that a T cell mediated immune response cannot prevent infection, since infection by a host cell is considered a prerequisite for the action of that response.

It is to be noted that of the approximately 50 or more vaccines on the market today, at most one of those appears to be working via T cell based responses. The only candidate vaccine which might be working via this mechanism is the BCG vaccine for tuberculosis, which is clearly not relevant to influenza.

Most activity in the prior art generation of influenza vaccines has been focussed on surface antigens, which are extremely variable. The only attempts to utilise conserved antigens are based on the M2 matrix protein. The amino acid sequence of M2 matrix protein is not in any way related to that of the M1 matrix protein. The M1 protein consists of 252 amino acids whereas the M2 protein consists of only 97 amino acids and therefore contains few potential T cell epitopes. The M1 protein is internal in the influenza virus whereas the M2 protein, which is an ion channel protein, extends to the surface of the virus. Furthermore, the only attempts to utilise conserved antigens in an influenza vaccine have been concerned with a generation of antibody based responses.

In the prior art, T cell based responses are considered to involve an unwieldy lag phase. The reason for this is believed to be that the T cells require time to multiply. The clear expectation from an understanding of the prior art is that the appropriate T cells would not be predicted to reach the lung fast enough to prevent death of the subject. By contrast, antibody responses are typically much more rapid in accumulation. Moreover, antibody responses are regarded as more rapidly deployed than T cell based responses. T cells are regarded as being slow particularly in migration or localisation to the site of action. Thus, from an understanding of the prior art, at best the expectation might be that T cell based immunity might limit the severity of an infection, but would be regarded as incapable of meaningfully preventing or protecting from such an infection. By contrast, the present inventors have shown that T cell based immunity represents an excellent vaccination strategy against influenza. Moreover, it is an advantage of the invention that even though the target tissue(s) of the vaccine-induced immune response is the respiratory mucosa, it is the case that the vaccine need not be applied to the mucosa but a standard intramuscular or intradermal vaccination route may be used.

Dosage/Administration

Dosage may be varied by the skilled operator. Different dosage regimes may be operated by the skilled worker. Different prime-boost regimes may be deployed by the skilled worker, particularly in vaccination of naïve individuals.

Suitably single dose vaccinations are used.

Suitably no adjuvant is administered with the compositions of the invention. Suitably the compositions of the invention do not comprise adjuvant.

Suitably the compositions of the invention comprise suspended virus (viral vector particles) carrying nucleic acid encoding the influenza antigens/epitopes of the invention. Suitably the viral vector does not comprise influenza polypeptides or influenza sequences other than those encoding the epitopes/antigens of interest.

Suitably the compositions comprise buffering components in an amount effective to maintain the integrity of the viral vector(s) of the invention.

Excipients to facilitate lyophilisation of the virus or to allow ambient temperature storage of the vaccine may additionally form part of the compositions.

In one embodiment the viral particles may be mixed with or coadministered with (eg. in the same sample and/or at the same site and/or at the same time) one or more proteins such as influenza HA (haemagglutinin) or NA (neuraminidase). In this embodiment, the compositions of the invention may be mixed with one or more conventional influenza vaccines to produce a new composition. These embodiments have the advantage of inducing a parallel antibody response resulting in a mixed antibody and cell based response. Thus the invention relates to compositions as described above further comprising one or more external influenza antigens. Thus, it is also possible to modify the compositions of the invention so that they also induce antibodies to one or more external proteins of the virus. MVA has been shown to adjuvant antibody responses to proteins injected with it and replication-deficient adenovirus-vectored vaccines induce antibodies against proteins expressed by the vaccine. Thus it would be possible to combine the broad cross-protection obtained by T cells recognising conserved antigens with the complete protection against infection provided by antibodies to the external antigens. Combining T cell and antibody mediated protection in one vaccine should give equivalent vaccine efficacy against seasonal influenza to those vaccines in current use, with the additional benefit of substantial protection against any new subtypes via T cells recognizing and destroying virus-infected cells. Viral vectors such as MVA can have an adjuvant effect. However, further adjuvant may advantageously be provided—suitably such mixed compositions may further comprise adjuvant such as aluminium based adjuvant eg. alum or aluminium hydroxide.

When the epitope or nucleic acid encoding it is comprised by a viral vector, suitably $1\times10^6$ to $1\times10^9$ pfu (plaque forming units) are administered in a single dose. More suitably $1\times10^7$ or more pfu are administered in a single dose, which has the advantage of increased immunogenicity. More suitably $5\times10^8$ or less pfu are administered in a single dose, which has the advantage of avoiding possible side effects of higher doses. Thus, suitably $1\times10^7$ to $5\times10^8$ pfu are administered in a single dose. More suitably $5\times10^7$ to $2.5\times10^8$ pfu are administered in a single dose. Suitably $5\times10^7$ pfu are administered in a single dose. Suitably $2.5\times10^8$ pfu are administered in a single dose.

Suitably said doses are for adult primates such as humans. Doses for other subjects such as avian species or infant primates such as humans may be determined from the guidance provided.

Suitably administration is by any suitable route known to the skilled person such as by needle or by transdermal patch delivery. Suitably administration is by needle.

Suitably administration is not intravenous.

Suitably administration is subcutaneous, intradermal or intramuscular. Suitably administration is intradermal or intramuscular since these show better immunogenicity. Suitably administration is intradermal. Most suitably administration is intradermal by needle.

The particular sequence of the antigens used might be varied, for example if an "escape mutation" is detected in a virus of interest. In this scenario, it would be desirable to change the specific sequence of one or more of the antigens used in vaccination in order to re-map the immune response onto the escape variant. Typically this might involve replacement of the antigen sequence with a sequence incorporating the escape variant.

Suitably one or more conserved antigens are used in the compositions of the invention. Suitably two or more conserved antigens are used in the compositions of the invention. Suitably said conserved antigens comprise one or more of influenza nucleoprotein (NP) and matrix 1 (M1) polypeptides. Suitably said conserved antigens comprise both influenza nucleoprotein (NP) and matrix 1 (M1) polypeptides. Suitably said conserved antigens comprise at least one epitope from both influenza nucleoprotein (NP) and matrix 1 (M1) polypeptides.

In principle, any nucleoprotein/matrix 1 protein sequence(s) capable of inducing the responses of the invention may be employed.

It is an advantage of the various constructs of the invention that both antigens are effectively expressed.

It is an advantage of the invention that the antigenic constructs are markerless. Removal of marker genes such as beta-galactosidase can destabilise the viral vectors. For example, fowlpox based vectors can be susceptible to destabilisation by removal of the beta-galactosidase markers which are typically included therein. However, we have surprisingly shown that markerless vectors according to the present invention are indeed stable and provide effective expression of the internal antigens of interest.

Advantageously, the antigens are from, or are derived from, the H3N2 influenza strain.

Advantageously, the antigens are from, or are derived from, the A/Panama/2007/99 subtype of the H3N2 influenza strain.

Advantageously, the antigens comprise, or are derived from, antigen sequence(s) in the sequence listing.

Advantageously, the antigens are arranged in the order (N terminus-nuclear protein-matrix 1 protein-C terminus) of the fusion protein of the invention.

Advantageously the antigens are provided as a single polypeptide ('fusion protein'). This ensures antigens are co-expressed.

Advantageously the antigens of the invention are separated by a linker sequence. This allows a superior folding of the polypeptide chain, and advantageously results in the correct presentation of the antigens of interest.

Most prior art vectors involve a leader sequence. This is typically used in prior art based vectors, for example to provide a secretion signal to ensure that the antigen is available to the immune system. Alternatively, leader sequences are employed to provide improved expression. However, by contrast, the constructs of the present invention suitably do not comprise a leader sequence. The constructs of the invention suitably do not comprise a secretion signal. It is surprising that excellent antigenicity and polypeptide expression are obtained even in the absence of a leader sequence.

In the prior art, it is standard practice to eliminate all potential glycosylation sites from the antigens of interest. However, by contrast, the present inventors teach that glycosylation sites should be maintained. Thus, suitably the antigens of the invention retain their naturally occurring glycosylation sites.

It is an advantage of the invention that no terminator sequences are used in the constructs of the invention.

Suitably the construct (eg. epitope/antigen coding inserts) of the invention including the antigens of interest is synthesised in vitro. By synthesised in vitro it is meant that the nucleic acid encoding the antigens of interest is synthesised de novo, rather than being derived by cloning based techniques from an actual viral nucleic acid sequence. Suitably, the desired amino acid sequence is used as the basis for artificially synthesising the nucleic acid of the invention. In some embodiments the invention relates to construct(s) (eg. epitope/antigen coding inserts) themselves, e.g. as nucleic acid cassettes, whether or not they are present in a vector capable of directing their expression in an animal cell. In another embodiment the invention relates to the fusion protein(s) described herein.

Advantageously, human codon optimisation is used.

A further advantage of the linker sequence is that the linker is protease susceptible. This advantageously permits the two or more epitopes/antigens to be separated, thereby advantageously alleviating immunodominance effects which can be created by the coupling of antigens.

With respect to the antigens chosen, or in particular with respect to the antigenic sequences chosen, clearly variants of the sequences which have been exemplified are considered to be within the scope of the invention. For example, chimeric molecules involving parts of the antigen(s) from different sub-types could be created. Alternatively, point mutations might be introduced with the aim of catching "escape variants" of the virus as discussed herein.

An immune response will generally be considered to have been generated by the methods of the present invention if it leads to a doubling of the pre-existing measured T cell response following vaccination, or increased by more than 200 specific cells per million per peripheral blood mononuclear cells. In other words, the strength of a T cell response may be measured in a subject before vaccination. Following vaccination, the response is measured again. If that response has at least doubled, or increased by more than 200 specific cells per million per peripheral blood mononuclear cells, then the vaccination will be generally considered to have produced an immune response according to the present invention.

It is an advantage of the invention that at least two conserved influenza antigens are used.

It is an advantage of the invention that no external influenza antigens are used.

It is an advantage of the invention that a "pure" T cell response is generated.

It is an advantage of the invention that the immune responses generated are better than could have been anticipated. Indeed, it is this surprising effect which forms the basis of the present invention.

It is an advantage of the invention that the vector constructs expressing the antigens of interest may be produced without cumbersome marker sequences being present.

In one embodiment, the invention relates to a DNA based priming vaccination followed by an MVA based boosting vaccination.

It is an advantage of the invention that immunodominance effects are avoided. In the prior art, problems are often experienced in generating good responses from the simultaneous vaccination with two or more antigens. It is a surprising benefit of the present invention that robust immune responses are seen against each of the antigens used in vaccination.

The invention relates to an influenza vaccine for heterosubtypic protection.

Influenza Viruses

Influenza viruses are members of the Orthomyxoviridae family of RNA viruses. They are classified as type A, B or C based on antigen differences in their nucleoprotein (NP) and matrix protein (M1), and type A viruses are further subtyped based on the antigenicity of the haemagglutinin (HA) and neuraminidase (NA) surface glycoproteins. There are currently 16 HA and 9 NA subtypes, and all subtypes are maintained in aquatic bird populations. The genome of influenza A consists of eight single-stranded negative sense RNA molecules, encoding 11 proteins.

Influenza virus infections do not usually result in disease in wild bird populations, but can be transferred from them to domestic poultry, where they may case disease which is sometimes fatal, and may then also cause infections of humans. If the virus then mutates or reassorts with another subtype capable of transferring between humans, a novel strain to which humans have no immunity can arise and cause a pandemic. At least 40 million people died in 1918-19 from 'Spanish influenza' caused by an H1N1 virus. Subsequent pandemics in 1957 (H2N2), 1968 (H3N2) and 1977 (H1N1) were each caused by new strains arising. The 1968 virus had avian HA and PB1 segments but all other segments had previously been identified in humans. Recently, strains only previously found in avian populations (H5N1, H9N2 and H7N7 subtypes) have been directly transmitted to humans. As yet there is little evidence of human to human transfer of these subtypes, but it is likely that new strains will arise and result in a new pandemic.

Recombinant modified vaccinia virus Ankara (MVA) has been found to induce a dramatic boosting of pre-existing T cell responses, however they were generated initially. Both CD4+ and CD8+ responses are boosted. Thus MVA may be used in the invention to boost existing CD8+ memory responses that have been primed by exposure to influenza. Infection or vaccination results in a rapid induction of effector T cells which may control the infection. This is followed by a contraction phase with apoptosis of effector cells and generation of T cell memory. It is this memory population which then expands to produce a new population of effector cells to control any subsequent infection. Importantly, the magnitude of the effector response determines the magnitude of the memory. When a memory response already exists, boosting with a highly immunogenic vaccine not only results in an effector T cell response, but will 'reset' the memory response at a higher level, resulting in a greater degree of protection at the next exposure.

Most US and UK adults have detectable levels of T cell responses to influenza antigens including NP and M1. Indeed the high mean CD8+ T cell frequency of 0.39% measured by flow cytometry (and the high frequency of CD27 on these cells reflecting limited activation) suggest that they should be readily boostable by MVA encoding influenza antigens according to the present invention. Even responses that may be too low to be reliably quantified by currently available assays may still be boosted to high levels by a single dose of recombinant MVA. Expanding the existing memory response in this way will result in an increased memory response following MVA vaccination. One application of the invention is to boost the very low level responses in the majority of the population to protective levels, such that the majority of the population are protected against infection rather than the 33% who were found to be protected in an influenza challenge study. In another embodiment, by boosting the other individuals (eg. the 33% of the population with measurable protection), their T cell responses may advantageously be further amplified leading to stronger and more durable protection.

Vectors

Non replicating viral vectors suitable for use in primates such as humans should be used. The vector(s) should have the capacity to direct epitope (polypeptide) production in one or more host cells of the subject into which it is introduced. This is important in the production of the correct cell mediated immune response since the epitopes of interest should be delivered into (eg. produced inside) said cells, and preferably not be significantly exported or secreted, in order for the correct immune effects to be achieved according to the invention. Suitable vectors may include poxvirus based vectors such as ALVAC or MVA, Adenovirus based vectors, VEE, or any other suitable vector known in the art.

MVA is an excellent choice of vaccine vector. As it does not replicate in humans it is incapable of causing a disseminated infection and poses no safety concerns. It is manufactured in chicken embryo fibroblast (CEF) cells. Since embryonated eggs and CEFs are widely used in manufacture of other vaccines there is a ready supply of CEFs, and the manufacturing process for recombinant MVA is simple and scalable. The use of recombinant MVA in numerous trials, which have included young children and HIV positive individuals and individuals latently infected with TB, has resulted in a large accumulation of safety data and experience of manufacturing and using MVA expressing different antigens, all of which support the use of recombinant MVA as a safe and immunogenic T cell boosting vaccine (Moorthy, Imoukhuede et al. 2004; Dorrell, Yang et al. 2005; Webster, Dunachie et al. 2005, Bejon, Mwacharo et al. 2006).

Suitably the MVA vector used is the standard MVA produced by Anton Mayr after 570 passages in CEFs as is most commonly used in the art.

Any suitable adenovirus based vector may be used such as those described in WO2005/071093 or WO2006/048215. Suitably the adenovirus based vector used is a simian adenovirus, thereby avoiding dampening of the immune response after vaccination by pre-existing antibodies to common human entities such as AdHu5. Suitable simian adenovirus vectors include AdCh63 (patent number WO/2005/071093) or AdCh68 (Cohen et al., J. Gen Virol 2002 83:151) but others may also be used. Suitably the adenovirus vector will have the E1 region deleted, rendering it replication-deficient in human cells. Other regions of the adenovirus such as E3 and E4 may also be deleted.

Thus the invention provides a recombinant MVA expressing internal influenza antigens, and the use of that vaccine to boost T cell responses to protective levels. Although the effector T cell response generated after MVA immunisation peaks rapidly and then declines over a period of weeks, T cell memory continues to increase over a period of six months, and it is this memory response that will protect vaccinees from subsequent infection and is a preferred immune response of the invention. Thus in one embodiment the invention provides a single dose vaccine that provides cross-strain and cross-subtype protection against disseminated infection arising from both human and avian influenza, or at least greatly reduces both symptoms and virus shedding if infection should occur, provided that some memory T cell responses have been primed by prior exposure (or by priming vaccination).

For vaccination of influenza-naïve individuals, suitably two or three immunisations with recombinant MVA, or a priming immunisation with an alternative vaccine vector followed by boosting with MVA are used. The repeat use of the same recombinant MVA to 'reboost' effector responses may be used. Since MVA does not replicate in human cells, immune responses to the vector are low, and advantageously do not preclude re-use of the same vaccine.

Suitably the nucleic acid encoding the epitopes/antigens is inserted at TK locus of MVA.

Suitably the nucleic acid encoding the epitopes/antigens is under the control of the vaccinia P7.5 promoter.

Immune Responses

A key element of the approach of the invention is that the immune response is forced into a cell mediated response. This is a feature of the use of viral vectors for delivery of the epitopes/antigens of interest. Prior art approaches rely on the presentation of antigen directly in preparations of protein with or without adjuvant. This type of presentation of antigen leads to antibody based responses. However, the compositions of the invention direct the production of epitopes or antigens inside cells of the host subject. This leads to their presentation to T cells and thus to cell mediated immunity. This is a core distinction over prior art based approaches which do not produce protective cell based immunity and which operate through antibody production.

Protection mediated by T cells will not prevent initial infection of the upper respiratory tract by influenza, which antibody-dependent protection can do. However, upon vaccinating (boosting) according to the present invention the memory T cell response is capable of rapid expansion to produce effector cells which destroy virus infected cells, prevent the spread of infection and limit the disease symptoms.

The invention relates to a cross-strain and cross-subtype vaccine based on internal influenza antigens. This can be manufactured and widely used because it may protect against human influenza (H1N1 and H3N2) as well as a potential H5N1 pandemic, or a pandemic caused by any subtype currently found only in avian species. Such a T cell inducing vaccine thus finds application in industry for at least these reasons.

Suitably the immune response is in an animal, more suitably in a vertebrate, more suitably in an avian species (e.g. birds such as chicken or other livestock or domestic avian species) or a primate, more suitably in a primate such as a human. Suitably the subject(s) upon which the invention is practiced are vertebrates, more suitably avian species or a primates, more suitably primates such as humans. Suitably the methods of the invention are for inducing immune responses in vertebrates, more suitably in avian species or a primates, more suitably in primates such as humans.

Thus the invention further relates to use of the compositions of the invention, such as vaccine compositions, in birds. When using the composition(s) in birds such as chickens, suitably said composition is administered or delivered in ovo or by injecting chicks.

Preferably the immune responses of the invention are cell mediated responses such as T cell mediated responses.

In one aspect, suitably the invention is not applied to equine species. In this aspect, suitably equine species are excluded from the invention.

It should of course be noted that different individuals respond to different epitopes due to MHC restriction. Therefore it is an advantage of the invention to use complete NP and/or complete M1 polypeptides ie. full length polypeptides so that all naturally occurring epitopes are thereby embraced. Epitopes or antigens of one or more further influenza proteins may advantageously be added to the compositions of the invention. For example a further non-structural influenza protein may be added. However, it is an advantage of the invention that inclusion of both NP and M1 provide the broadest possible coverage of naturally occurring responses whilst minimising the number of antigens used and thus represent an optimal formulation according to the invention.

Further Applications

The composition of the invention is suitably a vaccine composition.

In another aspect the invention relates to a composition for generating an immune response against an influenza virus, said composition comprising one or more epitopes of one or more internal proteins of influenza virus. In another aspect the invention relates to a composition suitable for inducing a T cell mediated immune response against an influenza virus, said composition comprising one or more epitopes of one or more internal proteins of influenza virus. In such aspects it is important to ensure that the response is indeed the cell mediated response of the invention. Thus, the epitopes or antigens should be delivered into cells of the subject rather than simply delivered in a manner which might solely induce an antibody response. Thus the epitopes or antigens are suitably delivered in a form which permits crossing of the cell membrane or cell entry by other means. This may involve presenting the epitopes as fusion proteins fused to one or more transport domain(s) capable of delivering the epitopes into the cell(s) of the subject.

Thus the invention relates to single dose vaccines such as kits comprising one composition of the invention for boosting pre-existing memory T cell responses to influenza.

The invention also relates to multi dose vaccines such as kits comprising two or more compositions of the invention for administration to non-primed or naïve subjects.

The invention also relates to polypeptides having an amino acid sequence as disclosed herein, such as in the sequence listing.

The invention also relates to nucleic acids having a nucleotide sequence as disclosed herein, such as in the sequence listing. The invention also relates to nucleic acids having a nucleotide sequence encoding an amino acid sequence as disclosed herein, such as in the sequence listing. The invention also relates to nucleic acids having a nucleotide sequence which differs from a nucleotide sequence as disclosed herein only by silent mutations which do not change the encoded polypeptide.

In another aspect the invention relates to a composition for generating an immune response against an influenza virus, said composition comprising nucleic acid encoding one or more epitopes of one or more internal proteins of influenza virus.

Immune responses induced by the immunogenic composition(s) disclosed may have further utilities in addition to the induction of protective immunity. These include the generation of reagents such as T cells useful in diagnostic assays, the generation of T cells useful in adoptive transfer protocols e.g. for immunoprophylaxis and/or immunotherapy, and the use of the immunogenic composition(s) to assess the immunocompetence of a subject to which it is administered.

The invention is now described by way of example. These examples are intended to be illustrative, and are not intended to limit the appended claims. Reference is made to the following drawings:

EXAMPLES

Example 1: T Cell Inducing Vaccines for Flu

Rationale:
Nucleoprotein (NP) identity
92% between H3N2 and H1N1 strains
91% between H3N2 and H5N1 strains
M1 (matrix) identity 95% between H3N2 and H1N1 strains 93% between H3N2 and H5N1 strains
Vaccine design: MVA-Flu
Antigen: NP:M1 fusion protein
H3N2 sequence used
Flexible linker between NP and M1
total coding sequence of 758 amino acids
Inserted at TK locus of MVA
Vaccinia P7.5 promoter
No marker gene Most adults have been exposed to influenza and have some T cell memory against NP and M1. Immunisation with recombinant MVA expressing NP and M1 boosts these to potentially protective levels.

The vaccine is GMP manufactured.

Phase I trial uses healthy volunteers, tests T cell responses before and after immunisation with MVA.

Dose comparison 5×10$^7$ pfu i.d. (n=12) and 2.5×10$^8$ pfu i.d. (n=12)

Phase IIa Study

Choose immunisation dose according to above.

Immunise 12 people with low antibody titres

Challenge these 12 plus 12 controls using H3N2, oseltamivir sensitive strain available. Virus shedding in nasal washes is measured.

Vaccine may be formulated as a combination product.

Example 2: Preferred Epitope Construct

The epitope construct is prepared according to the sequence shown in FIG. 1. In this example the nucleic acid is synthesised in vitro and is then ready for cloning into a delivery system such as a viral vector eg. MVA.

Example 3: Immunogenicity of MVA-NP+M1 in Mice

Groups of four mice BALB/c mice were immunized with either 1×10$^6$ pfu MVA-NP+M1 intradermally, or 50 μg of a DNA vaccine expressing the same NP+M1 insert intramuscularly followed by 1×10$^6$ pfu MVA-NP+M1 intradermally two weeks later. Two weeks after the MVA immunisation the spleens were tested for T cell responses to the immunodominant peptide TYQRTRALV (NP amino acid residues 147-155, SEQ ID NO: 6) in an interferon-gamma ELISPOT assay as described in Schneider, J., et al., (1998) *Nat Med* 4, 397-402.

Results are plotted in FIG. 2 as the mean of four mice, and the response generated by vaccination to peptide TYQRTRALV (flu peptide, SEQ ID NO: 6) are shown compared to the non-specific background response (no peptide). In these mice which have not been previously exposed to influenza, MVA is able to prime a T cell response to NP, as shown by the MVA alone group. In mice which are first primed using a DNA vaccine, the response is boosted to a higher level by MVA-NP+M1.

Responses to two additional peptides, both derived from M1, are also measured (FIG. 3). Peptide 57 contains the epitope VFAGKNTDL (SEQ ID NO: 4) and peptide 64 contains the epitope LYRKLKREI (SEQ ID NO: 5). "Net" indicates peptide-specific response minus background.

Therefore we show that in the same mouse strain T cell responses can be induced to both the NP and M1 antigen using the a NP-M1 construct according to the present invention in an MVA vector. So despite the artificial linker between the antigens and despite the possibility of antigenic competition occurring we show that both antigens are advantageously immunogenic for T cell induction, and in particular with the MVA vector.

Example 4: Measuring T Cell Responses to NP and M1 in Clinical Trials

Measurement of MVA-NP+M1 Immunogenicity in Volunteers:

T cell responses to nucleoprotein and matrix 1 proteins of influenza A can be measured using an ELISPOT assay to enumerate interferon-gamma (INF-gamma) secreting T cells derived from peripheral blood samples, after stimulation with pools of overlapping peptides spanning the entire sequence of NP and M1. The specific response to each of the pools is added together to arrive at the total T cell response to these two antigens. The average response to these two antigens in UK adults is in the region of 100-200 INF-gamma secreting cells per million PBMCs. During the clinical trial of MVA-NP+M1 the pre-existing response to NP+M1 is measured at two time points prior to vaccination, then at one week after vaccination in addition to later time points. Successful boosting of the T cell response by vaccination will result in increasing this response typically by more than 200 INF-gamma secreting cells per million PMBC to typically over 500 INF-gamma secreting cells per million PMBC.

Example 5: A New Influenza Vaccine for Heterosubtypic Immunity

Overview:

The risk of a major global pandemic of avian influenza has created widespread and justified concern. Vaccines designed to induce antibodies against H5 haemagglutinin present an obvious potential control measure but the current high rate of diversification of H5N1 strains suggests that vaccines made now may differ so much in their H5 sequence from any pandemic strain that emerges that these vaccines would have little or no efficacy.

However, cytotoxic T cells specific for the internal proteins NP and M1 show high cross-reactivity between strains and between subtypes, reflecting the 92-94% conservation of the internal proteins. Protective T cells are induced by influenza infection, and 90% of the adult UK population has memory T cells to 'flu antigens, but the level of effector cells quickly declines below that needed for protection.

We will conduct a clinical trial using Modified Vaccinia virus Ankara (MVA) expressing internal 'flu antigens to boost pre-existing memory responses back to protective levels. Earlier clinical trials with MVA expressing malaria and tuberculosis antigens have demonstrated that it is safe and highly efficient at boosting T cell responses in humans. During the trial, cross-reactive responses will be assessed to determine the potential of the new vaccine to protect against H5N1 as well as H3N2 and H1N1.

Example 6: Manufacture and Trial

The recombinant MVA may be constructed as above, and manufactured commercially by IDT, Germany.

Experimental Design and Methods: Vaccine Design

The composition of this example is a recombinant MVA virus expressing influenza A nucleoprotein (NP) fused to matrix protein (M1) via a flexible linker (GGGPGGG, SEQ ID NO: 3) to form a single open reading frame (NPM1). There is very little polymorphism of these sequences between influenza A isolates. NP is 92% identical between H3N2 and H1N1 strains, and 91% identical between H3N2 and H5N1 strains. M1 is 95% identical between H3N2 and H1N1 strains, and 93% identical between H3N2 and H5N1 strains. This low level of variation appears to allow strong T cell cross-reactivity. For comparison, the sequence of TRAP antigen used in our malaria vaccine differs by 8% from the sequence in the challenge strain, and excellent immunological crossreactivity and cross-strain protection was observed. However, we choose the H3N2 sequence for this trial as this is the sequence to which most people will have memory T cell responses. We measure immune responses to NP and M1 of this subtype, to the other common human H1N1 subtype and to the avian H5N1 subtype.

Expression of the antigen is driven by the Vaccinia P7.5 early/late promoter and the antigen is inserted at the thymidine kinase (TK) locus of MVA. Such similar constructs have been extensively tested for genetic stability and no evidence for instability has been detected. Four existing recombinant MVA vaccines all express beta-galactosidase from *Escherichia coli* as a marker gene, inserted adjacent to the antigen and expressed from the Vaccinia late promoter P11. This allows identification of recombinant virus for plaque picking during the initial isolation of the recombinant virus, and as it is driven by a late promoter is not well expressed in mammalian cells after immunisation. However we have now developed methodologies using transient dominant selection of fluorescent protein markers that allow the isolation of recombinant MVA lacking any marker, and the NPM1 construct is produced in this way. This then requires the adaptation of existing quality control assays for use with markerless virus.

A GMP manufacturing company (Imstoffwerke Dessau Tornau (IDT), Germany) can produce MVA-NPM1 under contract, and any new assays that are required for producing a markerless MVA carried out.

Manufacture

MVA-NPM1 is generated as above, and characterised by sequencing of the insert and flanking regions of the virus. Immunogenicity of the construct is checked by a potency assay in mice, in which responses to a known T cell epitope in mice (the H-2Kd restricted peptide NP 147-155 TYQRTRALV (SEQ ID NO: 6)) are checked. A seed stock of the virus can then be supplied to IDT, who prepare a master seed bank of the virus and produce a clinical lot in vials ready for use. Quality control of the vaccine can be carried out by IDT, and toxicology studies can be carried out by a GLP-compliant contract research organisation. These studies generate the data required for a Clinical Trials Application (CTA) to the MHRA, which can be backed up by extensive safety data from previous clinical trials of recombinant MVA vaccines.

Safety and Immunogenicity Study

Healthy adult volunteers can be recruited from the local population. These need not be selected for vaccinia immunisation status as prior smallpox immunisation >20 years earlier has been found to have minimal effects on MVA immunogenicity. In safety and immunogenicity studies 12 people will receive a dose of $5 \times 10^7$ pfu intradermally, and 12 receive a dose of $2.5 \times 10^8$ pfu. The low dose group will be completed and approval received from the independent safety monitor of the trial before commencing the high dose group. In trials of MVA 85A (tuberculosis) volunteers who had previously received the BCG vaccine and were then given a single dose of MVA 85A of $5 \times 10^7$ pfu, the T cell response to antigen 85A was boosted to extremely high levels and remained elevated for over a year (McShane, Pathan et al. 2004). However in malaria vaccine trials, higher doses of MVA resulted in higher T cell responses (McConkey, Reece et al. 2003). Therefore this initial study will test if a single low dose, or single high dose, of MVA-NPM1 causes a significant boost in T cell responses to the antigens encoded in it, in a study population who would be expected to have some pre-existing immunity to influenza A (see statistical considerations below).

In addition to routine blood safety assays (as used in our many previous MVA studies) both ex vivo (to measure effector response) and cultured (to measure memory response) IFN-gamma ELISPOT assays will be carried out on blood taken from the volunteers at their screening visit and on the day of immunisation, in order to have two separate measures of the pre-existing responses in the volunteers. After vaccination blood will be taken from volunteers 1, 3, 8 and 24 and 52 weeks post vaccination and again ex vivo and cultured IFN-gamma ELISPOT assays as well as flow cytometry will be carried out. Full GCLP quality assays for these T cell responses are preferably conducted. For selected epitopes, HLA class I types tetramers are available and these will be used to phenotype the induced CD8+ T cells. We evaluate subtype crossreactivity by pooling peptides that are completely conserved between the H3N2, H1N1 and H5N1 subtypes and making subtype specific pools to allow quantitation of subtype crossreactivities.

Efficacy Study

Provided a significant boost of immune responses is observed following immunisation, we will then proceed to an efficacy study, also in healthy volunteers. Challenge studies with influenza were undertaken safely by the Common Cold Research Unit at Salisbury for many years and provide an option for rapid assessment of the efficacy of new vaccines. The dose of MVA-NPM1 to be used is chosen following review of the safety and immunogenicity data and discussions with the trial safety monitor. Volunteers who have very low or absent antibody levels to the challenge strain of virus will be selected, so as to minimise confounding of the efficacy study by pre-existing antibody. Volunteers will be immunised and monitored as for the immunogenicity study, and then given infectious influenza A virus intranasally three weeks after the immunisation. There are facilities at the Centre for Clinical Vaccinology and Tropical Medicine (CCVTM), Oxford, to house six volunteers in negative-pressure contained in-patient rooms at any one time. Therefore four groups of six volunteers (three immunised, three controls) will be challenged and followed up separately. The virus used for challenge will be subtype H3N2, and will be oseltamivir sensitive. The batch that will be used has been produced under GMP conditions by Berna Biotech, and has already been given safely to 200 people.

A recent US study described clinically insignificant cardiac irregularities in healthy young volunteers undergoing influenza challenge (Ison, Campbell et al. 2005). The study was carried out after one subject in a previous study developed temporary myocardial dysfunction following influenza challenge. This subject was said to have no history of cardiac abnormalities, but in fact should have been identified as being at risk because of the anthracycline treatment he had received. Taking this into account, we will only recruit volunteers under the age of 40. The screening of volunteers will include a personal medical and drug history as well as a family history to identify any residual risk of inherited cardiac muscle or channel problems.

Nasal washes will be taken from the volunteers at the same time each day for six days and the amount of virus shedding will be measured by both viral culture methods and real-time PCR. Volunteers will have 24 hour access to care from the trial physician and nurse, and will continue to have access to trial staff after returning home on day 10 of the trial. All volunteers will be treated with oseltamivir on days 9 and 10 or earlier should there by any clinical concern. Blood will be taken for ELISPOT assays 8 and 24 weeks post vaccination (5 and 21 weeks post challenge) to examine the effect of infection on T cell responses of both immunised and control volunteers.

To maximise the amount of information obtained from the influenza challenge trials, T cell responses to all flu antigens will be measured in blood samples taken at three time points (before immunisation, after immunisation and after challenge). By studying the total T cell response to flu as well as to those antigens included in the vaccine using currently available techniques we will build on the studies carried out 20 years ago to increase our understanding and either confirm the validity of our vaccination approach and/or determine the desirability of including a different antigen in the vaccine as outlined above.

Vietnam

As NP and M1 are so highly conserved between strains of influenza A, it is expected that if the vaccine protects against challenge with strains that have circulated in humans, it will also protect against avian influenza. Since challenge with H5N1 strains will not be undertaken for safety and ethical reasons, an alternative approach to addressing this issue is to test whether MVA-NPM1 will boost T cell responses in avian flu survivors, which would indicate that conserved or cross-reactive epitopes can be boosted by the vaccine. In collaboration with the Wellcome Trust Unit in Ho Chi Minh City, Vietnam, directed by Jeremy Farrar, which has treated and studied a large proportion of the avian influenza cases in the world to date, we will carry out an immunogenicity study in Vietnam in which 12 avian flu survivors and 12 individuals who have recently had human flu will be immunised. ELISPOT assays will be carried out on pools of peptides, grouped into conserved epitopes, H1N1-specific epitopes and H5N1-specific epitopes, to assess cross-reactivity as well as total response.

Statistical Considerations

For the initial safety and immunogenicity studies, a group of 12 volunteers would be required to detect a rise of 400 spot-forming units per million cells (sfu/mill) measured by interferon-gamma ELISPOT assay, from a base line (for example from below 200 to 600, at a 5% significance level and 90% power), if the standard deviation of the changes is less than 420 (as would be expected based on data generated in malaria and tuberculosis vaccine trials). For each dose, we will test whether a rise in T cell responses follows vaccination. Using this information and data on the side-effects at each of the doses, we will then choose the dose to be used in the efficacy study.

For the efficacy study, the initial analysis will be based on dividing subjects into 'excretors' and 'non-excretors' based on the detection of influenza virus in the nasal washes. A study of 12 patients in each arm would have 80% power (significance level of 5%) to detect a change of excretion of 90% in the controls to only 16% in the vaccinated arm (ie a vaccine efficacy of over 83%). The study would have greater power to detect changes in the duration of excretion.

Example 7: Preparation of AdCh Vaccines Expressing NP+M1 Fusion Protein

Generation of Adenoviral Vectors Expressing NP+M1 Fusion Protein

Replication-defective adenoviral vectors are extremely potent vectors for genetic vaccine delivery. They are also safe vectors as they can only replicate in cell lines expressing the adenovirus E1 protein (eg. HEK 293). They infect mammalian cells and express the inserted antigen but can not spread to other cells and cause a disseminated infection. Ad vectors can be produced under GMP conditions on a large scale by culture in 293 cells and purification of the virus by chromatography or caesium chloride gradient centrifugation. Ad vectors are highly effective at priming de novo T cell responses (Maeda, West et al. 2005)

From the more than 50 human adenovirus subtypes known, the most used one is serotype 5, a subgroup C adenovirus (human adenovirus 5), that rapidly induces long lived protective immune responses. The exceptional immunogenicity of these Ad vectors is likely to reflect their ability to express high levels of transgene products (driven in most vectors by the potent CMV promoter), to activate cells of the innate immune system, to transduce immature dendritic cells driving their maturation into antigen-presenting cells, to achieve long-lasting antigen presentation by not inducing apoptosis of the transduced cells. However, pre-existing anti-adenovirus immunity and in particular neutralizing antibodies which reduce cell uptake of the adenoviral vectors, can significantly dampen vaccine responses and represents a major limitation to the successful use of common serotypes of Adenovirus (Fitzgerald, Gao et al. 2003; Shiver 2003). Adenoviral infection is endemic in the human population and more than 50% of human subjects have neutralizing antibodies to Adenovirus 5. To overcome this obstacle, a large number of novel, proprietary Ad vectors derived from chimpanzees that: i) have low/no seroprevalence in the human population; ii) can be efficiently grown in human derived production cell lines; iii) have comparable immunological potency to group C human Adenovirus in mice and primates (Patent Application: "Chimpanzee Adenovirus vaccine carriers". PCT: WO 2005/071093 A2; Priority: 2004-538799P; 23 Jan. 2004) have been constructed.

We will generate two non cross-reactive chimpanzee Ad vectors encoding for the influenza NP+M1 fusion under the control of a strong promoter—such as CMV IE—and with polyadenylation sequence (AdCh-NP+M1). Optimal Kozak and translational termination signals will be introduced to increase expression. The vectors will be tested for productivity, stability, ability to direct expression of the NP+M1 fusion upon infection of susceptible cell lines and immunogenicity in mice.

To check for expression of the selected antigens, HeLa cells will be infected with the vectors, cell extracts will be prepared and analyzed by Western blot. To check for genetic stability, the DNA of independent clones of the vectors will be extracted after serial passages in the susceptible cell lines and analyzed by restriction analysis. One Ad vector will then be chosen for GMP production, after information on stability, yield and immunogenicity of the two constructs becomes available.

Production and Characterization of Pre-GMP and GMP Lots of Adenovirus Vaccines

Pre-clinical and clinical lots of Ad vectors will be prepared and characterized. The production of the clinical grade lot of the AdCh-NP+M1 vector will be done in GMP (Good Manufacturing Practice) conditions. The cultivation of cells and virus will be set up with the Wave Bioreactor® process (Wave Biotech), a patented bioreactor for cell culture. In this device, cell culture is performed in pre-sterile plastic bags. These bags—called Cellbags®—are single-use bioreactors. This design eliminates the need for cleaning, sterilization and associated validation, making this an ideal system for GMP applications. A simple manufacturing process involving cell expansion in Cellbags® will be used.

Purification of a GMP Lot of AdCh-NP+M1.

The goal for purification process development is to establish a scalable and cost-effective process capable of producing high quality adenovirus that is low in residual DNA (<100 pg/dose) and highly infectious (<100 vp/IU). A highly robust and sufficiently well understood process using the vector hAd6 (human Adenovirus 6) encoding for the Non Structural (NS) proteins of HCV will be used. Minor changes may be required (and could be implemented rapidly) to purify other serotypes. Since the cell suspension is planned to originate from Wave bioreactors (2×10 L), we will use the purification process defined as Final Development Process (FDP) (FIG. 4). In brief, the process consists of detergent lysis to release Ad vector from the cells and potentially to inactive adventitious agents. Furthermore, the presence of detergent throughout the process minimizes association of the virus with host cell DNA. Next, the cell line (HEK 293) DNA is selectively precipitated using a cationic detergent. The precipitated lysate is then clarified using depth filtration. In the following step, host cell proteins, unassembled virion components, detergent micelles, and nuclease are partially cleared by ultrafiltration using tangential flow filtration. Anion exchange chromatography then is used to purify the virus from residual cellular and viral components. The final tangential flow filtration step exchanges the virus into the formulation buffer and serves as a polishing step, effectively clearing residual proteins and DNA when necessary. Next, an orthogonal flowthrough chromatography step could be used to provide additional theoretical prion/viral clearance. Sterile filtration completes the process. The purified product is sampled for quality control testing and frozen until formulation.

Analytical Assays for GMP Lots of Adenovirus Vaccines.

Specific assays will be developed to check the identity, the potency, the purity and the character of the AdCh-NP+M1 vaccine, after cultivation and purification.

(1) Identity. The identity of the Ad vector will be confirmed by restriction endonuclease analysis of purified viral DNA and by ELISA of virus infected mammalian cells grown in vitro. For restriction analysis, digested viral DNA will be end-labeled with $P^{33}$-dATP, size-fractionated by agarose gel electrophoresis, and visualized by autoradiography.

(2) Potency. A potency assay by QPCR (Quantitative Polymerase Chain Reaction) technology will be developed This assay could offer the advantages of precision, throughput and simplicity. The concordance of this assay with the classical $TCID_{50}$ assay was already demonstrated for hAd6 based vectors.

(3) Purity and Residuals. The GMP lots will be tested for residual DNA, with an assay capable of precise quantitation of low levels of the cell line DNA in the vaccine bulks and final containers. The character and performance of this assay is of considerable interest to regulatory agencies whose concurrence with the use of susceptible cell line with a transformed phenotype is endowed from the E1A transgene which provides the required transcomplementation for the E1A of the vector. The data derived from this assay will be supplemented with studies which characterize the residual DNA for the presence of full length E1A sequences. Our approach to the characterization of residual full length E1A sequences is to focus analysis on the DNA of the bulks before and after the addition of the nuclease Benzonase using single tube nested PCR technology to provide a quantitation of fold clearance of residual full length E1A.

(4) Character. Adenoviruses will be characterized by a variety of classical virological methods, including transmission electron microscopy, density gradient sedimentation, SDS/PAGE. The purified preparations should be free of extraneous contamination by electron microscopy, composed of essentially intact virus particles with a minor component of empty virus capsids when analyzed by density gradient centrifugation.

Toxicology Studies with Adenovirus Vaccines.

The GMP lot of Ad vector will be tested for safety in a panel of assays that will include those listed below. Each study will involve intramuscular injection of the vaccine using a concentration of approximately $10^{11}$ viral particles/mL, or the highest concentration to be used clinically.

(A) Tissue distribution in rats. This assay is designed to investigate the vector tissue distribution. A single dose of Ad vector will be administered to a consistent number of rats by injecting in each quadriceps 250 µl of a suspension containing $10^{11}$ viral particles/ml in each quadriceps. One day and 8 days later, animals will be sacrificed to perform necropsy evaluation of vaccine tissue distribution. Vector DNA levels in various tissues will be determined by conventional PCR and real-time fluorescence quantitative PCR (TaqMan®).

(B) Single and repeated dose toxicity study in rats. The assay is designed to investigate potential toxicity arising from single or repeated administration of the vaccine. Three doses of Ad vector, spaced 2 weeks apart will be administered to a consistent number of rats by injecting 250 µl of a suspension containing $10^{11}$ particles/ml in each quadriceps. Fourteen days after the third dose a complete necropsy and histological examination will be performed, along with haematological analysis.

Optimisation of MVA Vaccine Production and Preparation of Influenza Virus

Optimisation of MVA NP+M1 Production.

The MVA-NP+M1 vaccine is constructed as above. This has been shown to be immunogenic in mice (see above). The vaccine may be produced using primary chicken embryo fibroblasts grown in roller bottles, with sucrose cushion purification of the vaccine. These are methods that have been used before in the art and permit optimisation of a scalable process. Production of the vaccine may also be done using an immortal cell line and a scalable purification process (Tangential Flow Filtration or TFF). This will permit further clinical development of the vaccine to proceed without impediment, and will also generate well characterised material for use in the pre-clinical studies described in this application. Changing production to use an immortal cell line has a clear advantage since the vaccine manufacturer will no longer be dependent on a supply of SPF eggs which might no longer be available in the event of more extensive avian influenza virus infection in poultry in Europe. The new cell line, CR-PIX-S is currently undergoing full qualification for human vaccine manufacturing.

Manufacturing of a CR-PIX-S Derived Working Seed Virus (WSV)

For the development process a new working seed virus based on the Master Seed Stock/Working Seed Stock (MCS/WCS) CR-S-PIX should be manufactured. The passage scheme of that working seed should allow large scale manufacturing. To get the necessary amount of WSV one intermediate passage between MSV and WSV should be implemented. The passage scheme should reflect the later manufacturing process and correspond to the replications cycles needed to prepare enough seed virus.

Passage numbers:
  MSV=passage 1
  WSV=passage 3
  Final product=passage 4

Process Development—Upstream Manufacturing.

For the propagation of MVA-NP+M1 in either CEF or CR-PIX-S cells different cultivation technologies must be used. At IDT the vaccine is first manufactured in CEF in roller bottle technology. The new cell technology using MVA-NP+M1 is based on suspension culture. The following table summarises the issues:

| Parameter | Roller technology with CEF | Suspension technology using CR-PIX-S | Remarks |
|---|---|---|---|
| Available data | Process parameter are known | Only basic parameters for cell growth are known. | The virus replication in CR-PIX-S should be developed and optimised |
| Cell culture medium | Cell growth in serum free medium | Cell growth in serum free medium | The cell culture medium for cell growth and virus replication in CR-PIX-S may be optimised |
| Target seed cell density | $1\text{-}2 \times 10^6$ cells/ml | $2\text{-}6 \times 10^5$ cells/ml | To be optimised for CR-PIX-S |
| Target cell density at infection | $2\text{-}5 \times 10^6$ cells/ml | $4\text{-}6 \times 10^6$ cells/ml | To be optimised for CR-PIX-S |
| Target MOI | 0.01-0.1 | 0.01-0.1 | To be optimised for CR-PIX-S |
| Target time of infection (TOI) | 24 h after cell seed | 24-48 h after cell seed | To be optimised for CR-PIX-S |
| Target time of harvest (TOH) | 42-48 h after infection | 42-48 h after infection | To be optimised for CR-PIX-S |
| Final batch size of virus harvest for process development | 20 l –50 l | 20 l –50 l | Up scale of the 20 l –50 l scale is planned. |
| Target virus harvest per cell | 10-40 pfu/cell | At least 10-40 pfu/cell | The possible virus yield per cell in suspension culture is TBC. |

Assessment of Both Technologies:

| Parameter | Roller technology (RB) | CR-PIX-S Suspension technology | Remarks |
|---|---|---|---|
| Process Steps | Cell preparation Cell seeding Medium exchange Virus inoculation Medium addition Virus harvest | Cell preparation Cell seeding Virus inoculation Medium addition Virus harvest | The process steps for suspension cells can be designed aseptically in closed systems. |
| Scale | low | high | The suspension process is not limited in terms of scalability |
| Yield per cell | high | high | |
| Material costs | high | low | Costs for RB cell culture medium are 5x higher. Costs for RB are 2x higher |
| Process duration | 72 h | 96 h | The duration of the suspension process is tbc. |
| Total process costs | high | low | RB is in terms of duration, medium costs and labour costs more expensive. |

The summary assessment of the two processes indicates that the suspension process is more scalable and has lower running costs. However the suspension technology incurs higher initial investment costs.

Downstream Manufacturing.

The existing roller bottle technology is based on centrifugation steps for product purification. This manufacturing technology is only modestly scalable and has several disadvantages in terms of reproducibility and aseptic process design. The more advanced technology is based on a combined TFF technology including removal of host cell impurities.

The following table summarizes the different technologies:

| Parameter | Centrifugation technology (CT) | TFF technology (TFF) | Remarks |
|---|---|---|---|
| Available data | Process parameter are known | Development for CR-PIX-S derived virus harvests and optimisation is needed. | |
| Duration of the manufacturing process | At least 72 h Scale dependent | Not more than 48 h | The shorter processing time is and advantage for the TFF process for the CR-PIX-S technology. |

Assessment of Both Technologies:

| Parameter | Centrifugation technology (CT) | TFF technology (TFF) | Remarks |
|---|---|---|---|
| Scalability | none | yes | The assessment is reviewed |
| Aseptic Process | limited | yes | |
| Reproducibility | low | high | |

| Parameter | Centrifugation technology (CT) | TFF technology (TFF) | Remarks |
|---|---|---|---|
| Regulatory acceptance for phase III studies | none | yes | for purification of MVA-NP-M1. |

Production of Influenza Virus for Challenge Studies

Retroscreen Virology Limited hold stocks of GMP influenza virus suitable for challenge studies in humans. The virus used for challenge is subtype H3N2, is oseltamivir sensitive and has already been given safely to 200 people. More virus will be needed for the challenge studies described above, and this will be produced using the existing GMP lot as a seed stock, at a GMP manufacturing facility owned and run by the University of Oxford. SPF embryonated eggs will be purchased from a recognised supplier (Charles River) and inoculated with the virus. After incubation for several days the contents of the eggs will be removed, centrifuged to remove solid material and sealed into sterile vials. One egg will produce up to 20 vials of virus. Two hundred vials of virus for challenge will be produced, plus extra to allow for quality control testing of the preparation. This will include titration in Madin-Darby canine kidney (MDCK) cells, sterility testing and screening for adventitious viruses. For use in challenge studies, the virus will be diluted in saline (once the titre is known, the amount of dilution required can be determined exactly but is likely to be of the order of 1 in 100) and applied dropwise into the nose of volunteers.

Pre-Clinical Studies in Mice and Non Human Primates
Immunogenicity Studies of the Adenovirus and MVA, Including Challenge Studies, in Mice.

Examine the induction of durable immunity by MVA and Ad vectors (AdCh-NP+M1) expressing NP+M1 individually and in AdCh-NP+M1/MVA-NP+M1 prime-boost immunisation regimes Examine the induction of durable protective immunity in naïve mice by MVA and Ad vectors expressing NP+M1 after single dose immunisation and in AdCh-NP+M1/MVA prime-boost immunisation regime and develop PCR-based monitoring Test vaccines in mice that have been pre-exposed to a heterosubtypic influenza strain, to assess the ability of the vaccines to re-establish protective immunity in pre-exposed mice.

Examine the induction of cross-subtype protection by these vaccines against a highly pathogenic influenza strain.

optimise vaccine delivery via transdermal patches

The ability of replication-deficient adenovirus and MVA vaccines expressing many different antigens to induce T cell responses against the encoded antigens is well known, and there are many examples in the literature of prime-boost regimes using these viral vaccine vectors in mice, as well as in non-human primates and humans. This part of the study will allow us to assess multiple vaccination regimes in mice, to examine the duration of protective immunity, to test heterosubtypic immunity, to identify correlates of protective immunity in mice and to carry out an assessment of the potential of using microneedle patches for transdermal delivery of viral vectored vaccines.

Influenza viruses are not natural pathogens of mice, however an infection localised to the respiratory tract is readily observed within 24 hours of murine infection. Most of the work in murine models to date has utilised prime and challenge experiments using two subtypes of influenza A; A/PR8/34 (PR8, H1N1) and A/HKx31 (HKx31, H3N2) in C57/BL6J or BALB/c mice. HKx31 is relatively avirulent and is a lab reassortant of PR8 and A/HK/168 that expresses HA and NA of A/HK/168 and the six internal genes of the more virulent PR8. This reassorted virus cannot, therefore be neutralised by antibodies to the HA and NA from PR8 (H1N1) and cross-protection is mediated by immunity to the internal antigens. The respiratory challenge model is characterised by an acute, transient and localised pneumonia, with virus clearance by day 10 post-infection. Viremia is localised to the respiratory system and no viral replication is found in other tissues (Doherty and Christensen 2000). Mice infected with PR8 and intranasally challenged one month later with the HKx31 clear the virus 1-2 days before naïve mice and demonstrate only transient weight loss. The mouse influenza respiratory challenge model, using heterosubtypic primary and secondary infections, has been widely used to understand the characteristics of effector and memory $CD8^+$ T cells (Flynn, Riberdy et al. 1999; Doherty and Christensen 2000; Kedzierska, La Gruta et al. 2006). The memory $CD8^+$ T cell population, induced by primary infection, contracts over 3 weeks post-primary infection to 10% of its peak level (Flynn, Riberdy et al. 1999).

This memory population is very stable and is preserved indefinitely, albeit at very low frequencies in the lung, respiratory tract (as measured in bronchoalveolar lavage [BAL]) and lymphoid tissue, with higher levels that have not contracted to the same extent in the spleen (Hogan, Usherwood et al. 2001). The presence of memory $CD8^+$ T cell response generated by primary virus infection or by vaccination can mediate recovery from HKx31 (Flynn, Riberdy et al. 1999), or limited protection against H7N7 infection (Christensen, Doherty et al. 2000) when this challenge occurs one month post-primary infection. Although the memory $CD8^+$ population, generated by a primary virus infection, is maintained for long periods of time, efficacy against heterosubtypic challenge wanes over time; immune mice challenged 20 weeks after primary infection demonstrate similar viral titres in the lung to naïve challenged mice (Liang, Mozdzanowska et al. 1994). Secondary exposure to virus results in massive clonal proliferation and distribution of memory $CD8^+$ T cells to lymphoid and non-lymphoid tissues, including the lung, liver and bone marrow (Flynn, Riberdy et al. 1999; Kedzierska, La Gruta et al. 2006).

The strength of the memory T cell response and its ability to control and clear a secondary challenge may be affected by the choice of route and dose of primary virus (Liang, Mozdzanowska et al. 1994; Flynn, Riberdy et al. 1999). This study will determine, in a murine model, if sufficiently strong and durable T cell responses are induced by vaccination with MVA and simian adenoviruses expressing NP and M1, instead of infection, that will cross-protect against seasonal as well as virulent subtypes of influenza virus, and whether protective immunity can be induced by repeated doses of the same vaccine (homologous boosting) or requires heterologous prime-boost immunisation to achieve protective immunity. This is of relevance to the clinical development of vaccines for use in influenza-naïve individuals.

Examine the Induction of Durable Immunity by MVA and Ad Vectors Expressing NP+M1 in Single Dose and AdCh-NP+M1/MVA-NP+M1 Prime-Boost Immunisation Regimes Initial studies will establish the immunogenicity of a single immunization with the AdCh-NP+M1 and MVA-NP+

M1 vaccines. We will define the most potent homologous adenovirus boosting regime as well as examining heterologous prime-boost vaccine regime of the four heterologous vaccine regimes in naive C57/BL6J mice using the first chimp adenovirus to prime followed by an MVA boost (AdChA/MVA), the second chimp adenovirus with MVA (AdChB/MVA); or heterologous (AdChA/AdChB and AdChB/AdChA) adenovirus prime-boost. Initial immunogenicity experiments will focus on examining, by intracellular cytokine staining and flow cytometry analysis, T cell responses in the spleen and the lung to the NP and M1 antigens in mice vaccinated with the individual vaccines and with prime-boost strategies. We have previously found that adenovirus based vaccines can induce responses to additional $CD4^+$ and $CD8^+$ epitopes that are not detected after immunisation by poxvirus based vaccines. We will examine this by stimulating spleen cells in vitro, from mice immunized with single or prime/boost vaccines, with overlapping peptide pools of the entire NP and M1 antigens and elucidating the breadth and dominance of the immune response. The magnitude and kinetics of T cell effector and central memory induced by vaccination will be assessed by flow cytometry using commonly used phenotypic markers, for example, CD27, CD43, CD62L, CCR7, CD127 and IL-2. Examine the Induction of Durable Protective Immunity by MVA and Ad Vectors Expressing NP+M1 in Single Dose and AdCh-NP+M1/MVA-NP+M1 Prime-Boost Immunisation Regimes and Develop PCR-Based Monitoring The induction of protective immunity by the individual viral vectored vaccines and by prime-boost regimes will be assessed in naïve mice. We will compare the protection induced by these vaccines to the well characterised heterosubtypic influenza virus challenge model (Doherty and Christensen 2000), using strain A/HKx31 (HKx31, H3N2) to infect mice. Stringent challenge studies will be performed using an intranasal inoculation of a high dose ($2 \times 10^6$ $TCID_{50}$/mouse) of influenza virus, strain A/PR8/34 (PR8, H1N1) one month post-vaccination or post-infection with a primary heterosubtypic infection using strain A/HKx31 (HKx31, H3N2).

We will examine the durability of protection by performing the challenge 10-15 weeks post-vaccination or post primary infection. Protection against challenge will be monitored by measuring virus titres in the lung in the acute phase post-challenge (days 1-14). We will also examine the expansion and phenotype of T cell populations post-challenge and their re-distribution to BAL and lung. Spleens, mediastinal lymph nodes and BAL will be sampled at the same time as lungs are harvested for virus titration assays post-challenge. We will investigate if vaccination results in a faster appearance of antigen-specific T cells ($CD4^+$ and $CD8^+$) in the BAL and mediastinal lymph nodes compared to primary virus infection, which generally infiltrate the lung by day 5-7 days after intranasal influenza infection (Flynn, Riberdy et al. 1999). Lung virus titres, from tissues harvested on days 1-12 will be used to measure virus clearance in infected mice. In some experiments, lung tissue sections from challenged immunized mice will be examined histologically for any signs of immune-pathology, a theoretical risk of very potent $CD8^+$ T cell responses to influenza virus.

Quantitative real-time PCR of viral genomes will be established as an alternative method to traditional virus titration methods in Madin-Darby canine kidney (MDCK) cells as a measure of virus infection. Initial experiments will standardise these methods, in a similar fashion to previous publications in the stringent challenge model system (Atmar, Baxter et al. 1996). We have previously demonstrated that a quantitative PCR method for monitoring malaria infection is highly sensitive and can be translated to large clinical studies in the field (Andrews, Andersen et al. 2005). This task will therefore a) identify vaccine regime(s) that induce durable protection in naïve mice against a stringent challenge with influenza virus subtypes that are commonly used as a model of human infection b) establish the kinetics of virus infection and clearance in vaccinated, naïve and pre-exposed mice, c) identify correlates of vaccine-induced protection and d) verify and standardise a fast, robust method of monitoring virus infection and clearance that can be translated to other influenza challenges described herein.

In initial challenge experiments the standard deviation and significance level will be assessed and power calculations will be performed to identify the sample size required to detect an 80% vaccine efficacy compared to control, unvaccinated mice. We shall seek to minimise the numbers of animals used while using adequate numbers to allow statistically significant data to be obtained, maximising the amount of useful data from each animal. This immunogenicity and challenge study should therefore add valuable knowledge about the capacity of these MVA and adenovirus based vaccines to induce specific immune phenotypes and how vaccine-induced T cell subsets contribute to preventing or clearing a respiratory tract infection.

Test Vaccines in Mice that have been Pre-Exposed to a Heterosubtypic Influenza Strain, to Assess the Ability of the Vaccines to Re-Establish Protective Immunity in Pre-Exposed Mice.

Most pre-clinical influenza vaccine immunogenicity and challenge studies are assessed in naïve mice which may not accurately reflect the clinical situation of immunising adults who posses memory T cell responses to influenza. We will examine these issues and compare our findings with those generated by the clinical trials decribed in this application, with the aim of optimisimg a mouse model suitable for testing the ability of vaccines to boost T cell responses acquired by natural exposure. A pre-exposure model will be established in task 2. Mice will be intranasally infected with a low dose of influenza A strain HKx31 as a model of natural human pre-exposure. T cell responses in the spleen, mediastinal lymph nodes and lung will be assessed at short (10 days) and long (8 and 15-20 weeks) times after infection to establish a baseline immune response after primary infection. HKx31-immune mice will be mucosally challenged with a high dose of PR8 at 8, 15 and 20 weeks to establish when protection is lost. This will establish the longevity of protection against heterosubtypic challenge; according to published findings, protection against challenge in some model systems is lost at approximately 20 weeks after primary infection (Liang, Mozdzanowska et al. 1994). In this task, pre-exposed mice will be vaccinated with the individual vaccines and with the most immunogenic prime-boost regime at the time when protection has waned.

Effector and memory T cell responses will be examined 2 and 8 weeks post-immunization in the manner described for naïve mice. The magnitude and phenotype of T cells in lung and BAL tissue will also be analysed. In comparison to naïve mice, it is expected that the magnitude of the response in all tissues will be higher in pre-exposed mice and responses should be detected in the lung and BAL tissue. Pre-exposed, vaccinated mice and pre-exposed unvaccinated mice will be stringently challenged with influenza A strain PR8 at 8 or 20 weeks post-immunization to identify the protective efficacy and durability of these vaccine regimes. Finally, we will correlate the phenotype of the responding T cells and their lymphoid or non-lymphoid distribution with protection against heterosubtypic challenge in pre-exposed and naïve vaccinated animals to define a correlate of protection within the T cell compartment. The result of this study will demonstrate which vaccine(s) can induce protective, durable, immunity in a pre-exposure setting.

Examine the Induction of Cross-Subtype Protection by these Vaccines Against a Highly Pathogenic Influenza Strain.

A highly efficacious cross-subtype vaccine would be a powerful tool to combat an influenza epidemic or pandemic. In this study, we will examine the capacity of MVA-NP+M1 and AdCh-NP+M1 based vaccines to protect mice against a highly virulent influenza A challenge. Equine influenza viruses display high virulence in mice, comparable to that resulting from avian influenza (H5N1) infection (Epstein, Kong et al. 2005), however, equine influenza viruses may be handled at a bio-safety level 2 facility, compared to bio-safety level 3+ for avian influenza (Christensen, Doherty et al. 2000; Epstein, Kong et al. 2005). We therefore plan to determine if the most promising vaccine, that demonstrates the strongest efficacy in naïve and pre-exposed animals, can also induce protective immunity against highly virulent equine influenza. Morbidity and mortality will be used as endpoints in an initial study. In a follow-up study, control of virus replication and clearance of virus will be examined in mice immunised with the most protective vaccine regime, identified in the initial experiment.

Vaccine Delivery Via Transdermal Patches

The viral vectored vaccines to be used in this study are administered by intradermal or intramuscular injection. However, we will also assess using transdermal patches to deliver these vaccines. This method of delivery has the potential to greatly simplify vaccine delivery. It is envisaged that ultimately pre-prepared patches could be manufactured with the vaccine loaded onto the patches. In order to use them they would then be applied to the skin of the vaccinee, making them suitable for use in children or in areas where there is a shortage of healthcare professionals able to give injections. Transdermal delivery of DNA plasmids has been shown to be possible using custom designed microneedle patches. These microneedle arrays are fabricated from silicon or polymer and are typically 90-290 μm in length; sufficient to penetrate the impermeable stratum corneum, the outer skin layer, without being too deep to penetrate the pain receptors in the dermis. When the microneedle patch is applied to the skin, micro-channels are created that permit drugs and DNA plasmid vaccines to bypass the stratum corneum. It has been shown that the antigen encoded by the DNA delivered transdermally is expressed in ex vivo human skin (Birchall, Coulman et al. 2005). In preliminary studies that we have performed, we have observed similar in vivo observations using virus vectors, demonstrating that transdermal delivery has great potential as a simple, effective vaccination strategy. It is known that both adenovirus and MVA vectored vaccines are highly immunogenic when delivered intradermally, making them particularly suitable for this type of delivery. Initial studies will compare the immune responses in mice immunised by transdermal patch or intradermal immunisation, using both types of viral vaccine vector. A clinical study could then be carried out to replicate the findings in humans.

Immunogenicity Studies of the Adenovirus Vaccines Boosted with the Heterologous Adenovirus or with MVA in Non Human Primates The immunogenicity studies will be performed in Rhesus macaques. We will follow a two-step approach. This will permit us to reduce to the minimum the number of experimental animals. Moreover, we will have the possibility to compare 2 different Ad vectors and 3 different heterologous prime-boost strategies with only 5 groups of 3 macaques.

In Step 1 we will perform a two-dose response study with each of the two different AdCh-NP+M1 vectors (AdChA-NP+M1; AdChB-NP+M1). All the experiments will be conducted in healthy animals that will be pre-evaluated for the presence of pre-existing immunity against Ad vectors. The immunization schedule will be based on two intramuscular injections at week 0, and 4 of each of the two vectors, administered at doses of $10^9$ and $10^{10}$ pp of each vector:

12 Rhesus macaques will be enrolled and divided into 4 groups of 3 animals:

- Group 1 will include 3 animals that will receive the AdChA-NP+M1 at $10^9$ total viral particles/dose at week 0 and 4
- Group 2 will include 3 animals that will receive the AdChA-NP+M1 at $10^{10}$ total viral particles/dose at week 0 and 4
- Group 3 will include 3 animals that will receive the AdChB-NP+M1 at $10^9$ total viral particles/dose at week 0 and 4
- Group 4 will include 3 animals that will receive the AdChB-NP+M1 at $10^{10}$ total viral particles/dose at week 0 and 4

Immunogenicity follow-up will be performed at 2, 4, 6, 8 weeks following the first vaccination. These data will tell us which is the Most Potent AdCh-NP+M1 vector.

In Step 2, we will use the Most Potent vector for the experiment with MVA, at the highest dose:

- Group 5 will include 3 animals that will receive the Most Potent AdCh-NP+M1 at $10^{10}$ total viral particles/dose at week 0 and 4 and MVA at $2\times10^8$ pfu/dose at week 24

Immunogenicity follow-up will be performed at week 0, 4, 8, 12, 18, 24, 27, 32, 40, and 48 following the first vaccination. The most crucial immunogenicity testing will be at 2, 4, 6, 8, 27 weeks. The peak effector response occurs one week after MVA boosting, hence testing will be done at 27 rather than 28 weeks in this experiment.

In parallel, we will boost the groups primed in Step 1 with the heterologous AdCh-NP+M1 at the highest dose at week 24:

- The 3 animals in Group 1—that received the AdChA-NP+M1 at $10^9$ total viral particles/dose at week 0 and 4—will receive AdChB-NP+M1 at $10^{10}$ total viral particles/dose at week 24
- The 3 animals in Group 2—that received the AdChA-NP+M1 at $10^{10}$ total viral particles/dose at week 0 and 4—will receive AdChB-NP+M1 at $10^{10}$ total viral particles/dose at week 24
- The 3 animals in Group 3—that received the AdChB-NP+M1 at $10^9$ total viral particles/dose at week 0 and 4—will receive AdChA-NP+M1 at $10^{10}$ total viral particles/dose at week 24
- The 3 animals in Group 4—that received the AdChB-NP+M1 at $10^{10}$ total viral particles/dose at week 0 and 4—will receive AdChA-NP+M1 at $10^{10}$ total viral particles/dose at week 24

Immunogenicity follow-up will be performed at week 12, 18, 24, 26, 28, 32, 40, and 48 following the first vaccination. In this case, the most crucial immunogenicity testing will be at 24, 26, 28 weeks.

Animals will be bled prior to vaccination to isolate sufficient PBMCs and sera in order to use as baseline samples to run during the course of the study so that vaccine responses can be best assessed compared to a baseline. Viral vector (adenovirus serology) screening will also be performed prior to vaccination.

Testing will include the following assays: ELISA, IFNγ ELIspot, IFNγ Intracellular Cytokine Staining (ICS), MHC Class I Tetramer, T cell proliferation.

Immunopathology Studies Following Influenza Virus Challenge in Rhesus Macaques

The aim of this part of the study is to examine the safety of the presence of a strong T cell response to influenza antigens at the time of infection with influenza. The immunopathology evaluation will be performed in rhesus macaques. We will compare vaccine safety, the development of cellular immune responses (ICS), viral shedding and pathology in respiratory tissues in three groups of animals. All experiments will be conducted in healthy animals pre-screened for the absence of immune responses to the viral vectors to be used (AdCh as well as MVA). Two vaccination regimens will be evaluated as well as a non-vaccinated control group.

Group 1 will include 6 animals that will receive two intramuscular injections of AdCh-NP+M1 at weeks 0 and 4 with an optimal immunogenic dose as established in the immunogenicity studies. These animals will be boosted with MVA-NP+M1 at week 24 (Highly immunogenic regime).

Group 2 will include 6 animals that will receive two intramuscular injections of AdCh-NP+M1 at weeks 20 and 24 with an optimal immunogenic dose as established in the immunogenicity studies (moderately immunogenic regime).

Group 3 will include 6 animals that will not receive injections (no response to flu antigens).

Immunogenicity will be assayed on ex vivo stimulated cells by intracellular cytokines and surface marker staining. The following will be included: CD3, CD4, CD8, IFN-γ, IL-2, IL-5, IL-10, IL-17, TNF-α, perforin and granzyme. Immunology evaluations for groups 1 and 3 will be performed on samples taken at weeks 0, 2, 4, 6, 20, 24, 26 and at sacrifice. For group 2 Immunology evaluations will be done on samples obtained at weeks 20, 24, 26 and at sacrifice Safety will be evaluated at each immunisation by inspection of the injection sites (erythema and oedema) as well as clinical chemistry (kidney, liver, proteins and electrolytes) and haematology (red cell count, white blood cell count and differentiation). Samples for clinical chemistry and haematology will be taken at the time of vaccination and 1 day following vaccination, inspection of the injection sites will also be performed at these time-points.

All animals will be challenged by intratracheal instillation of $10^7$ TCID of challenge virus at week 26.

Nasal and pharyngeal swabs will be collected at days 2, 4 and 10 following challenge. The swabs will be assayed for virus titre using standard virological methods.

All animals will be sacrificed on day 10 following infection, a full necropsy will be performed with special attention on respiratory pathology. Histological slides will be prepared from a variety of respiratory tissues (nasal, pharyngeal as well as several samples from the lungs) and assessed by a trained veterinarian pathologist.

Clinical Studies with AdCh and MVA Vaccines

Phase I Dose Escalation with AdChNP+M1 This will examine safety and immunogenicity of AdChNP+M1 in humans and will also serve to determine the dose to be used in the Phase IIa study described below. This study will follow the same approach as that planned for a Phase I dose escalation study with AdCh63 expressing a malaria antigen. Both studies will take place at the Centre for Clinical Vaccinology and Tropical Medicine, Oxford, where many other Phase I and Phase IIa studies have been successfully conducted. The malaria vaccine study will be a First Time In Man study for a replication-deficient simian adenovirus vectored vaccine. Regulatory and ethical approval are currently being sought for this study (as of April 2007) although following preliminary discussions with the MHRA it is expected that permission will be granted. The study is expected to take place during the second half of 2007. Should any further information or safety measures be required, this information will be taken into account when applying for permission for the AdChNP+M1 study, and safety data from the malaria vaccine study will be used to support the 'flu vaccine study.

Study Groups

This will be an open label Phase 1 dose escalation study in healthy volunteers. There will be 4 study groups, each containing 8 volunteers. Recruitment of groups will be sequential.

Observations

Observations which will be documented are pulse, blood pressure and temperature.

Blood Tests

Blood will be drawn for the following laboratory tests:

1. At the Oxford Radcliffe Hospitals NHS Trust Laboratories, using NHS standard procedures:
   Haematology; Full Blood Count
   Biochemistry; Sodium, Potassium, Urea, Creatinine, Albumin, Liver Function Tests, Glucose
   Diagnostic serology; Adenovirus antibodies, HBsAg, HCV antibodies, HIV antibodies (Counselling will be given prior to testing blood for these blood-borne viruses)
   Immunology; Human Leucocyte Antigen (HLA) typing
2. At University of Oxford research laboratories:
   Exploratory Immunology; Ex vivo Elispot assays for interferon gamma will be performed. Other exploratory immunological assays, including Elispot assays for interleukin-2, flow cytometry assays, antibody assays and tumour necrosis factor alpha, may be performed at the discretion of the investigators. These may include gene expression studies.

Urinalysis

Urine will be tested for protein and glucose at screening. For female volunteers only, urine will be tested for beta-human chorionic gonadotrophin (HCG) at screening and immediately prior to each vaccination.

Vaccinations

Before each vaccination, the on-going eligibility of the volunteer will be reviewed. The vaccine will be administered, the injection site will be covered with a sterile dressing and the volunteer will stay in the CCVTM for half an hour, in case of immediate adverse events. Observations will be taken 30 minutes after vaccination and the sterile dressing removed and injection site inspected. An oral thermometer, tape measure and diary card will be given to each volunteer, with instructions on use.

Group 1 will receive a single dose of $1 \times 10^8$ vp.
Group 2 will receive a single dose of $1 \times 10^9$ vp.
Group 3 will receive a single dose of $1 \times 10^{10}$ vp.
Group 4 will receive a single dose of $5 \times 10^{10}$ vp.

Following new MHRA guidelines, in each group, the first volunteer will be vaccinated 48 hours prior to any other volunteer to avoid a previously unsuspected severe adverse event affecting multiple volunteers. The volunteer will be vaccinated intradermally then observed for 30 minutes prior to discharge. We will review this volunteer at 48 hours and then, provided there are no safety issues we will vaccinate 2 further volunteers from this dosage group. These volunteers will be reviewed after 48 hours. If there are still no safety issues we will then vaccinate the remaining 5 members of the cohort. All volunteers will be issued with the telephone and pager number of the investigators and encouraged to contact the investigators if there are any problems. Investigators will be available 24 hours a day.

The effector and memory T cell response to NP and M1 antigens will be determined using overlapping peptides in Elispot assays (both ex vivo and on cultured cells) in the volunteer screening blood sample and in a further sample taken on the day of immunisation. Follow up visits will take place on days 2, 14, 28, 90. The volunteers will be assessed for local and systemic adverse events, using a diary card, interim history, physical examination and blood tests at the time points indicated in the schedule of attendances. Blood will also be taken for exploratory immunology analysis, including ex vivo and cultured IFN-γ elispot assays as well as flow cytometry. Substantial progress has been made towards full GCLP quality assays for these T cell responses. For selected epitopes, HLA class I types tetramers are available and these will be used to phenotype the induced CD8+ T cells. We shall evaluate subtype crossreactivity by pooling peptides that are completely conserved between the H3N2, H1N1 and H5N1 subtypes and making subtype specific pools to allow quantitation of subtype crossreactivities.

Safety will be assessed by the frequency, incidence and nature of adverse events and serious adverse events arising during the study. After each dose interval a safety review will be held. This will be internal and consist of a review of all adverse effects in volunteers before proceeding to the next dose interval. Finally, the safety and immunogenicity data will be reviewed and a dose for the phase IIa study will be chosen.

Two Phase IIa influenza challenge studies are described here, each employing a single vaccination with either MVA-NP+M1 or AdChNP+M1, at the dose determined during the phase I studies for each vaccine.
Challenge Studies The concept of infection of volunteers was initiated at the Common Cold Unit, Salisbury in 1948 (Tyrrell and Fielder 2002). Groups of 20-30 volunteers were housed in detached warden buildings and were physically isolated from both staff and co volunteers. A quarantine unit in London able to infect up to 100 volunteers (Fries, Lambkin et al. 2004) has been established.

The protective efficacy of the MVA-NP+M1 and AdCh-NP+M1 vaccines will be tested in a human challenge study. The analysis of this trial should provide proof of principle.

A clinical trial protocol will be prepared for the entire study, incorporating information from the phase I trials with the two vaccines. Ethical and regulatory approval will be obtained from the relevant (local) ethics committee and the national licensing agency, the Medicines and Healthcare products Regulatory Agency. For each study, 30 healthy young volunteers will be recruited. These will be screened to ensure low anti-'flu antibody titres. Volunteers will be given either a single dose of the vaccine (dose determined during the phase I studies) or of a placebo, then challenged with 0.50-0.75 human infectious dose 2 weeks later. This will produce clinical symptoms in approximately 50-75% of volunteers. Full clinical signs, systemic and local symptoms will be monitored.

Blood and oral fluid samples and throat swabs for virus recovery will be taken daily pre (nasal wash samples) and post challenge (e.g. 9-10 days). The blood, nasal wash and oral fluid samples will be used in the most relevant immunological tests identified during the phase I studies. T cell and antibody responses to all influenza antigens will be measured in all volunteers, to gain a greater understanding of the acute immune response to 'flu infection.

Serological assays (e.g. HI, SRH, VN, MN, ELISA) will be conducted.

All volunteers will be treated with oseltamivir at the completion of the trial and will be recalled to the unit 2 weeks and 6 months later for medical checks and blood, nasal wash and oral fluid samples will be collected to investigate the immune response using appropriate immunological assays.

Clinical data and immunological samples from these studies will be used to evaluate the protective efficacy of the new vaccines. The clinical trials will bridge the gap between pre-clinical and clinical studies and allow proof of principle testing in humans. By analysing the data obtained we will be able to assess the ability of a T cell response to NP and M1 to reduce both viral shedding and disease symptoms. These data will allow us to assess the impact the new vaccines could have if widely deployed.

Example 8: Clinical Batch Manufacture and Testing

Clinical batch has been manufactured. Quality control testing reveals that it meets expectations. We present the results of various assays conducted.

In particular this example presents a MVA-NP+M1 identity and purity assay.

MVA-NP+M1 was manufactured by IDT as disclosed herein. In this example the test sample was Lot 010907, (wet fill) vial 12.
Experimental:

PCR assays were carried out to determine the identity and purity of the IDT manufactured (lot 010907) clinical batch of MVA-NP+M1 vial 12.
Procedure:

The assays were performed according to SOP FM001. Three PCR reactions, to detect either NP+M1, or Red fluorescent protein (RFP), or wild type virus, were each carried out on five samples.

|  |  | Expect PCR product with | | |
|---|---|---|---|---|
| Sample | Description | wt | RFP | NP+M1 |
| Test sample | Test sample | − | − | + |
| Wild type MVA | Control | + | − | − |
| MVA-Red | Control | − | + | − |
| MVA-NP+M1 | Control | − | − | + |
| Sterile distilled water | Control | − | − | − |

FIG. 5 shows the results of the PCR experiments.

Example 9: Immunogenicity of Clinical Batch

The clinical batch of MVA-NP+M1 manufactured as above was examined using an immunogenicity assay. In more detail, MVA-NP+M1 manufactured by IDT Lot 010907, (wet fill) vial 12 was tested.
Experimental:

A mouse IFN-γ ELISPOT was carried out to determine the immunogenicity of the IDT manufactured (lot 010907) clinical batch of MVA-NP+M1 vial 12.
Procedure:

Four mice were vaccinated intradermally with $10^7$ pfu of MVA-NP+M1 (wet-fill) produced by IDT Lot no 010907.

Fourteen days later the mice were sacrificed and the spleens harvested for an IFN-γ ELISPOT assay performed according to SOP FM003.

Background was defined as the number of spot forming cells (SFCs) per million splenocytes observed when cells were stimulated with 10% MEM (MEM+10% FCS+1% L-Glut+1% Pen-strep) only.

Results:

Cells were plated in duplicate for each mouse and wells containing $5 \times 10^5$ cells were counted. This was then used to calculate the mean SFCs/million splenocytes.

|  | Media | Flu peptide | Net Flu |
|---|---|---|---|
| M1 | 32 | 219 | 187 |
| M2 | 51 | 190 | 139 |
| M3 | 56 | 257 | 201 |
| M4 | 37 | 246 | 209 |
| Average | 44 | 222 | 184 |
| SD | 11 | 30 | 31 |

Conclusion:

The potency assay demonstrated that IDT manufactured Lot 010907 elicited a strong immune response, with the mean number of spot forming cells per million splenocytes in the ELISPOT assay greater than 15, with not more than 1 non-responding mouse of four tested. The lower limit of detection of the assay is 5 spots per million splenocytes. Exemplary data are shown in FIG. 6.

Example 9: Further Immunogenicity Studies

We also demonstrate immune responses to epitopes in both NP and M1 in mice.

In this example, single dose $10^6$ pfu was used. Administration was intradermal.

Immune responses were assessed by spleen ELISPOT at 14 days:

```
NP: TYQR-            (SEQ ID NO: 6)
    TRALV

M1: LYRKLKREI        (SEQ ID NO: 5)
```

Results are shown in FIG. 7 which illustrates that immune responses to specific epitopes within the different composite parts (NP/M1) of the immunogen are generated according to the present invention.

Example 10: Further Clinical Studies

First volunteer to be vaccinated 24 h before continuing with the rest of the group Further volunteers vaccinated on the same day may be vaccinated from the same vial (in group 1)
  the maximum number vaccinated from one vial is likely to be 3
Each group will likely be vaccinated over a period of several weeks
  due to recruitment limitations
  we now suggest a maximum of three vaccinees per day for added safety
Four clinical research fellows and a research nurse are available if several volunteers are available on the same day
  delegation log will be used Test for wt MVA is included in QC
Preparation of primary CEFs is standard in vaccine manufacture and complete QC is included on cells as well as virus.
GLP two dose tox study
each dose is $1.5 \times 10^7$ pfu
the IMP was well tolerated
no animals showed any adverse reactions to the IMP
Only North American FCS used in preparing the recombinant virus
no FCS used during GMP manufacture
Volunteers will not be tested for current 'flu A infection.

Example 11: Phase IIa Study

When the phase I trial demonstrates good safety and immunogenicity of MVA-NP+M1
future vaccination and challenge study follows (Phase IIa)
Dose for phase IIa chosen based on results of phase I
Volunteers to be screened for low anti-flu antibodies, controls and vaccinees challenged with H3N2
Ab and T cell responses to all flu antigens to be monitored in all participants before and after challenge
Phase IIb (infection by natural exposure) may also be conducted.

Example 12: Immunogenicity Throughout Immunogen

Experiments similar to those presented in preceding examples (such as examples 8 and 9) were carried out on a complete set of overlapping peptides in mice.

Identification of Novel T Cell Epitopes Induced by MVA-NPM1:

We have demonstrated that the MVA-NPM1 vaccine can induce T cell responses to dominant T cell epitopes in NP and M1. To examine the breadth of the immune response and to examine if this vaccine can induce T cell responses to novel epitopes, C57/BL6 or Balb/c female mice were immunized with $1 \times 10^7$ pfu/ml MVA-NPM1. The breadth of the immune response was assessed two weeks after a single immunization by restimulating spleen cells with a matrix of overlapping peptide pools (Tobery et al., J. Imm. Methods, 2001, 254, 59-66) in an IFN-γ ELISPOT assay. In addition to previously tested epitopes (see above) in Balb/c mice, 12 epitopes in NP and 8 epitopes in M1 were recognised by T cells from MVA-NPM1 immunized mice. In C57/BL6 mice T cells responded to 4 epitopes in NP and 2 epitopes in M1.

The results of this matrix experiment demonstrate in two different strains of mice that (i) the NPM1 construct is immunogenic, (ii) a broad T cell response is induced and (iii) a T cell response is induced to both the NP and M1 proteins. Thus the effectiveness of the invention is demonstrated.

The data demonstrate that the invention produces a broad response against both antigens in two strains of mice.

Thus overall the data presented herein on the clinical product of the invention demonstrate excellent immunogenicity, show that the sequence of the insert is confirmed, demonstrate the presence of antigen and absence of wild type MVA confirmed, and illustrate that the vaccine is genetically stable.

Example 13: A Phase I Study to Assess the Safety and Immunogenicity of a New Influenza Vaccine Candidate MVA-NP+M1 in Healthy Adults Study Code: Flu001
Eudract Number: 2007-003970-24
Ethics Number: GTAC 143

Synopsis

| | |
|---|---|
| Trial Title | A phase I study to assess the safety and immunogenicity of a new influenza vaccine candidate MVA-NP+M1 in healthy adults. |
| Trial Centre | Centre for Clinical Vaccinology and Tropical Medicine (CCVTM) Old Road, Headington, Oxford, OX3 7LJ, UK |
| Trial Identifier | Flu001 |
| Clinical Phase | I |
| Trial Design | Open label observational study |
| Trial Population | Healthy adults aged 18-50 |
| Planned Sample Size | 12 volunteers; 1 dose of $5 \times 10^7$ pfu MVA-NP+M1 day 0 |
| Follow-up duration | Approximately 1 year (This is an estimate and may vary in accordance with the specified time windows for each attendance.) |
| Planned Trial Period | 2 years (1 year following enrolment of last volunteer) |
| Primary Objective | To assess the safety of a new influenza vaccine, MVA-NP+M1, when administered as a single dose to healthy volunteers. |
| Secondary Objective | To assess the cellular immune response generated by a new influenza vaccine, MVA-NP+M1, when administered as a single dose to healthy volunteers. |
| Investigational Products | MVA-NP+M1 |
| Form | Liquid |
| Dose | $5 \times 10^7$ pfu |
| Route | Intradermal injection in the deltoid region of the arm |

Abbreviations

AE Adverse event
CCVTM Centre for Clinical Vaccinology and Tropical Medicine
CRF Case Report Form
ELISPOT Enzyme-linked immunospot
FBC Full blood count
GCP Good Clinical Practice
GMO Genetically modified organism
GTAC Gene Therapy Advisory Committee
HA Haemaglutinin
HBsAg Hepatitis B Surface Antigen
HCG Human Chorionic Gonadotrophin
HCV Hepatitis C virus
HIV Human immunodeficiency virus
HLA Human leukocyte antigen
IDT Impfstoffwerk Dessau-Tornau
IEC Independent Ethics Committee
LSM Local safety monitor
M1 Matrix protein 1
MHRA Medicines and Healthcare products Regulatory Agency
MVA Modified Vaccinia Virus Ankara
MVA-NP+M1 recombinant modified vaccinia virus Ankara expressing influenza nucleoprotein fused to matrix protein 1
NA Neuraminidase
NHS National Health Service
NP Nucleoprotein
pfu Plaque forming units
SAE Serious adverse event
SOP Standard Operating Procedure
SUSAR Suspected unexpected serious adverse reactions

Background and Rationale

The Need for a New Vaccine Against Influenza

Seasonal influenza has a huge annual impact worldwide, accounting for tens of millions of illnesses, hundreds of thousands of excess hospitalizations, and tens of thousands of excess deaths in the US alone [1]. Recent infections of avian influenza (H5N1) in humans could lead to a new pandemic if the virus acquires the ability to transmit between humans, with potentially devastating effects across the world [2]. Current widely-used vaccines for seasonal influenza A act by stimulating production of antibodies to HA and NA. As these proteins are highly polymorphic, there is very little or no cross-subtype (or heterosubtypic) protection and limited cross-strain protection even within subtypes. Each year a selection of highly prevalent strains are chosen as the basis for vaccine production, for a vaccine that will be used for one season only. This need for constant redesign and remanufacture increases the cost of the vaccines, places limitations on supply [3], and most importantly means that vaccines for newly arising strains can only be produced once the HA and NA sequences of viruses posing the greatest threat to human health have been identified.

Two recent trials of new investigational H5N1 vaccines [4, 5] suggested that a 12 fold greater amount of antigen would be need per vaccine course than with other flu vaccines. This has discouraged further development of vaccines by companies who are concerned that if a pandemic does not occur they will be left with unsold supplies, although other trials have found that the use of adjuvants can reduce the amount of antigen needed [6]. Moreover, the current high rate of diversification of H5N1 strains suggests that vaccines made now may differ so much in their H5 sequence from any pandemic strain that emerges that these vaccines would have little or no efficacy. Avian influenza in humans is currently treated with the anti-viral drug oseltamivir, and this drug is now being stockpiled for use in future pandemics. However, oseltamivir resistant H5N1 virus has now been isolated following human infection [7], so the use of this drug alone may not be sufficient to treat infected individuals and limit the spread of the virus should it become transmissible from human to human.

The Development of a Novel Vaccination Strategy Against Influenza

Antibodies against the external proteins of influenza can prevent the virus from infecting cells and either prevent infection or limit the spread of infection. However the surface proteins are highly variable and there is little antibody cross-reactivity between variants. Once a cell has been infected with the virus, it is then vulnerable to T cell attack resulting in the destruction of infected cells so that no more virus can be produced and the infection is controlled. There is evidence from clinical trials of influenza challenge [8], and animal models [9] that T cell responses can protect in the absence of antibodies. Additionally, since T cells can recognise the highly conserved internal proteins of influenza, cross-subtype protection can be achieved [10].

Seasonal influenza infection results in a T cell response to the virus which can protect against subsequent infection. Recent studies in Oxford have shown that 90% of the adult population have detectable T cell responses to one or more influenza antigens (Tao Dong, unpublished). However over the course of a few years these responses decline below protective levels. The new vaccine being tested in this study is designed to boost these T cell responses back to protective levels. Even responses that may be too low to be reliably quantified by currently available assays may still be boosted to high levels by a single dose of recombinant MVA as shown by the tuberculosis vaccine study [11]. Since the internal proteins vary little between influenza subtypes, this could result in a 'universal' vaccine against influenza A. If the need to continually reformulate the vaccine in response to mutations in the viral coat proteins can be removed, the universal vaccine could be produced in large amounts and used more widely than the existing seasonal 'flu vaccines, thus protecting the population against currently circulating viruses and new virus types that are at present only found in avian species.

FIG. 8 shows Frequency (A) and Magnitude (B) of T cell responses to influenza antigens in UK adults. Responses to M1 and 2 were tested together, but in the small number of volunteers were these were separated the response was predominantly to M1 rather than M2.

The Inclusion of NP and M1 in a Boosting Vaccine

There is very little polymorphism of NP and M1 between influenza A isolates. NP is 92% identical between H3N2 and H1N1 strains, and 91% identical between H3N2 and H5N1 strains. M1 is 95% identical between H3N2 and H1N1 strains, and 93% identical between H3N2 and H5N1 strains. This low level of variation appears to allow strong T cell cross-reactivity. For comparison, the sequence of TRAP antigen used in our malaria vaccine differs by 8% from the sequence in the challenge strain, and excellent immunological crossreactivity and cross-strain protection was observed [12]. In addition, each of the antigens (NP and M1) is recognised in a T cell assay by more than 70% of the local population (see FIG. 8).

Using Recombinant MVA as a Boosting Vaccine

Recombinant viral vectors, such as poxviruses and adenoviruses, are a particularly effective way of boosting strong T cell responses to the antigen encoded within them. In our tuberculosis vaccine studies we [11] reported exceptionally high T cell responses in BCG-naïve individuals who were immunised with a single low dose of intradermal MVA expressing Antigen 85A. This secreted antigen is completely conserved between *Mycobacterium tuberculosis* and *M. bovis*, and highly conserved between those species and environmental mycobacteria such as *M. avium*. It is likely that the volunteers had been primed to this antigen by prior exposure to environmental mycobacteria, and that the immunisation with MVA 85A then boosted pre-existing memory responses rather than priming a T cell response de novo. Volunteers given BCG followed by MVA85A four weeks later produced even higher T cell responses to Antigen 85A, and these were maintained for longer; at least two years. The same was true of volunteers who had been vaccinated with BCG in the past (median time 18 years prior to MVA vaccination, range 0.5-38 years).

In clinical studies with new malaria vaccines, recombinant MVA was found to boost T cell responses in malaria-naïve subjects who had been primed with either a DNA vaccine or recombinant fowlpox expressing the same antigen [12, 13].

Recombinant Modified Vaccinia Virus Ankara as a Vaccine Vector

The successful worldwide eradication of smallpox via vaccination with live vaccinia virus highlighted vaccinia as a candidate virus for recombinant use. MVA is a highly attenuated strain of vaccinia virus that is unable to replicate efficiently in human cell lines and most mammalian cells [14]. MVA underwent multiple, fully characterised deletions during more than 570 passages through chicken embryo fibroblast cells [15] including deletions in host range genes and genes encoding cytokine receptors. Viral replication is blocked at a late stage of virion assembly, so, importantly, viral and recombinant protein synthesis is unimpaired [16]. This means that MVA is an efficient single round expression vector, incapable of causing infection in mammals. Replication-deficient recombinant MVA has been seen as an exceptionally safe viral vector. It has been administered to more than 120,000 vaccinees as part of the smallpox eradication programme, with an excellent safety record, despite the deliberate vaccination of high risk groups [15]. This safety in man is consistent with the avirulence of MVA in animal models, where recombinant MVAs have also been shown to be protectively immunogenic as vaccines against viral diseases and cancer. Importantly for a vaccine which may eventually be used in a large proportion of the population, recombinant MVAs expressing HIV antigens have been shown to be safe and immunogenic in HIV-infected subjects [17-19]. There are now safety data from many recombinant MVAs expressing HIV, malaria and melanoma antigens that are currently in phase I/II trials in both the UK and Africa [17-24].

Clinical Studies Using Recombinant MVA

MVA85A has been administered (at a dose of $5\times10^7$ pfu) to 57 healthy volunteers in the UK, 21 healthy adults and 8 healthy infants in The Gambia and 24 adults and 8 adolescents in South Africa, with no vaccine-related serious adverse events. In addition to this, MVA85A low dose ($1\times10^7$ pfu) and high dose ($1\times10^8$ pfu) have each been given to 12 volunteers with no vaccine-related serious adverse events. All volunteers have temporary local redness with, typically, a 5 mm central red area with a paler pink surrounding area that ranges in size from about 1-7 mm in diameter and peaks at 48 hours post vaccination. At seven days post vaccination, generally only the central red area remains. This fades over the next few weeks and is not usually apparent at 2 months after vaccination. Febrile symptoms in the first 2 days after vaccination are reported by some volunteers, particularly at higher doses, but are not always accompanied by a measured rise in temperature. A minority of volunteers experienced a mild headache during this period.

MVA85A has also been given to small numbers of adults with latent TB infection or HIV infection. No additional adverse events were reported.

MVA expressing malaria antigens has been used in many studies in the UK and Africa, in adults and children. Adverse events were the same as those reported for MVA-85A; mild or moderate, self-limited local and/or systemic events.

In addition MVA expressing HIV antigens has been administered to 16 chronically HIV-infected adults. Vaccinations were well tolerated and there were no serious adverse events. No breakthrough viraemia occurred after immunisations or throughout follow-up [25]. The same vaccine has been administered to 192 healthy adults [26] and was found to be safe and well-tolerated.

Study Overview

This is an open label phase I study, to assess the safety of a novel influenza vaccine, MVA-NP+M1. All volunteers recruited will be healthy. Twelve volunteers will be administered a single dose of $5\times10^7$ pfu of MVA-NP+M1. Safety data will be collected. The secondary aim of this study will be to assess the cellular immune responses generated by each dose.

Potential Risks

The general risks to participants in this Phase I study are associated with phlebotomy and with vaccination. The volume of blood drawn over the 1-year study period (up to 650 mL) should not compromise these otherwise healthy volunteers. Potential risks include local and systemic reactions, which are described below. As vaccine-related side effects are believed to be related more to the vector used than the specific insert, it is expected that MVA-NP+M1 will have a similar side effect profile to recombinant MVA viruses encoding other antigens.

Local Reactions

Mild tenderness, bruising, light-headedness or, rarely, syncope, may result from venepuncture. Vaccination usually precipitates a local inflammatory reaction. This may include redness, swelling, scaling, tenderness, or itching. In previous studies using recombinant MVA vaccines, these local reactions have spontaneously resolved within weeks.

Systemic Reactions

Systemic reactions that could potentially occur following immunisation with a recombinant MVA vaccine include a flu-like illness with low-grade fever, chills and malaise. In general, it appears that the frequency of systemic side effects in response to recombinant MVA vaccines is affected by a preceding poxvirus vaccination, with the proportion of volunteers experiencing any systemic side effects after the first vaccination being 69%, decreasing to 37% after the second and 22% after a third immunisation. As with any other vaccine, the Guillain-Barré syndrome, (GBS) or immune mediated reactions that can lead to organ damage may occur. However, this has never been seen with a recombinant MVA vaccine. As with any vaccine, serious allergic reactions may occur.

Known Potential Benefits

Volunteers will not benefit directly from participation in this study. However, it is hoped that the information gained from this study will contribute to the development of a safe and effective influenza vaccine regime. The only benefits for participants would be information about their general health status.

Objectives

Primary Objectives

To assess the safety of a new influenza vaccine, MVA-NP+M1, when administered to healthy volunteers.

Secondary Objectives

To assess the cellular immune response generated by MVA-NP+M1, when administered to healthy volunteers.

Investigational Products

The vaccine to be used in this study is MVA-NP+M1.

Vaccine Formulation, Storage and Accountability

MVA-NP+M1 is manufactured under Good Manufacturing Practice conditions by Impfstoffwerk Dessau-Tornau (IDT), Germany. The vaccine is supplied as liquid in glass vials for intradermal administration and are stored, between −70° C. and −90° C., in a locked freezer, at the University of Oxford, Churchill Hospital. All movements of the study vaccines between IDT and the University of Oxford and between the locked freezer and clinic room will be documented.

MVA-NP+M1 Formulation and Dose

Each vial of MVA-NP+M1 contains 600 microliters volume at a concentration of $1.3 \times 10^8$ pfu/ml in 10 mM Tris buffer. The dose of MVA-NP+M1 to be used in this study will be $5 \times 10^7$ pfu.

Vaccine Administration

On vaccination day, vaccine will be allowed to thaw to room temperature and administered within 1 hour. The vaccine will be administered intradermally over the deltoid region of the arm. The investigators will wear gloves and eye protection. Volunteers will stay in the unit for 30 minutes (±10 minutes) after vaccination. During administration of the vaccine, medicines and resuscitation equipment will be immediately available for the management of anaphylaxis.

As volunteers may already have T cell responses to NP and M1, these will be measured by elispot assay on blood taken at both the screening visit and on the day of vaccination, in order to determine the existing responses, and subsequently the increase in T cell responses induced by vaccination.

Minimising Environmental Contamination with Genetically Modified Organisms (GMO)

In order to minimise dissemination of the recombinant vectored vaccine virus into the environment, the inoculation site will be covered with a dressing after immunisation. This should absorb any virus that may leak out through the needle track. The dressing will be removed from the injection site after 30 minutes (±10 minutes) and will be disposed as GMO waste by autoclaving, in accordance with the relevant Standard Operating Procedure (SOP) and current standard UK practice.

Vaccine Labels

The vaccines will be labelled with a box label (FIG. 30) and a vial label (FIG. 31).

Recruitment and Withdrawal of Trial Volunteers

Volunteers

All participants in this study will be healthy adult volunteers, recruited through poster campaign and newspaper adverts.

Informed Consent

All volunteers will sign and date the informed consent form before any study specific procedures are performed. The information sheet will be made available to the volunteer at least 24 hours prior to the screening visit. At the screening visit, the volunteer will be fully informed of all aspects of the trial, the potential risks and their obligations. The following general principles will be emphasised:

- Participation in the study is entirely voluntary
- Refusal to participate involves no penalty or loss of medical benefits
- The volunteer may withdraw from the study at any time
- The volunteer is free to ask questions at any time to allow him or her to understand the purpose of the study and the procedures involved
- The study involves research of an investigational vaccine
- There is no direct benefit for participating
- The volunteer's GP will be contacted to corroborate their medical history The aims of the study and all tests to be carried out will be explained. The volunteer will be given the opportunity to ask about details of the trial, and will then have time to consider whether or not to participate. If they do decide to participate, they will sign and date two copies of the consent form, one for them to take away and keep, and one to be stored in the Case Report Form (CRF). These forms will also be signed and dated by the one of the Investigators.

Inclusion and Exclusion Criteria

This study will be conducted in healthy adults, who meet the following inclusion and exclusion criteria.

Inclusion Criteria

The volunteer must satisfy all the following criteria to be eligible for the study:

- Healthy adult aged 18 to 50 years
- Resident in or near Oxford for the duration of the vaccination study
- Able and willing (in the Investigators' opinions) to comply with all study requirements Willing to allow the investigators to discuss the volunteer's medical history with their General Practitioner For females, a negative pregnancy test on the day of vaccination and agreement to practice effective contraception for the duration of the study.

Agreement to refrain from blood donation during the course of the study

Written informed consent

Exclusion Criteria

The volunteer may not enter the study if any of the following apply:

Participation in another research study involving an investigational product in the 30 days preceding enrolment, or planned use during the study period Prior receipt of a recombinant MVA vaccine Administration of immunoglobulins and/or any blood products within the three months preceding the planned administration of the vaccine candidate Any confirmed or suspected immunosuppressive or immunodeficient state, including HIV infection; asplenia; recurrent, severe infections and chronic (more than 14 days) immunosuppressant medication within the past 6 months (inhaled and topical steroids are allowed)

History of allergic disease or reactions likely to be exacerbated by any component of the vaccine, e.g. egg products Any history of anaphylaxis in reaction to vaccination History of cancer (except basal cell carcinoma of the skin and cervical carcinoma in situ)

History of serious psychiatric condition

Any other chronic illness requiring hospital specialist supervision

Suspected or known current injecting drug or alcohol abuse (as defined by an alcohol intake of greater than 42 units every week)

Seropositive for hepatitis B surface antigen (HBsAg)

Seropositive for hepatitis C virus (antibodies to HCV)

For females, pregnancy, lactation or willingness/intention to become pregnant during the study Any other significant disease, disorder or finding, which, in the opinion of the Investigators, may either put the volunteer at risk because of participation in the study, or may influence the result of the study, or the volunteer's ability to participate in the study.

Any clinically significant abnormal finding on screening biochemistry or haematology blood tests or urinalysis Withdrawal of Volunteers Volunteers may withdraw or be withdrawn for any of the reasons given below. The reason for withdrawal will be recorded in the CRF. If withdrawal is due to an adverse event, appropriate follow-up visits or medical care will be arranged until the adverse event has resolved or stabilised. Any volunteer who is withdrawn from the study may be replaced, if that is possible within the specified time frame. The Local Safety Monitor (LSM) may recommend withdrawal of volunteers (see above).

Discontinuation Criteria

In accordance with the current revision of the Declaration of Helsinki (amended October 2000, with additional footnotes added 2002 and 2004) and any other applicable regulations, a volunteer has the right to withdraw from the study at any time and for any reason and is not obliged to give his or her reasons for doing so. The Investigators may withdraw the volunteer at any time in the interests of the volunteer's health and well-being. In addition the volunteer may withdraw/be withdrawn for any of the following reasons:

Administrative decision by the Investigators

Pregnancy

Ineligibility (either arising during the study or retrospective, having been overlooked at screening)

Significant protocol deviation

Volunteer non-compliance with treatment regime or study requirements

An adverse event which requires discontinuation of the vaccination regimen or results in inability to continue to comply with study procedures (see below)

Contraindications to Vaccination

The following adverse events constitute contraindications to administration of vaccine at that point in time. If any one of these adverse events occurs at the time scheduled for vaccination, the volunteer may be vaccinated at a later date, or withdrawn at the discretion of the Investigators:

Acute disease at the time of vaccination, defined as the presence of a moderate or severe illness with or without fever Temperature of ≥37.5° C. at the time of vaccination (All vaccines can be administered to persons with a minor illness, such as diarrhoea or mild upper respiratory infection, with or without low-grade febrile illness, i.e., temperature of <37.5° C.)

Compliance with Dosing Regime

All doses in this vaccine study will be administered by the one of the Investigators and recorded in the CRF. The study medication will be at no time in the possession of the volunteer and compliance will not, therefore, be an issue.

Pregnancy

Should a volunteer become pregnant during the trial, she will be followed according to the protocol, but in addition will be followed until pregnancy outcome.

Trial Design

Primary and Secondary Endpoints

The specific endpoints for safety and reactogenicity will be actively and passively collected data on adverse events. The specific endpoints for immunogenicity will be markers of cell-mediated immunity.

Study Groups

This is an open Phase 1 study of a recombinant MVA expressing NP and M1 in one group of twelve healthy volunteers.

Duration of Study

Groups 1 and 2

Each volunteer will attend for one vaccination, on the day of enrolment. The follow up visits are as described above ('study visits'), with a final visit approximately one year after enrolment.

Definition of the Start and End of the Trial

The start of the trial is defined as the date of the first vaccination of the first volunteer. The end of the trial is the date of the last visit of the last volunteer.

Treatment of Trial Volunteers

Study Procedures

Procedures will be performed on the visit time points indicated in the schedule of procedures. Additional procedures or laboratory tests may be performed, at the discretion of the Investigators e.g. urine microscopy in the event of positive urinalysis.

Observations

Observations which will be documented are pulse, blood pressure and temperature.

Blood Tests
Blood will be drawn for the following laboratory tests:
1. At the Oxford Radcliffe Hospitals NHS Trust Laboratories, using NHS standard procedures:
Haematology; Full Blood Count
Biochemistry; Sodium, Potassium, Urea, Creatinine, Albumin, Liver Function Tests, Glucose
Diagnostic serology; HBsAg, HCV antibodies, HIV antibodies (Counselling will be given prior to testing blood for these blood-borne viruses)
Immunology; Human Leucocyte Antigen (HLA) typing
2. At University of Oxford research laboratories:
Exploratory Immunology; Ex vivo Elispot assays for interferon gamma will be performed. Other exploratory immunological assays, including Elispot assays for interleukin-2 and tumour necrosis factor alpha, may be performed at the discretion of the Investigators. These may include gene expression studies. Some of this blood will be required for immediate use and the remainder stored for up to 15 years as a future research source, with the consent of the volunteers.

Urinalysis
Urine will be tested for protein and glucose at screening. For female volunteers only, urine will be tested for beta-Human Chorionic Gonadotrophin (HCG) at screening and immediately prior to vaccination.

Vaccinations
Before each vaccination, the on-going eligibility of the volunteer will be reviewed. The vaccine will be administered as described above. The injection site will be covered with a sterile dressing and the volunteer will stay in the CCVTM for 30 minutes (±10 minutes) after vaccination, in case of immediate adverse events. Observations will be taken 30 minutes (±10 minutes) after vaccination and the sterile dressing removed and injection site inspected. An oral thermometer, tape measure and diary card will be given to each volunteer, with instructions on use.

Study Visits
The study visits and procedures will be undertaken by one of the Investigators. The procedures to be included in each visit are documented in the schedules of attendances (tables below). Each visit is assigned a time point and a window period, within which the visit will be conducted. These can be found in the schedules of attendances.

Screening Visit
All potential volunteers will have a screening visit, which may take place up to 90 days prior to vaccination. Informed consent will be taken before screening, as described above ('informed consent'). If consent is obtained, the screening procedures indicated in the schedule of procedures will be undertaken.

Visits for Volunteers
Day 0 Enrolment and First Vaccination
The eligibility of the volunteer will be reviewed at the end of the screening visit and again when all results from the screening visit have been considered. If eligible, a day 0 visit will be scheduled for the volunteer to receive the first dose of vaccine. Volunteers will not be considered enrolled in the study until they have received their first dose of vaccine. The vaccine will be administered in the non-dominant arm. The first vaccine in the first volunteer will be administered at least 24 hours before any subsequent volunteers are vaccinated.

Subsequent Visits (Day 2 and Weeks 1, 3, 8, 12, 24, 52)
On subsequent visits, the volunteers will be assessed for local and systemic adverse events, using a diary card, interim history, physical examination and blood tests at the time points indicated in the schedule of attendances. Blood will also be taken for exploratory immunology analysis.

TABLE

Schedule of Attendances

| Attendance number | S 1 | V 2 | 3 | 4 | 5 | 6 | 7 | 8 | 9 |
|---|---|---|---|---|---|---|---|---|---|
| Timeline (weeks + days) | | 0 | 0 + 2 | 1 | 3 | 8 | 12 | 24 | 52 |
| Window (days) | | | ±1 | ±2 | ±7 | ±7 | ±7 | ±14 | ±28 |
| Inclusion/Exclusion criteria | X | | | | | | | | |
| Informed consent | X | | | | | | | | |
| Medical History | X | (x) | (x) | (x) | (x) | (x) | (x) | (x) | (x) |
| Physical Examination | X | (x) | (x) | (x) | (x) | (x) | (x) | (x) | (x) |
| Urinalysis | X | | | | | | | | |
| β-HCG urine test | X | X | | | | | | | |
| Review contraindications | X | X | | | | | | | |
| Vaccination | | X | | | | | | | |
| Observations | X | X | X | X | X | X | X | X | X |
| Local & systemic events/reactions | | X | X | X | X | X | X | X | X |
| Diary cards provided | | X | | | | | | | |
| Diary cards collected | | | | X | | | | | |
| HLA typing (mL) | | 4 | | | | | | | |
| HBV, HCV, HIV (mL) | 5 | | | | | | | | |
| Haematology (mL) | 2 | | | 2 | | 2 | | | |
| Biochemistry (mL) | 4 | | | 4 | | 4 | | | |
| Glucose (mL) | 4 | | | 4 | | 4 | | | |
| Exploratory immunology | 60 | 60 | 20 | 60 | 60 | 60 | 60 | 60 | 60 |
| Blood volume per visit (mL) | 75 | 64 | 20 | 70 | 60 | 60 | 70 | 60 | 60 |

TABLE-continued

Schedule of Attendances

| Attendance number | S 1 | V 2 | 3 | 4 | 5 | 6 | 7 | 8 | 9 |
|---|---|---|---|---|---|---|---|---|---|
| Cumulative blood volume (mL) | 75 | 139 | 159 | 229 | 289 | 349 | 419 | 479 | 539 |

S screening visit
V vaccination visit
(x) If considered necessary, emphasising any acute complaints Assessment of Scientific Objectives Primary Outcome Measures To assess the safety of a candidate influenza vaccine, MVA-NP+M1 administered as a single dose to healthy adult volunteers. The specific endpoints for safety and reactogenicity will be actively and passively collected data on adverse events.

Secondary Outcome Measures

To assess the immunogenicity of a candidate influenza vaccine, MVA-NP+M1 administered as a single dose to healthy adult volunteers.

Assessment of Safety

Safety will be assessed by the frequency, incidence and nature of adverse events and serious adverse events arising during the study.

Definitions

Adverse Event (AE)

An AE is any untoward medical occurrence in a volunteer, including a dosing error, which may occur during or after study vaccination and does not necessarily have to have a causal relationship with vaccination. An AE can therefore be any unfavourable and unintended sign (including an abnormal laboratory finding), symptom or disease temporally associated with study vaccination, whether or not considered related to study vaccination.

Adverse Drug Reaction (ADR)

An ADR is any untoward or unintended response to a medicinal product. This means that a causal relationship between the study medication and an AE is at least a reasonable possibility, i.e., the relationship cannot be ruled out.

Unexpected Adverse Reaction

An unexpected adverse reaction is where the nature or severity is not consistent with the Investigator's Brochure.

Serious Adverse Event (SAE) or Adverse Drug Reaction

An SAE is an AE that results in any of the following outcomes, whether or not considered related to the vaccine.
  Death (i.e., results in death from any cause at any time)
  Life-threatening event (i.e., the volunteer was, in the view of the Investigators, at immediate risk of death from the event that occurred). This does not include an AE that, if it occurred in a more serious form, might have caused death.
  Persistent or significant disability or incapacity (i.e. substantial disruption of one's ability to carry out normal life functions).
  Hospitalisation, regardless of length of stay, even if it is a precautionary measure for continued observation. Hospitalisation (including inpatient or outpatient hospitalization for an elective procedure) for a pre-existing condition that has not worsened unexpectedly does not constitute a serious AE.
  An important medical event (that may not cause death, be life threatening, or require hospitalization) that may, based upon appropriate medical judgment, jeopardize the volunteer and/or require medical or surgical intervention to prevent one of the outcomes listed above. Examples of such medical events include allergic reaction requiring intensive treatment in an emergency room or clinic, blood dyscrasias, or convulsions that do not result in inpatient hospitalization.
  Congenital anomaly or birth defect.

Suspected Unexpected Serious Adverse Reactions (SUSARs)

A SUSAR is different from an SAE in that it is unexpected and thought to be related to the investigational product. Reports of any SUSAR will be sent to the MHRA and GTAC within 7 days for fatal and life-threatening cases and within 15 days for all other SUSARs. Administration of further vaccines within the trial will be suspended until a safety review is convened.

Expected Adverse Drug Reactions

Expected local reactions to the vaccine will not be recorded as AEs, but will be recorded in the CRFs. These include redness, swelling, scaling, tenderness, or itching.

Expected Serious Adverse Events

No serious adverse events are expected in this study.

Causality Assessment

For every AE, an assessment of the relationship of the event to the administration of the vaccine will be undertaken. An intervention-related AE refers to an AE for which there is a probable or definite relationship to administration of a vaccine. An interpretation of the causal relationship of the intervention to the AE in question will be made, based on the type of event; the relationship of the event to the time of vaccine administration; and the known biology of the vaccine therapy (table below).

TABLE

Guidelines for assessing the relationship of vaccine administration to an AE

| | | |
|---|---|---|
| 1 | No Relationship | No temporal relationship to study product and Alternate etiology (clinical state, environmental or other interventions); and Does not follow known pattern of response to study product |
| 2 | Possible | Reasonable temporal relationship to study product; or Event not readily produced by clinical state, environmental or other interventions; or Similar pattern of response to that seen with other vaccines |
| 3 | Probable | Reasonable temporal relationship to study product; and Event not readily produced by clinical state, environment, or other interventions or Known pattern of response seen with other vaccines |

TABLE-continued

Guidelines for assessing the relationship of vaccine administration to an AE

| | | |
|---|---|---|
| 4 | Definite | Reasonable temporal relationship to study product; and Event not readily produced by clinical state, environment, or other interventions; and Known pattern of response seen with other vaccines |

Reporting Procedures for all Adverse Events

All AEs occurring during the, observed by the Investigators or reported by the patient, whether or not attributed to study medication, will be reported in the CRF. All AEs that result in a patient's withdrawal from the study or that are present at the end of the study, will be followed up until a satisfactory resolution occurs, or until a non-study related causality is assigned. All deaths occurring during the study will be reported to the Sponsor. For all deaths, available autopsy reports and relevant medical reports will be made available for reporting to the relevant authorities. The severity of events will be assessed according to the scales in the table below.

TABLE

Scale for assessing the severity of AEs

| Scale | Description | Definition |
|---|---|---|
| 0 | | Absence of the indicated symptom |
| 1 | Mild | Awareness of a symptom but the symptom is easily tolerated |
| 2 | Moderate | Discomfort enough to cause interference with usual activity |
| 3 | Severe | Incapacitating; unable to perform usual activities; requires absenteeism or bed rest |
| 4 | Serious | Life-threatening |

Reporting Procedures for Serious Adverse Events

In order to comply with current regulations on serious adverse event reporting to Health Authorities, the event will be documented accurately and notification deadlines respected. SAEs will be reported to an internal safety group, within 1 working day of the Investigators being aware of their occurrence, as described in internal SOP-TC009. SAEs will not normally be reported to GTAC, unless there is a clinically important increase in occurrence rate, an unexpected outcome, or a new event that is likely to affect safety of trial volunteers. In addition to the expedited reporting above, the Investigators shall submit once a year throughout the study, or on request, a safety report to the Competent Authority and Ethics Committee.

Procedures to be Followed in the Event of Abnormal Findings

Abnormal clinical findings from medical history, examination or blood tests, will be assessed as to their clinical significance. If a test is deemed clinically significant, it may be repeated, to ensure it is not a single occurrence. If a test remains clinically significant, the volunteer will be informed and appropriate medical care arranged as appropriate and with the permission of the volunteer. Decisions to exclude the volunteer from the enrolling in the trial or to withdraw a volunteer from the trial will be at the discretion of the Investigators, following procedures for adverse events as described above ('assessment of safety').

Local Safety Monitor

A Local Safety Monitor (LSM) will be appointed to provide real-time safety oversight. The LSM will review SAEs if deemed possibly, probably or definitely related to vaccination. The LSM will be notified within 1 working day of the Investigators' being aware of their occurrence. The LSM has the power to terminate the study if deemed necessary following a vaccine-related SAE.

Safety Profile Review

The safety profile will be assessed on an ongoing basis by the Investigators and specifically after group one has been vaccinated, before enrolling volunteers into group two. An internal safety group will review safety issues and SAEs as they arise. An internal group was deemed appropriate due to extensive experience of this group with this viral vector and the expected adverse events.

Statistics

This is primarily a safety study. A secondary outcome is to determine substantial differences in the magnitude of immune responses before and after vaccination. Power calculations have been performed using Intercooled Stata 9.2. Twelve subjects are required to be able to detect a difference in means of 40%, assuming 90% power, 5% significance level and standard deviation of 30% of the mean.

Quality Control and Quality Assurance Procedures

Data will be evaluated for compliance with the protocol and accuracy in relation to source documents. The study will be conducted in accordance with procedures identified in the protocol. SOPs will be used at the clinical and laboratory site. Regular monitoring will be performed according to the requirements of the Medicines for Human Use (Clinical Trial) Regulations 2004 and ICH Good Clinical Practice (GCP). Following written standard operating procedures, the monitors will verify that the clinical trial is conducted and data are generated, documented and reported in compliance with the protocol, GCP and the applicable regulatory requirements. The Investigator site will provide direct access to all trial related source data/documents and reports for the purpose of monitoring and auditing by the sponsor, and inspection by local and regulatory authorities.

Ethics

Declaration of Helsinki

The Investigators will ensure that this study is conducted in full conformity with the current revision of the Declaration of Helsinki (last amended October 2000, with additional footnotes added 2002 and 2004).

Good Clinical Practice (GCP)

The Investigators will ensure that this study is conducted in accordance with the ethical principles that have their origin in the Declaration of Helsinki, and that are consistent with ICH GCP and the requirements of the Medicines for Human Use (Clinical Trial) Regulations 2004.

Informed Consent

Written, informed consent will be obtained, as described above.

Independent Ethics Committee (IEC)

A copy of the protocol, proposed informed consent form, other written volunteer information and the proposed advertising material will be submitted to an IEC (GTAC) for written approval. The Investigators will submit and, where necessary, obtain approval from the GTAC for all subsequent substantial amendments to the protocol and informed consent document. The Investigators will notify deviations from the protocol or SAEs occurring at the site to the sponsor and will notify the GTAC of these in accordance with local procedures.

Volunteer Confidentiality

The Investigators will ensure that the volunteer's anonymity is maintained. All documents will be stored securely and kept in strict confidence in compliance with the Data Protection Act. All computer entry and networking programs will be done with coded numbers and initials only. Only the sponsor representative, Investigators, the clinical monitor, the GTAC and the MHRA will have access to the records. Photographs taken of vaccination sites (with the volunteer's written, informed consent) will not include the volunteer's face and will be identified by the volunteer's 3-digit identification number only. Once developed, photographs will be stored as confidential records, as above. This material may be shown to other professional staff, used for educational purposes, or included in a scientific publication.

Data Handling and Record Keeping

Data Handling

The Principal Investigator will have overall responsibility for receiving, entering, cleaning, querying, analysing and storing all data that accrues from the study, but these tasks may be delegated to other Investigators. The data will be entered into the volunteers' CRFs. This includes safety data, laboratory data (both clinical and immunological) and outcome data.

Record Keeping

The Investigators will maintain appropriate medical and research records for this trial, in compliance with the requirements of the Medicines for Human Use (Clinical Trial) Regulations 2004, ICH E6 GCP and regulatory and institutional requirements for the protection of confidentiality of volunteers. The principal Investigator, co-investigators and clinical research nurses will have access to records. The Investigators will permit authorized representatives of the sponsor(s), and regulatory agencies to examine (and when required by applicable law, to copy) clinical records for the purposes of quality assurance reviews, audits and evaluation of the study safety and progress.

Source Data and Case Report Forms (CRFs)

All protocol required information will be collected in CRFs designed by the Investigators. All source documents will be filed in the CRF. Source documents are original documents, data, and records from which the volunteer's CRF data are obtained. For this study, these will include, but are not limited to, volunteer consent form, blood results, GP response letters, laboratory records, diaries, and correspondence. In the majority of cases, CRF entries will be considered source data as the CRF is the site of the original recording (i.e., there is no other written or electronic record of data). In this study this will include, but is not limited to medical history, medication records, vital signs, physical examination records, urine assessments, blood results, adverse event data and details of vaccinations. All source data and volunteer CRFs will be stored securely.

Results

Figure 9:
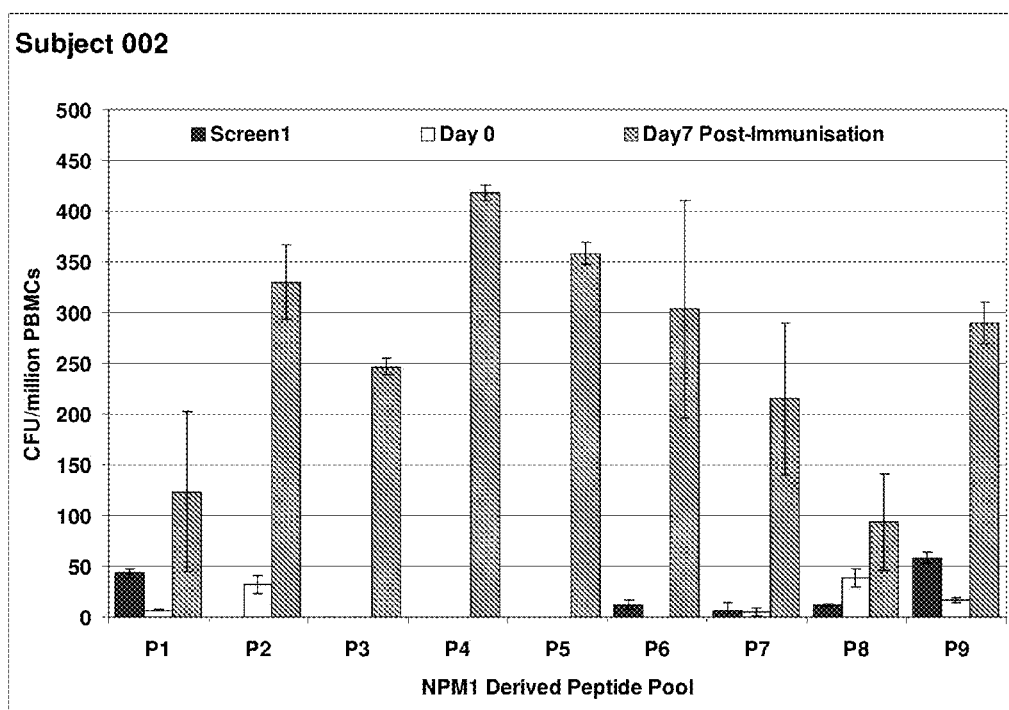

FIG. 9 shows IFN-γ secretion per million PBMCs for Subject 002 prior to and post-immunisation. The bars show IFN-γ secretion in response to 5 μg/ml peptides pools P1-P8 which comprises 10 peptides per pool spanning the influenza fusion protein NP+M1. P9 is a single pool comprising all 80 peptides from NPM1 fusion protein. Black bars represent baseline responses prior to immunisation. Clear bars represent day of immunisation responses. Hatched bars represent day 7 post-immunisation responses. The error bars show standard error of mean per triplicate stimulation with each peptide pool. The background (media only) has been subtracted from each response. Background was as follows; screening, 10 spots per million PBMCs, Day 0, 23 spots per million PBMCs; Day 7 post-immunisation, 12 spots per million PBMCs.

The peptides used in the analysis are shown in the table below:

| Pool | Peptide Constitution | |
|---|---|---|
| P1 | MASQGTKRSYEQMETDGDR | (SEQ ID NO: 7) |
| | YEQMETDGDRQNATEIRASV | (SEQ ID NO: 8) |
| | RQNATEIRASVGKMIDGIGR | (SEQ ID NO: 9) |
| | VGKMIDGIGRFYIQMCTELK | (SEQ ID NO: 10) |
| | FYIQMCTELKLSDYEGRLI | (SEQ ID NO: 11) |
| | KLSDYEGRLIQNSLTIEKMV | (SEQ ID NO: 12) |
| | IQNSLTIEKMVLSAFDERR | (SEQ ID NO: 13) |
| | MVLSAFDERRNRYLEEHPSA | (SEQ ID NO: 14) |
| | NRYLEEHPSAGKDPKKTGG | (SEQ ID NO: 15) |
| | AGKDPKKTGGPIYRRVDGKW | (SEQ ID NO: 16) |
| P2 | PIYRRVDGKWMRELVLYDK | (SEQ ID NO: 17) |
| | WMRELVLYDKEEIRRIWRQA | (SEQ ID NO: 18) |
| | EEIRRIWRQANNGEDATAGL | (SEQ ID NO: 19) |
| | NNGEDATAGLTHMMIWHSNL | (SEQ ID NO: 20) |
| | THMMIWHSNLNDTTYQRTRA | (SEQ ID NO: 21) |
| | NDTTYQRTRALVRTGMDPRM | (SEQ ID NO: 22) |
| | LVRTGMDPRMCSLMQGSTL | (SEQ ID NO: 23) |
| | MCSLMQGSTLPRRSGAAGAA | (SEQ ID NO: 24) |
| | PRRSGAAGAAVKGIGTMVM | (SEQ ID NO: 25) |
| | AVKGIGTMVMELIRMVKRGI | (SEQ ID NO: 26) |
| P3 | ELIRMVKRGINDRNFWRG | (SEQ ID NO: 27) |
| | GINDRNFWRGENGRKTRSAY | (SEQ ID NO: 28) |
| | ENGRKTRSAYERMCNILKGK | (SEQ ID NO: 29) |
| | ERMCNILKGKFQTAAQRAMV | (SEQ ID NO: 30) |
| | FQTAAQRAMVDQVRESRNPG | (SEQ ID NO: 31) |
| | DQVRESRNPGNAEIEDLIFL | (SEQ ID NO: 32) |
| | NAEIEDLIFLARSALILRG | (SEQ ID NO: 33) |
| | LARSALILRGSVAHKSCLPA | (SEQ ID NO: 34) |
| | SVAHKSCLPACVYGPAVSSG | (SEQ ID NO: 35) |
| | CVYGPAVSSGYDFEKEGYSL | (SEQ ID NO: 36) |
| P4 | YDFEKEGYSLVGIDPFKLL | (SEQ ID NO: 37) |
| | LVGIDPFKLLQNSQVYSLIR | (SEQ ID NO: 38) |
| | LQNSQVYSLIRPNENPAHK | (SEQ ID NO: 39) |
| | IRPNENPAHKSQLVWMACH | (SEQ ID NO: 40) |
| | KSQLVWMACHSAAFEDLRLL | (SEQ ID NO: 41) |
| | SAAFEDLRLLSFIRGTKV | (SEQ ID NO: 42) |
| | LLSFIRGTKVSPRGKLSTRG | (SEQ ID NO: 43) |
| | SPRGKLSTRGVQIASNENM | (SEQ ID NO: 44) |
| | GVQIASNENMDNMGSSTLEL | (SEQ ID NO: 45) |
| | DNMGSSTLELRSGYWAIRTR | (SEQ ID NO: 46) |
| P5 | RSGYWAIRTRSGGNTNQQRA | (SEQ ID NO: 47) |
| | SGGNTNQQRASAGQISV | (SEQ ID NO: 48) |
| | NQQRASAGQISVQPTFSVQR | (SEQ ID NO: 49) |
| | SVQPTFSVQRNLPFEKSTVM | (SEQ ID NO: 50) |
| | NLPFEKSTVMAAFTGNTEGR | (SEQ ID NO: 51) |
| | AAFTGNTEGRTSDMRAEIIR | (SEQ ID NO: 52) |
| | TSDMRAEIIRMMEGAKPEEV | (SEQ ID NO: 53) |
| | MMEGAKPEEVSFRGRGVFEL | (SEQ ID NO: 54) |
| | SFRGRGVFELSDEKATNPIV | (SEQ ID NO: 55) |
| | SDEKATNPIVPSFEMSNEG | (SEQ ID NO: 56) |
| P6 | VPSFEMSNEGSYFFGDNA | (SEQ ID NO: 57) |
| | EGSYFFGDNAEEYDNgggpg | (SEQ ID NO: 58) |
| | EEYDNgggpgggMSLLTEV | (SEQ ID NO: 59) |
| | gggMSLLTEVETYVLSIV | (SEQ ID NO: 60) |
| | EVETYVLSIVPSGPLKAEIA | (SEQ ID NO: 61) |
| | PSGPLKAEIAQRLEDVFAGK | (SEQ ID NO: 62) |
| | AQRLEDVFAGKNTDLEALM | (SEQ ID NO: 63) |
| | GKNTDLEALMEWLKTRPIL | (SEQ ID NO: 64) |
| | MEWLKTRPILSPLTKGILGF | (SEQ ID NO: 65) |
| | SPLTKGILGFVFTLTVPSER | (SEQ ID NO: 66) |

-continued

| Pool | Peptide Constitution | |
|---|---|---|
| P7 | VFTLTVPSERGLQRRRFV | (SEQ ID NO: 67) |
| | ERGLQRRRFVQNALNGNG | (SEQ ID NO: 68) |
| | FVQNALNGNGDPNNMDKAVK | (SEQ ID NO: 69) |
| | DPNNMDKAVKLYRKLKREI | (SEQ ID NO: 70) |
| | KLYRKLKREITFHGAKEIAL | (SEQ ID NO: 71) |
| | TFHGAKEIALSYSAGALA | (SEQ ID NO: 72) |
| | ALSYSAGALASCMGLIYNRM | (SEQ ID NO: 74) |
| | SCMGLIYNRMGAVTTEVAFG | (SEQ ID NO: 75) |
| | GAVTTEVAFGLVCATCEQIA | (SEQ ID NO: 76) |
| | LVCATCEQIADSQHRSHRQM | (SEQ ID NO: 77) |
| P8 | DSQHRSHRQMVATTNPLIKH | (SEQ ID NO: 78) |
| | VATTNPLIKHENRMVLA | (SEQ ID NO: 79) |
| | IKHENRMVLASTTAKAMEQM | (SEQ ID NO: 80) |
| | STTAKAMEQMAGSSEQAAEA | (SEQ ID NO: 81) |
| | AGSSEQAAEAMEIASQARQM | (SEQ ID NO: 82) |
| | MEIASQARQMVQAMRTVGTH | (SEQ ID NO: 83) |
| | VQAMRTVGTHPSSSTGLR | (SEQ ID NO: 84) |
| | THPSSSTGLRDDLLENLQTY | (SEQ ID NO: 85) |
| | DDLLENLQTYQKRMGVQMQR | (SEQ ID NO: 86) |
| | QKRMGVQMQRFK | (SEQ ID NO: 87) |
| P9 | All Above Peptides | |

Figure 10:
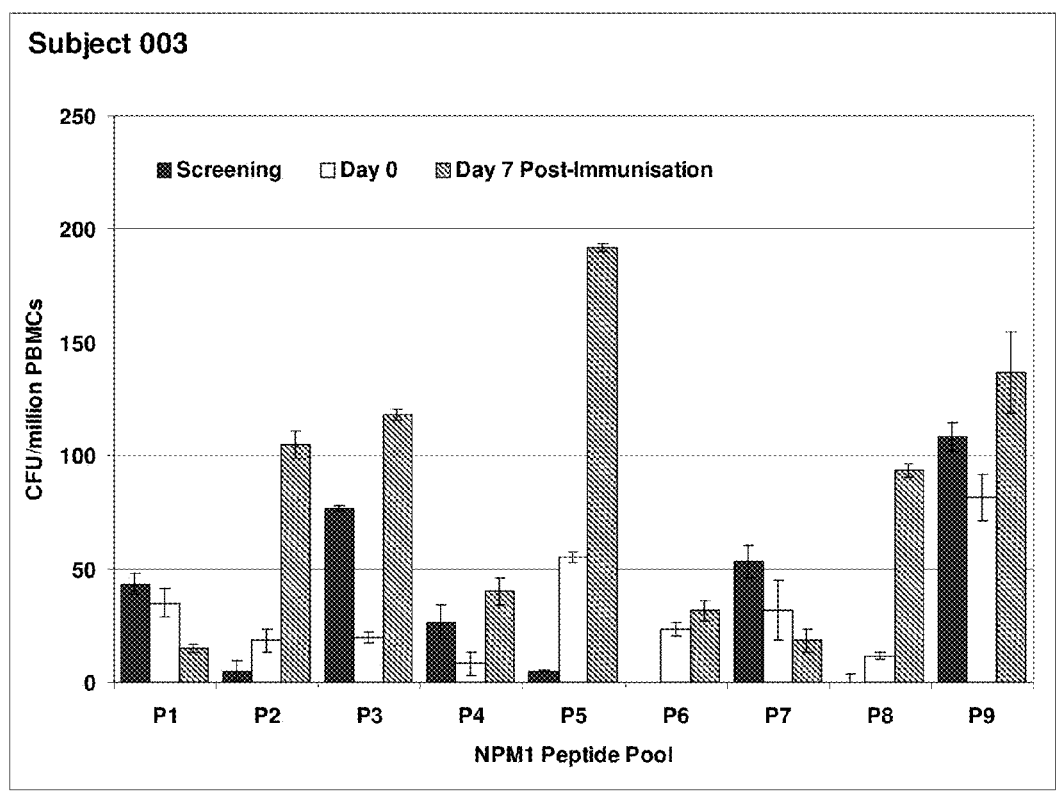

FIG. 10 shows IFN-γ secretion per million PBMCs for Subject 003 prior to and following immunisation. The bars show IFN-γ secretion in response to 5 μg/ml peptides pools P1-P8 which comprises 10 peptides per pool spanning the influenza fusion protein NP+M1. P9 is a single pool comprising all 80 peptides from NPM1 fusion protein. Black bars represent baseline responses prior to immunisation. Clear bars represent day of immunisation responses. Hatched bars represent day 7 post-immunisation responses. error bars showing the standard deviation per triplicate stimulation with each peptide pool will be added. The background (media only) has been subtracted from each response. Background was as follows; screening, 13 spots per million PBMCs, Day 0, 7 spots per million PBMCs; Day 7 post-immunisation, 2 spots per million PBMCs.

Figure 11:
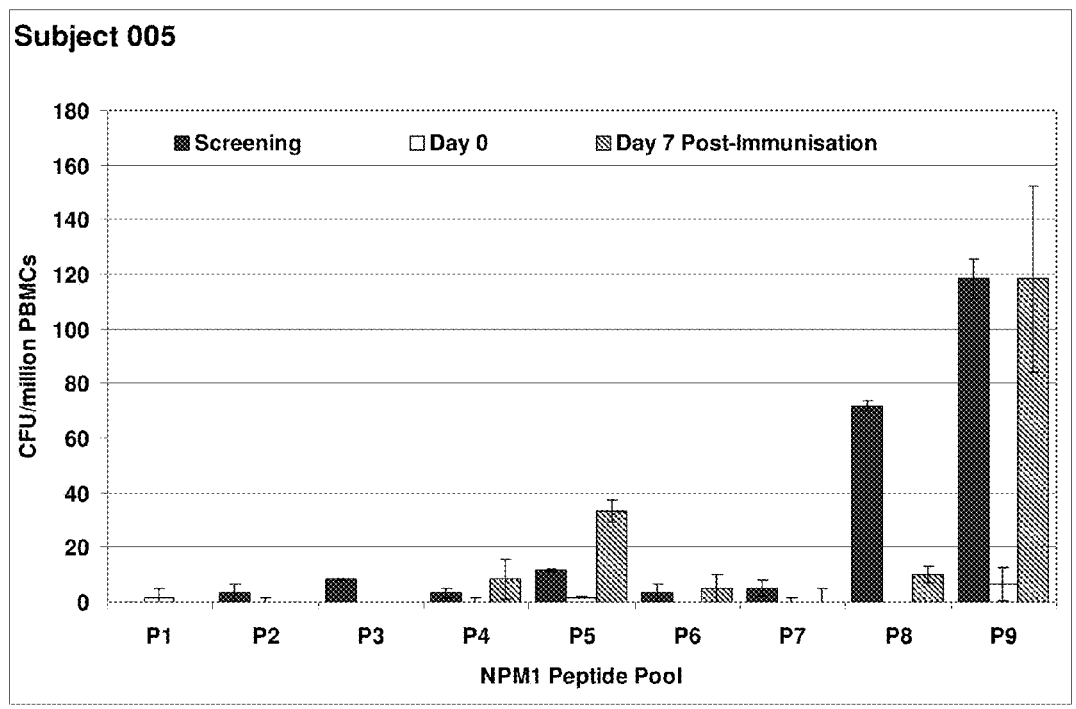

FIG. 11 shows IFN-γ secretion per million PBMCs for Subject 005 prior to and following immunisation. The bars show IFN-γ secretion in response to 5 μg/ml peptides pools P1-P8 which comprises 10 peptides per pool spanning the influenza fusion protein NP+M1. P9 is a single pool comprising all 80 peptides from NPM1 fusion protein. Black bars represent baseline responses prior to immunisation. Clear bars represent day of immunisation responses. Hatched bars represent day 7 post-immunisation responses. The error bars showing the standard deviation per triplicate stimulation with each peptide pool will be added. The background (media only) has been subtracted from each response. Background was as follows; screening, 0 spots per million PBMCs, Day 0, 5 spots per million PBMCs (irrelevant peptide control); Day 7 post-immunisation, 3 spots per million PBMCs.

Figure 12:
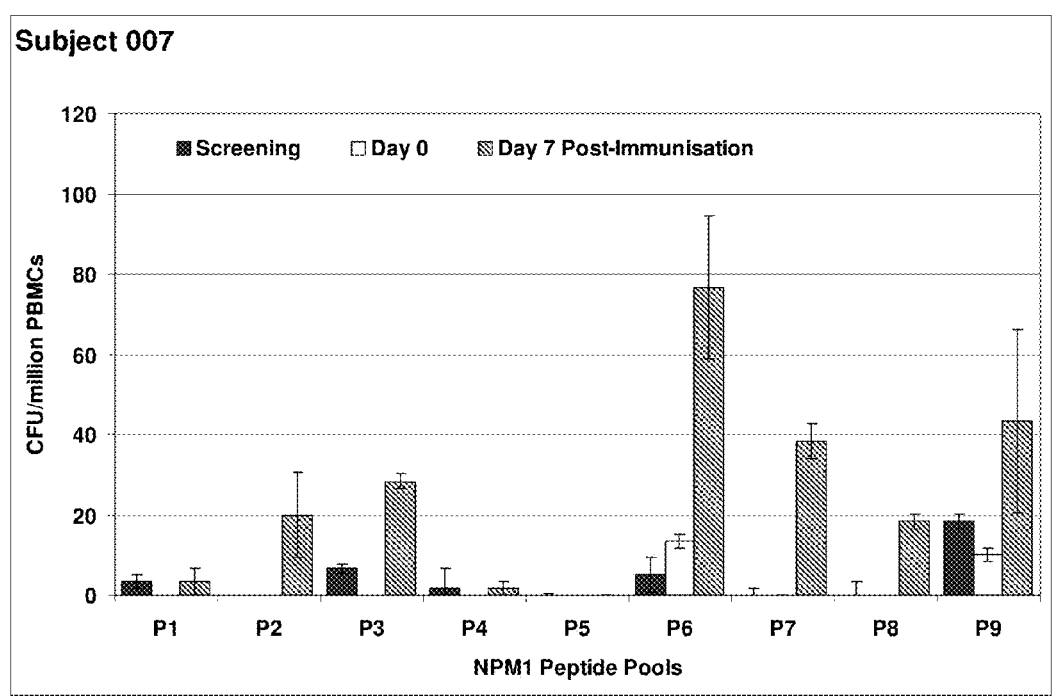

FIG. 12 shows IFN-γ secretion per million PBMCs for Subject 007 prior to and following immunisation. The bars show IFN-γ secretion in response to 5 μg/ml peptides pools P1-P8 which comprises 10 peptides per pool spanning the influenza fusion protein NP+M1. P9 is a single pool comprising all 80 peptides from NPM1 fusion protein. Black bars represent baseline responses prior to immunisation. Clear bars represent day of immunisation responses. Hatched bars represent day 7 post-immunisation responses. The error bars showing the standard deviation per triplicate stimulation with each peptide pool will be added. The background (media only) has been subtracted from each response. Background at screening was 3 spots per million PBMCs, Day 0, 13 spots per million PBMCs; Day 7 post-immunisation, 0 spots per million PBMCs.

Figure 13:
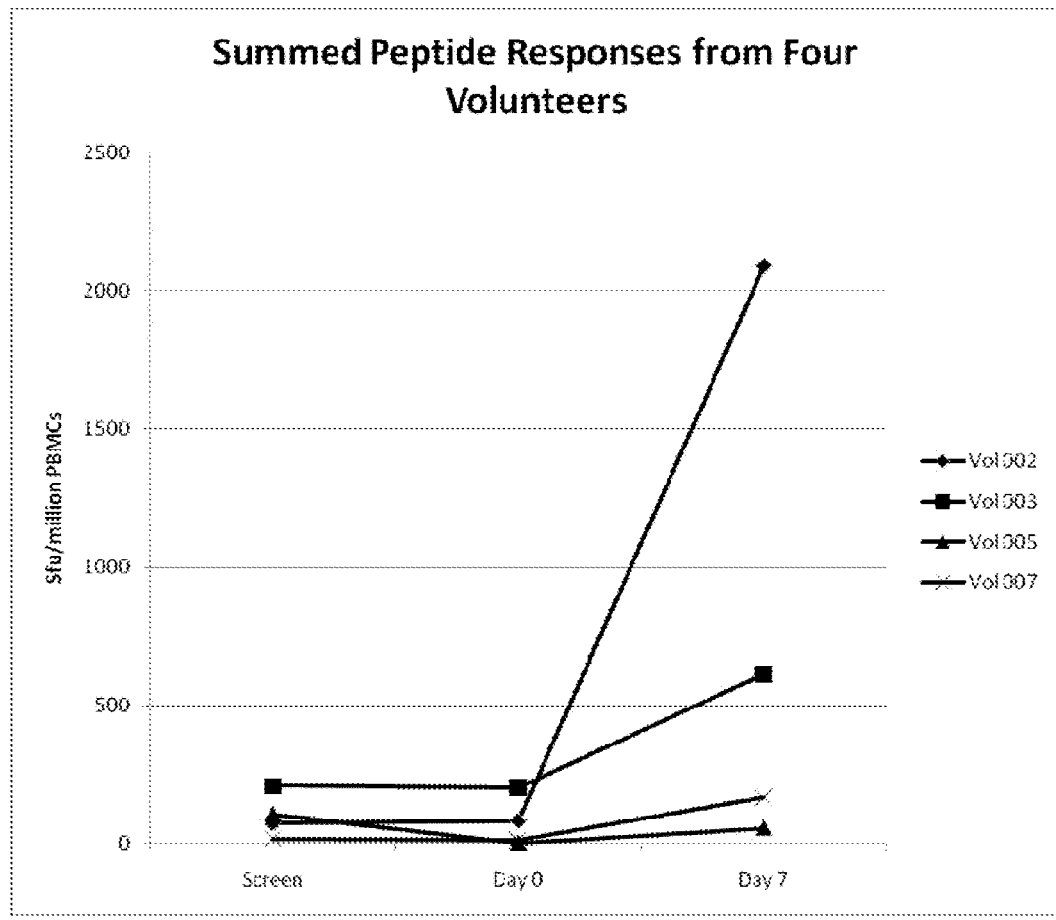
Figure 14A:
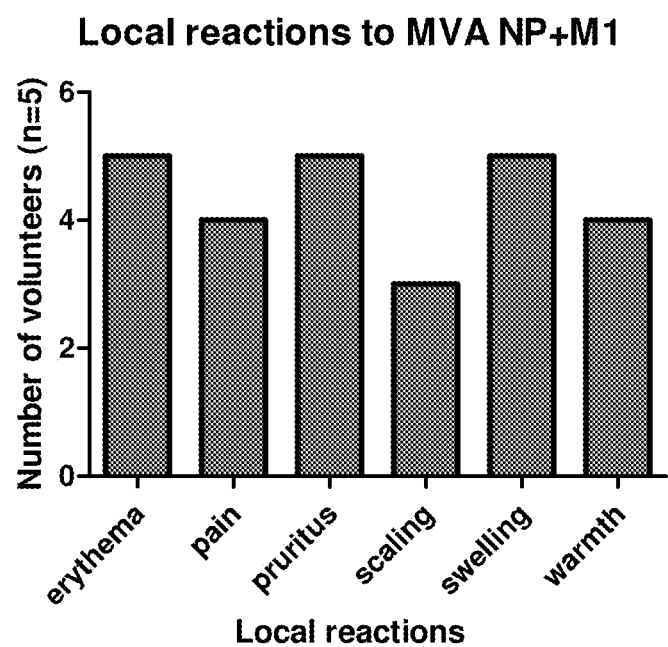
Figure 14B:
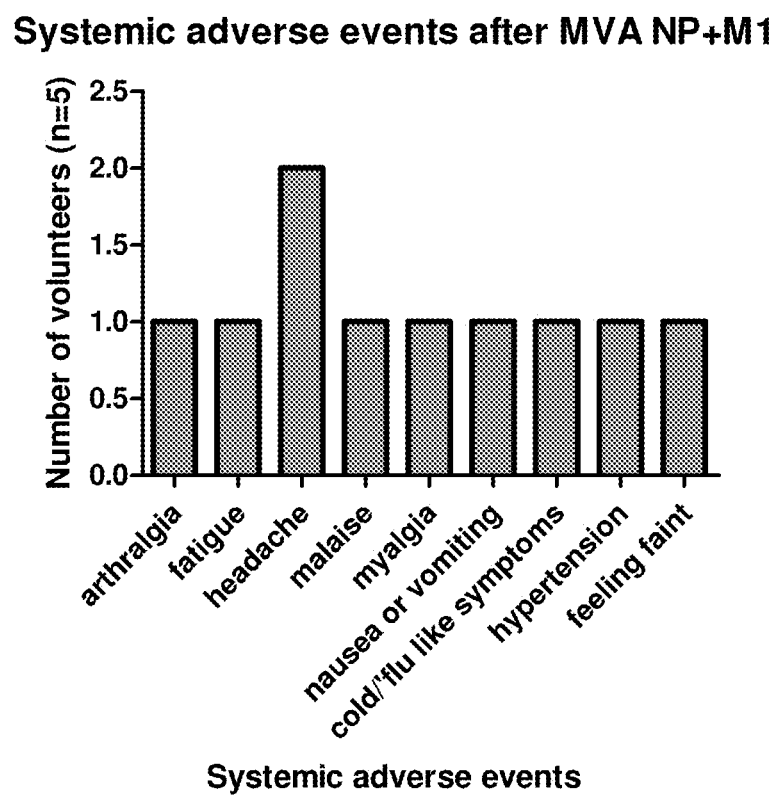
Figure 15A:
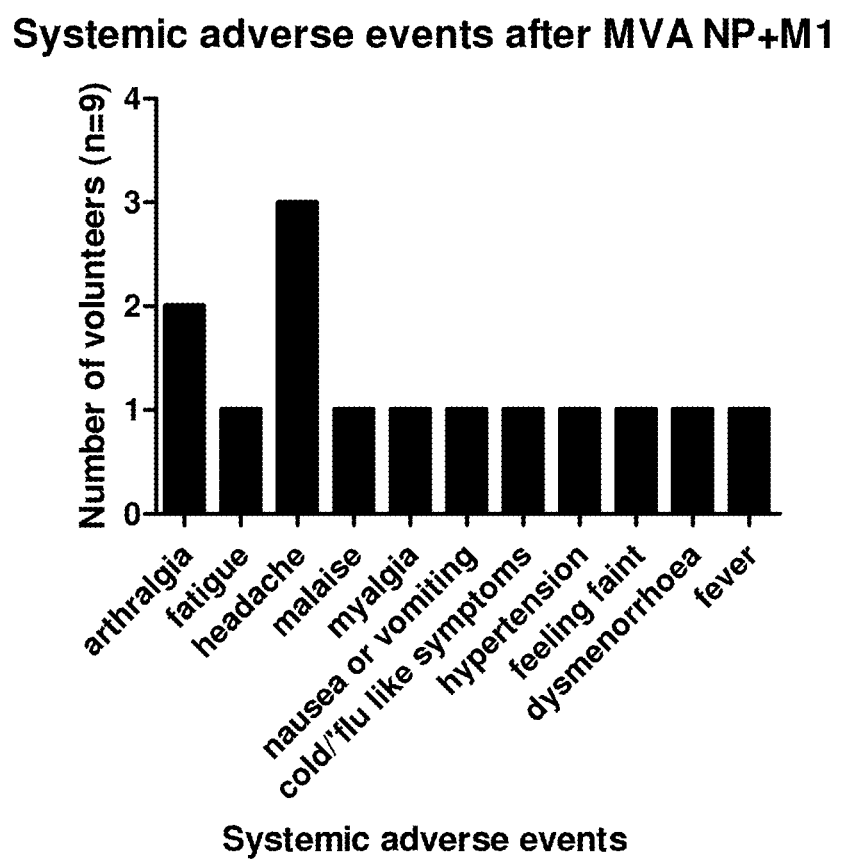
Figure 15B:
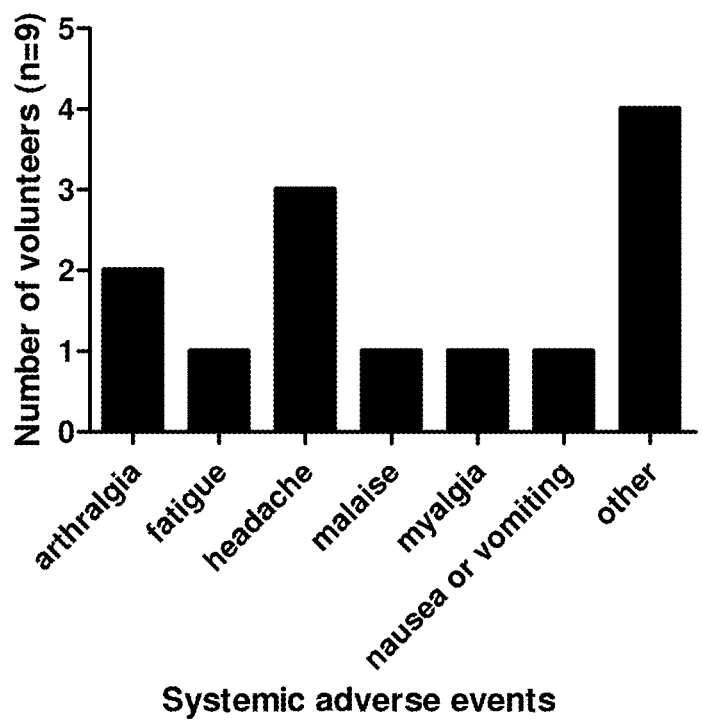
Figure 15C:
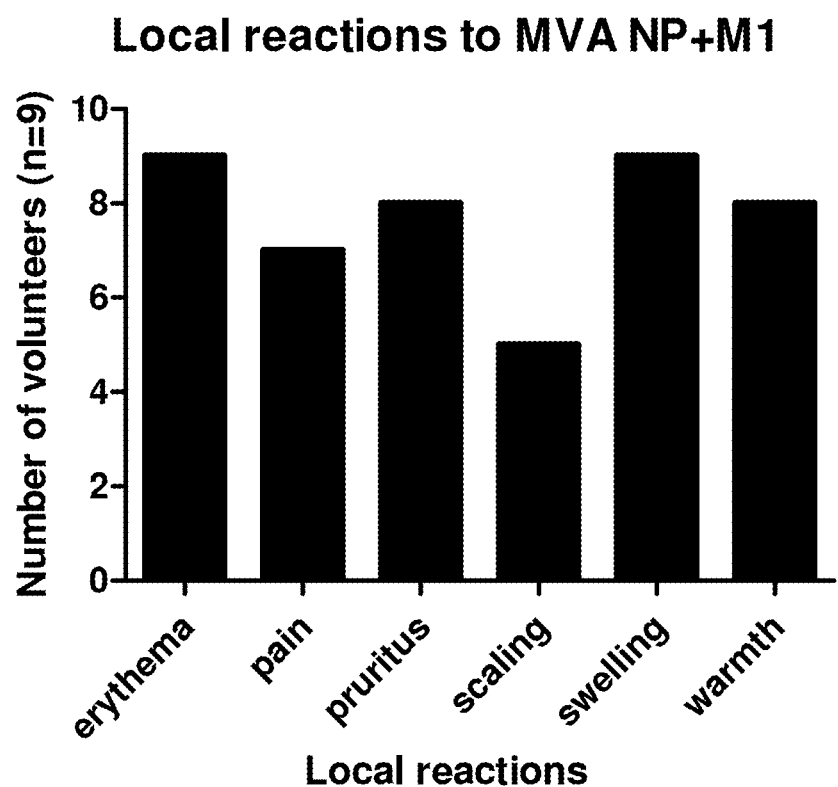
Figure 15D:
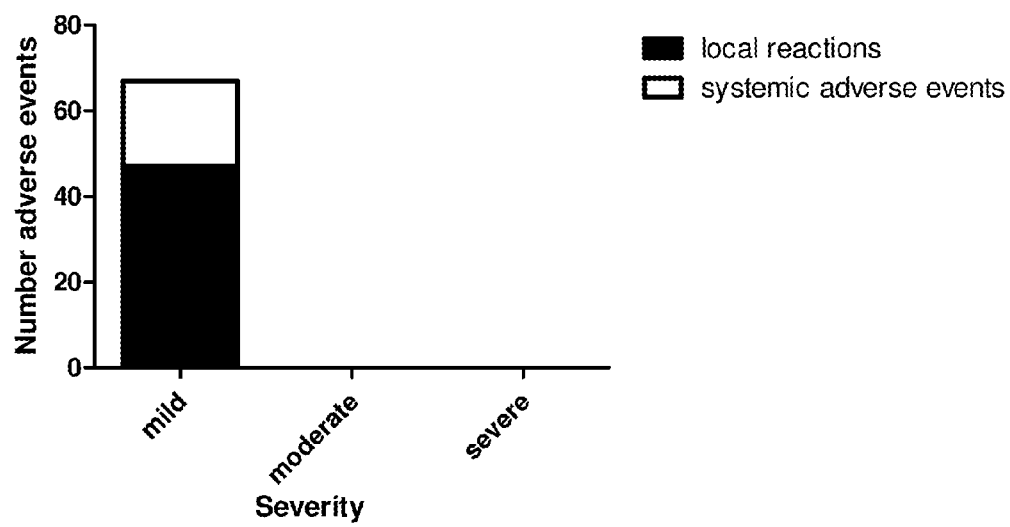
Figure 16:
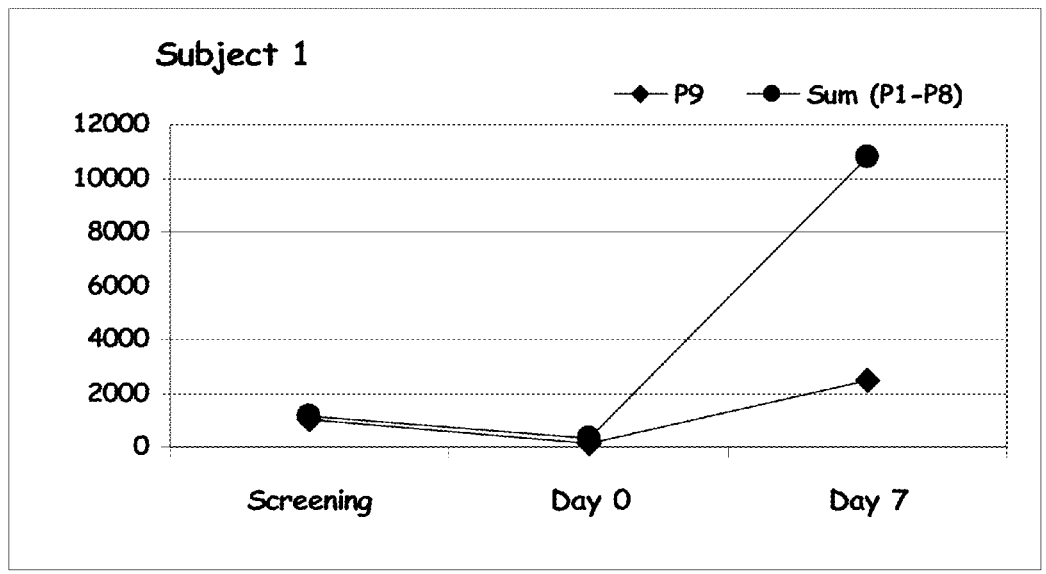
Figure 17:
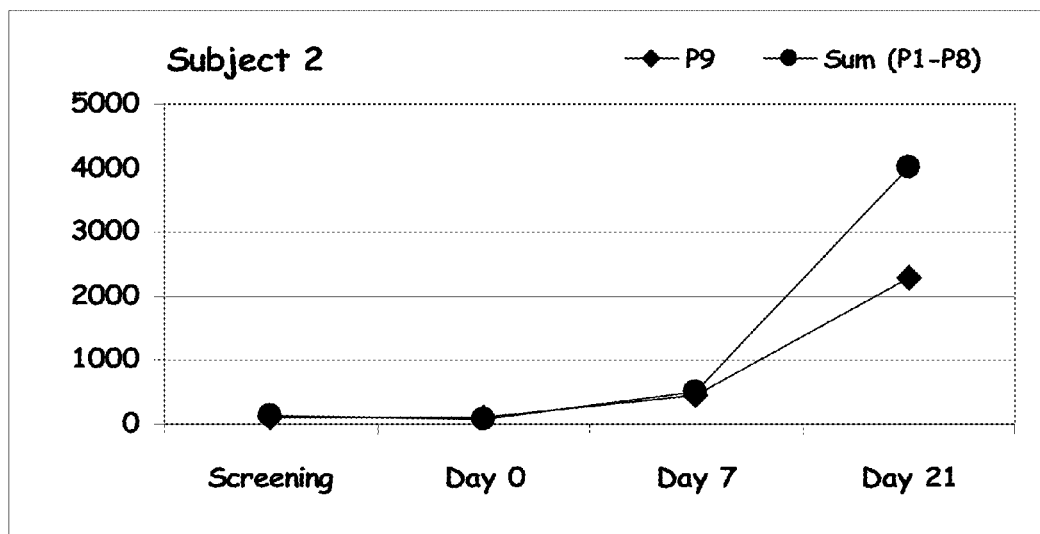
Figure 18:
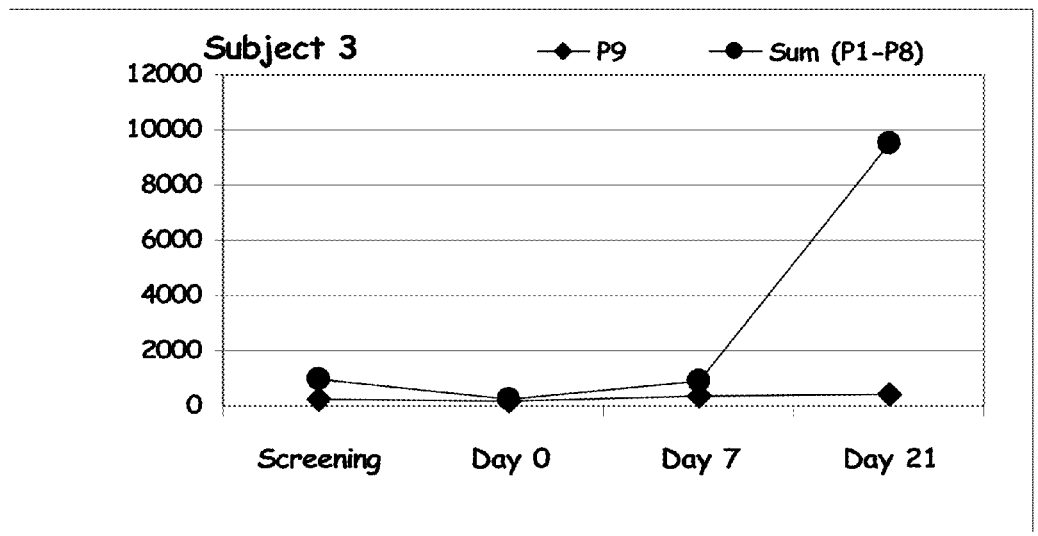
Figure 19:
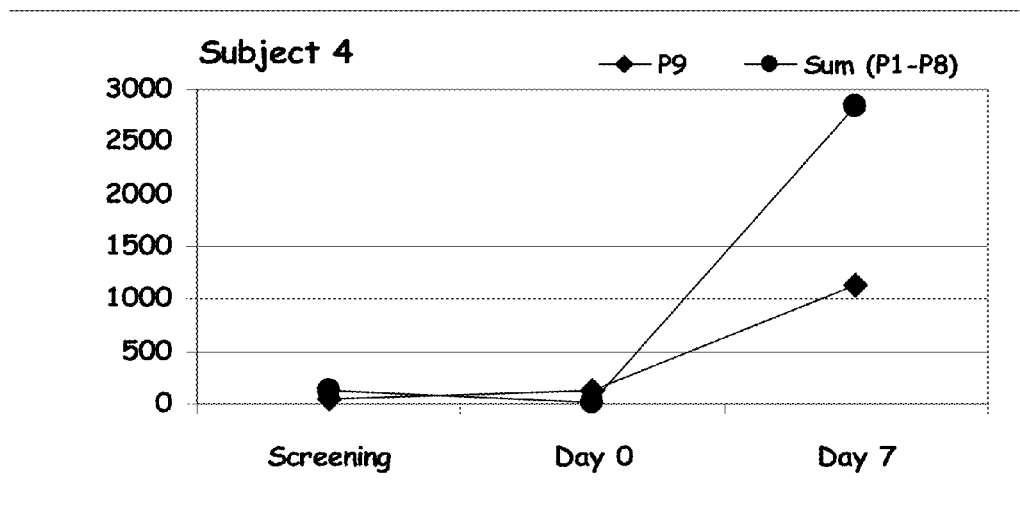
Figure 20:
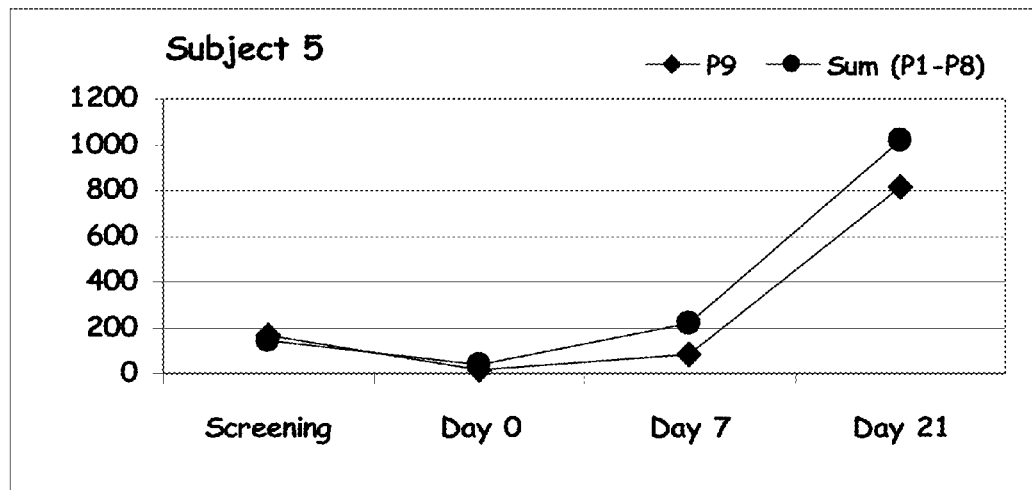
Figure 21:
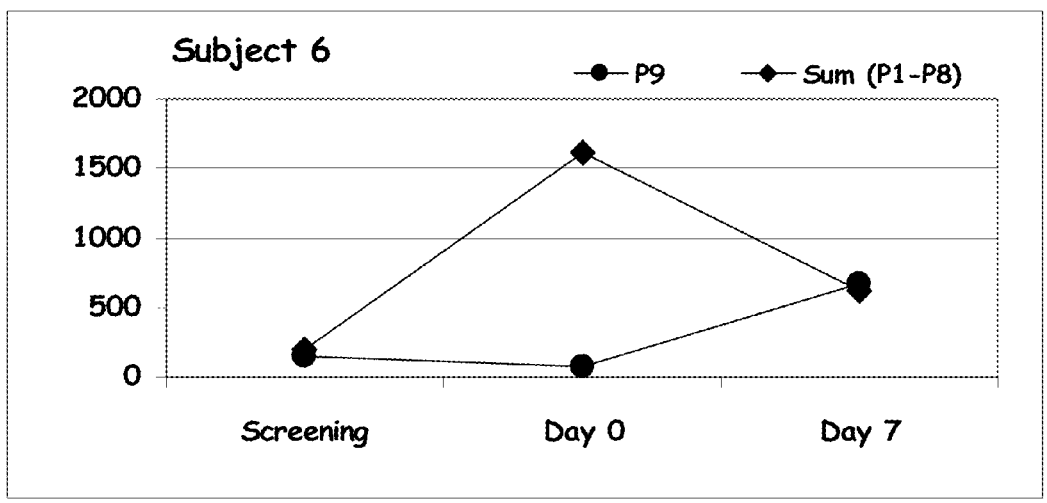
Figure 22:
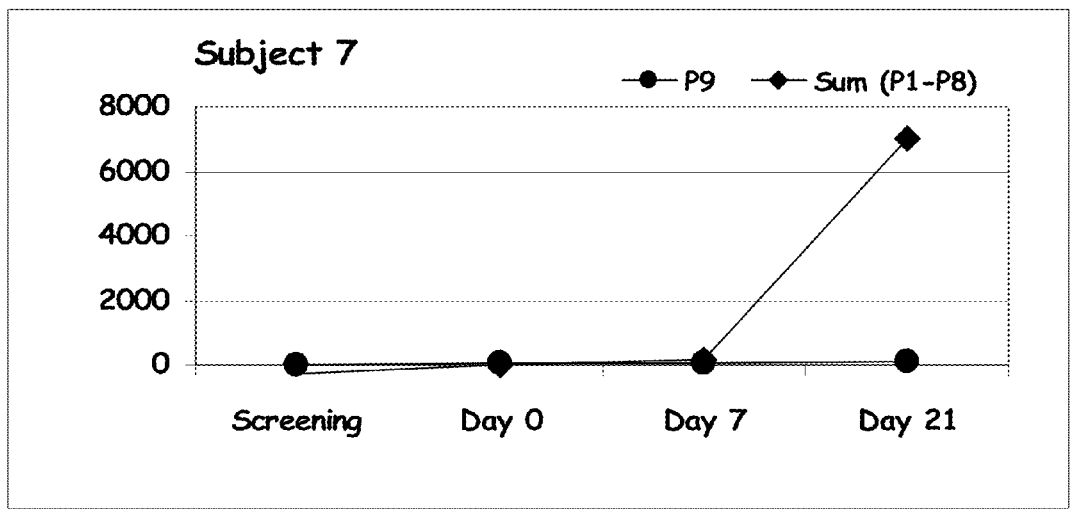
Figure 23:
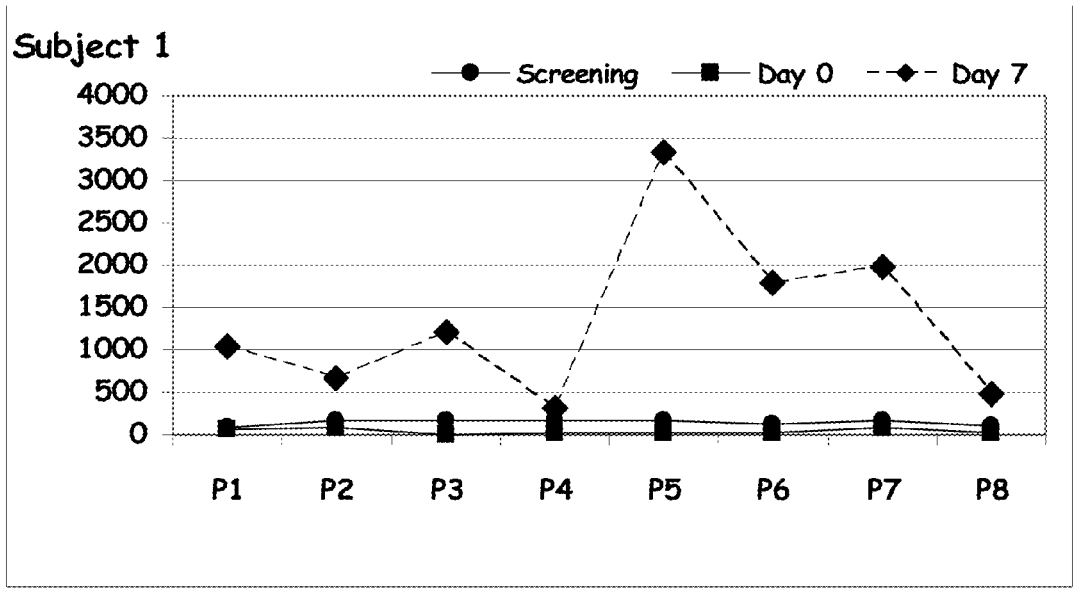
Figure 24:
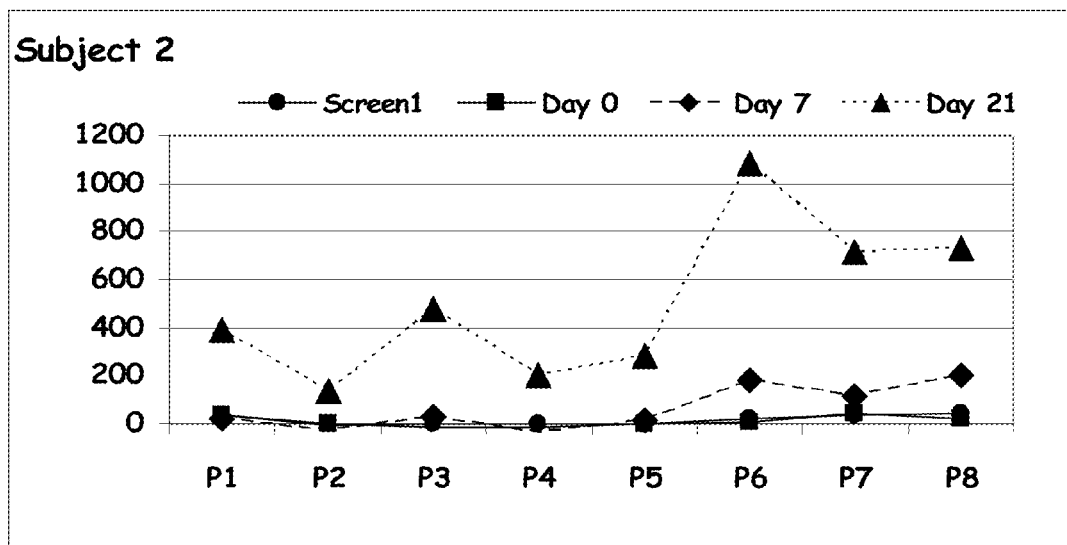
Figure 25:
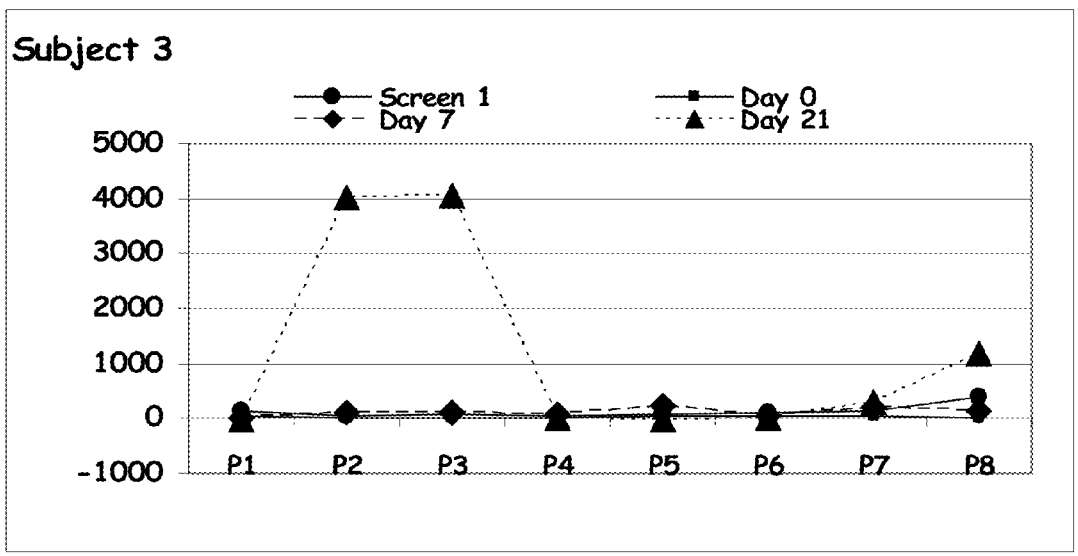
Figure 26:
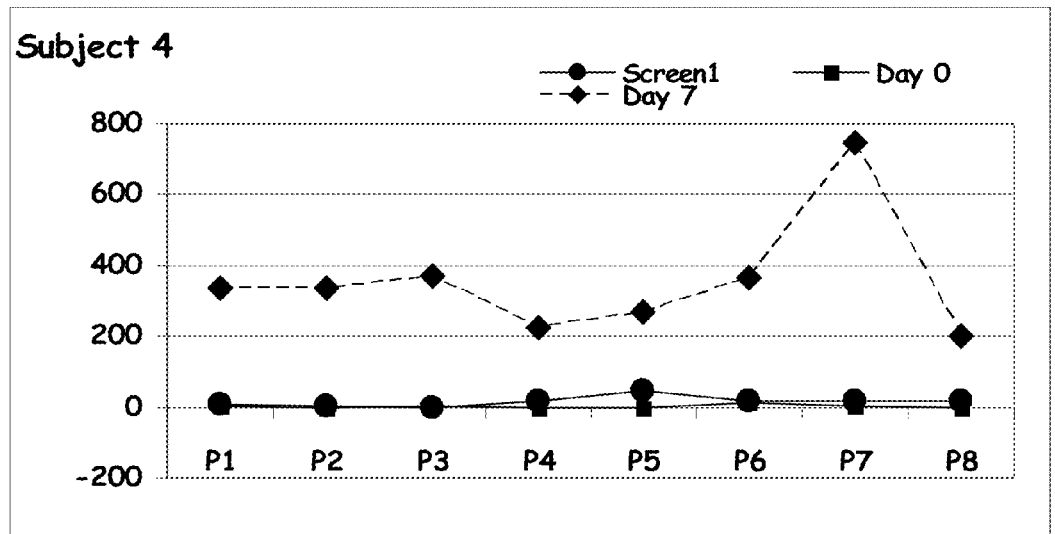
Figure 27:
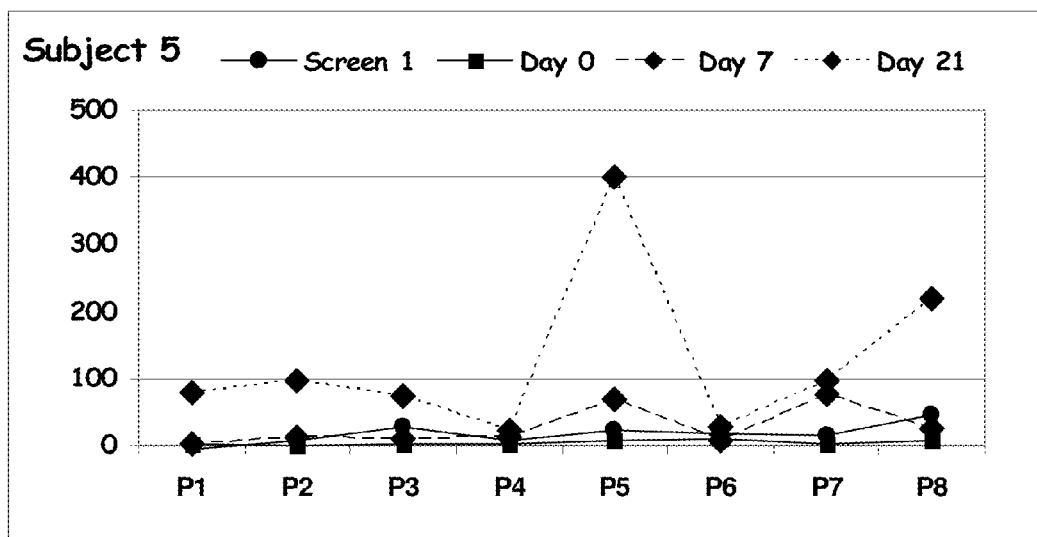
Figure 28:
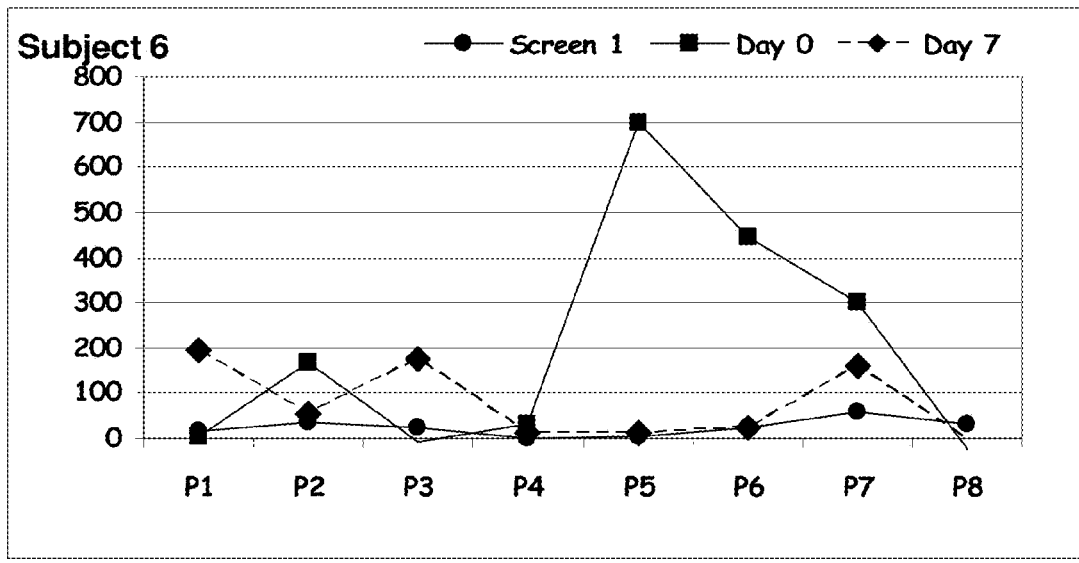
Figure 29:
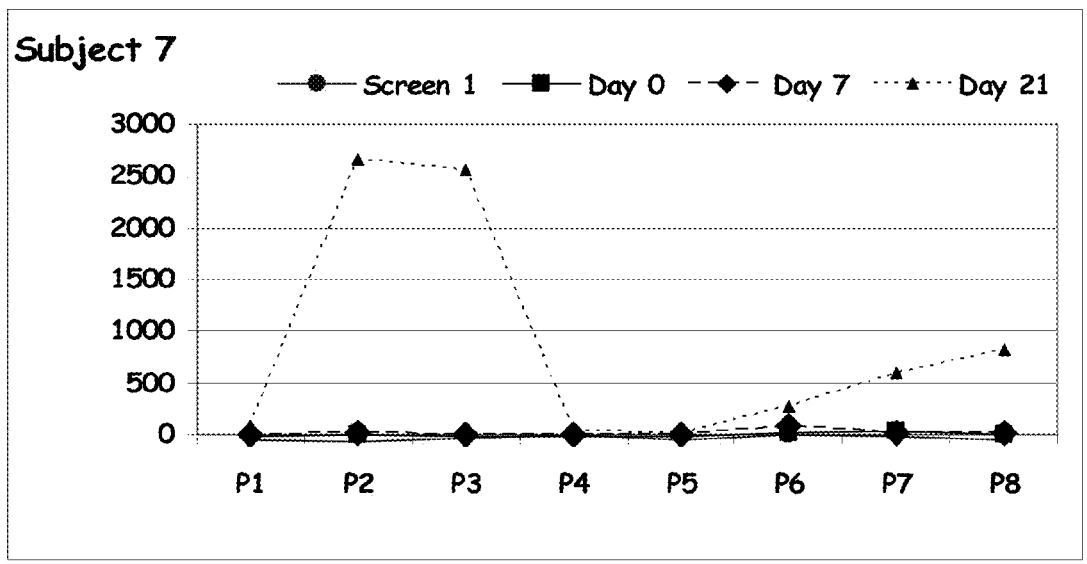

FIG. 13 shows IFN-γ secretion per million PBMCs for four volunteers prior to and following immunisation. The sum of the responses to peptide pools 1 to 8 (after background subtraction) is shown for three timepoints.

Safety Data

FIG. 14 shows local and systemic adverse events after vaccination with MVA-NP+M1, including data from five volunteers. All events were graded as mild.

Safety Data:

| LOCAL AE | Number OF AE | SYSTEMIC ae | Number OF AE | LOCAL AE | Number of people | SYSTEMIC ae | Number of people |
|---|---|---|---|---|---|---|---|
| erythema | 9 | arthralgia | 2 | erythema | 9 | arthralgia | 2 |
| pain | 7 | abnormal biochemistry | 0 | pain | 7 | abnormal biochemistry | 0 |
| pruritus | 8 | abnormal haematology | 0 | pruritus | 8 | abnormal haematology | 0 |
| scaling | 5 | documented fever | 0 | scaling | 5 | documented fever | 0 |
| swelling | 9 | fatigue | 1 | swelling | 9 | fatigue | 1 |
| warmth | 9 | feverish | 2 | warmth | 8 | feverish | 1 |
| TOTAL | 47 | headache | 6 | TOTAL | 46 | headache | 3 |
| | | lymphadenopathy | 0 | | | lymphadenopathy | 0 |
| | | malaise | 2 | | | malaise | 1 |
| | | myalgia | 1 | | | myalgia | 1 |
| | | nausea or vomiting | 1 | | | nausea or vomiting | 1 |
| | | other | 5 | | | other | 4 |
| | | TOTAL | 20 | | | TOTAL | 14 |

FIG. 15 (parts A-D) summarises the safety data. These show adverse events after intradermal vaccination with MVA-NP+M1, from nine volunteers. Both local and systemic adverse events are as expected after immunisation with an MVA vaccine administered intradermally. The severity of all adverse events was graded as mild.

Time Course of Total Responses to the NP+M1 Insert, Measured by IFN-g ELISpot Assay.

The responses from all available individual subjects over various time courses of treatment are presented. In particular, reference is made to FIGS. 16 to 22. In these figures, the y axis represents the number of spot-forming cells per million peripheral blood mononuclear cells (PBMCs). The x axis shows the time at which blood was taken. The interval between screening and day of vaccination (Day 0) was three to five weeks. The diamonds represent the sum of the responses to peptide pools 1 to 8. The circles represent the response to pool 9 which contains all 80 peptides.

Breadth of the Response to the NP+M1 Insert.

The responses from all available individual subjects over various time courses of treatment are presented. The y axis represents the number of spot-forming cells per million peripheral blood mononuclear cells (PBMCs). The x axis shows the response to each of the peptide pools (see table above for peptide details). The interval between screening and day of vaccination (Day 0) was three to five weeks.

The immune responses to the MVA-NP+M1 vaccine are surprisingly strong, being an order of magnitude higher to that seen when MVA expressing malaria antigens is employed as the boosting agent in a heterologous prime boost regime, and despite the fact that the dose of MVA used here is four-fold lower than that used in malaria vaccine trials. A further unexpected finding is that the peak of the immune response is not at day 7 as has been seen in malaria, TB and HIV vaccine trials of MVA-vectored vaccines, but continues to increase to day 21.

Some of the participants in the study had strong effector T cell responses to NP and M1 prior to vaccination (particularly subject 1). It would be predicted that these T cells would recognize and destroy antigen presenting cells expressing NP and M1 after vaccination, and that as a result of this no boosting of the immune response would occur. Boosting would be predicted in individuals with a low level effector T cell response prior to vaccination. However boosting does in fact occur in all participants. Also of note is the breadth of the immune response, which is more likely to provide cross-subtype immunity than a strong response to a single region of the vaccine antigen.

Thus, in summary, there is statistically significant boosting of T cell responses after vaccination according to the present invention in the first seven human volunteer subjects whose data is discussed above. A paired analysis ANOVA (non-parametric) on the data from these seven volunteers indicates no statistically significant difference between the Screen and Day 0 samples, but a difference between day 0 and day 7 samples ($P<0.05$).

REFERENCES

1. Molinari, N. A., et al., *The annual impact of seasonal influenza in the US: measuring disease burden and costs.* Vaccine, 2007. 25(27): p. 5086-96.
2. Babakir-Mina, M., et al., *Influenza virus A (H5N1): a pandemic risk?* New Microbiol, 2007. 30(2): p. 65-78.
3. Bardenheier, B. H., et al., *Influenza vaccine supply, 2005-2006: did we come up short?* BMC Health Serv Res, 2007. 7: p. 66.
4. Bresson, J. L., et al., *Safety and immunogenicity of an inactivated split-virion influenza A/Vietnam/1194/2004 (H5N1) vaccine: phase I randomised trial.* Lancet, 2006. 367(9523): p. 1657-64.
5. Treanor, J. J., et al., *Safety and immunogenicity of an inactivated subvirion influenza A (H5N1) vaccine.* N Engl J Med, 2006. 354(13): p. 1343-51.
6. Stephenson, I., et al., *Cross-reactivity to highly pathogenic avian influenza H5N1 viruses after vaccination with nonadjuvanted and MF59-adjuvanted influenza A/Duck/Singapore/97 (H5N3) vaccine: a potential priming strategy.* J Infect Dis, 2005. 191(8): p. 1210-5.
7. Le, Q. M., et al., *Avian flu: isolation of drug-resistant H5N1 virus.* Nature, 2005. 437(7062): p. 1108.
8. McMichael, A. J., et al., *Cytotoxic T-cell immunity to influenza.* N Engl J Med, 1983. 309(1): p. 13-7.
9. Ulmer, J. B., et al., *Heterologous protection against influenza by injection of DNA encoding a viral protein.* Science, 1993. 259(5102): p. 1745-9.
10. Epstein, S. L., et al., *Protection against multiple influenza A subtypes by vaccination with highly conserved nucleoprotein.* Vaccine, 2005.
11. McShane, H., et al., *Recombinant modified vaccinia virus Ankara expressing antigen 85A boosts BCG-primed and naturally acquired antimycobacterial immunity in humans.* Nat Med, 2004. 10(11): p. 1240-4.
12. McConkey, S. J., et al., *Enhanced T-cell immunogenicity of plasmid DNA vaccines boosted by recombinant modified vaccinia virus Ankara in humans.* Nat Med, 2003. 9(6): p. 729-35.
13. Webster, D. P., et al., *Enhanced T cell-mediated protection against malaria in human challenges by using the recombinant poxviruses FP9 and modified vaccinia virus Ankara.* Proc Natl Acad Sci USA, 2005. 102(13): p. 4836-41.
14. Blanchard, T. J., et al., *Modified vaccinia virus Ankara undergoes limited replication in human cells and lacks several immunomodulatory proteins: implications for use as a human vaccine.* J. Gen. Virol., 1998. 79(Pt 5): p. 1159-67.
15. Mayr, A., et al., *The smallpox vaccination strain MVA: marker, genetic structure, experience gained with the parenteral vaccination and behavior in organisms with a debilitated defence mechanism.* Zentralbl. Bakteriol. [B], 1978. 167(5-6): p. 375-90.
16. Sutter, G. and B. Moss, *Nonreplicating vaccinia vector efficiently expresses recombinant genes.* Proc. Natl. Acad. Sci., 1992. 89(22): p. 10847-51.
17. Cosma, A., et al., *Therapeutic vaccination with MVA-HIV-1 nef elicits Nef-specific T-helper cell responses in chronically HIV-1 infected individuals.* Vaccine, 2003. 22(1): p. 21-9.
18. Dorrell, L., et al., *Safety and tolerability of recombinant modified vaccinia virus Ankara expressing an HIV-1 gag/multiepitope immunogen (MVA.HIVA) in HIV-1-infected persons receiving combination antiretroviral therapy.* Vaccine, 2007. 25(17): p. 3277-83.
19. Goonetilleke, N., et al., *Induction of multifunctional human immunodeficiency virus type 1 (HIV-1)-specific T cells capable of proliferation in healthy subjects by using a prime-boost regimen of DNA-and modified vaccinia virus Ankara-vectored vaccines expressing HIV-1 Gag coupled to CD8+ T-cell epitopes.* J Virol, 2006. 80(10): p. 4717-28.
20. Bejon, P., et al., *Safety profile of the viral vectors of attenuated fowlpox strain FP9 and modified vaccinia virus Ankara recombinant for either of 2 preerythrocytic malaria antigens, ME-TRAP or the circumsporozoite protein, in children and adults in Kenya.* Clin Infect Dis, 2006. 42(8): p. 1102-10.
21. Meyer, R. G., et al., *A phase I vaccination study with tyrosinase in patients with stage II melanoma using recombinant modified vaccinia virus Ankara (MVA-hTyr).* Cancer Immunol Immunother, 2005. 54(5): p. 453-67.
22. Moorthy, V. S., et al., *Safety and immunogenicity of DNA/modified vaccinia virus ankara malaria vaccination in African adults.* J Infect Dis, 2003. 188(8): p. 1239-44.
23. Smith, C. L., et al., *Recombinant modified vaccinia Ankara primes functionally activated CTL specific for a melanoma tumor antigen epitope in melanoma patients with a high risk of disease recurrence.* Int J Cancer, 2005. 113(2): p. 259-66.

24. Webster, D. P., et al., *Safety of recombinant fowlpox strain FP9 and modified vaccinia virus Ankara vaccines against liver-stage P. falciparum malaria in non-immune volunteers.* Vaccine, 2006. 24(15): p. 3026-34.
25. Dorrell, L., et al., *Safety and tolerability of recombinant modified vaccinia virus Ankara expressing an HIV-1 gag/multiepitope immunogen (MVA.HIVA) in HIV-1-infected persons receiving combination antiretroviral therapy.* Vaccine, 2007. 25(17): p. 3277-83.
26. Peters, B. S., et al., *Studies of a prophylactic HIV-1 vaccine candidate based on modified vaccinia virus Ankara (MVA) with and without DNA priming: effects of dosage and route on safety and immunogenicity.* Vaccine, 2007. 25(11): p. 2120-7.

All publications mentioned in the above specification are herein incorporated by reference. Various modifications and variations of the described aspects and embodiments of the present invention will be apparent to those skilled in the art without departing from the scope of the present invention. Although the present invention has been described in connection with specific preferred embodiments, it should be understood that the invention as claimed should not be unduly limited to such specific embodiments. Indeed, various modifications of the described modes for carrying out the invention which are apparent to those skilled in the art are intended to be within the scope of the following claims.

The invention claimed is:

1. A method of inducing a T-cell mediated immune response against an influenza virus in a subject comprising administering to said subject a composition comprising nucleic acid encoding one or more epitopes of one or more internal proteins of influenza virus, wherein said composition comprises nucleic acid encoding at least two said epitopes, at least one epitope being from each of two or more internal proteins of influenza virus, wherein said nucleic acid is present in a viral vector, wherein said internal proteins comprise nucleoprotein and matrix 1 protein, wherein said epitopes are provided in the form of a nucleoprotein-matrix 1 protein fusion, wherein said internal proteins are from the H3N2 influenza strain subtype A/Panama/2007/99;

wherein said epitopes of the nucleoprotein (NP)-matrix 1 (M1) protein fusion comprise the amino acid sequence of SEQ ID NO: 1;

wherein the method induces T-cell mediated immune response to both nucleoprotein (NP) and matrix 1 protein (M1); and wherein said viral vector selected from the group consisting of an adenovirus based vector, a MVA based vector, an avipox based vector, an orthopox based vector, and a simian adenovirus based vector.

2. The method of claim 1, wherein said proteins are arranged in the order N terminus-nucleoprotein-matrix1-protein C terminus.

3. The method of claim 2, wherein said nucleoprotein and matrix 1 proteins are separated by a linker sequence.

4. The method of claim 3, wherein said linker sequence has the amino acid sequence GGGPGGG (SEQ ID NO. 3).

5. The method of claim 4, wherein the coding sequence of the nucleic acid sequence encoding said internal proteins and/or linker polypeptides has been codon optimised for human codon usage.

6. The method of claim 1, wherein said nucleic acid comprises SEQ ID NO:2.

7. The method of claim 1, wherein the composition further comprises an adjuvant.

\* \* \* \* \*